United States Patent
Armour et al.

(10) Patent No.: US 7,084,145 B2
(45) Date of Patent: Aug. 1, 2006

(54) TRIAZOLE COMPOUNDS USEFUL IN THERAPY

(75) Inventors: Robert Duncan Armour, Sandwich (GB); Andrew Douglas Baxter, Sandwich (GB); Justin Stephen Bryans, Sandwich (GB); Kevin Neil Dack, Sandwich (GB); Patrick Stephen Johnson, Sandwich (GB); Russell Andrew Lewthwaite, Sandwich (GB); Julie Newman, Sandwich (GB); David James Rawson, Sandwich (GB); Thomas Ryckmans, Sandwich (GB)

(73) Assignee: Pfizer Inc., New York, NY (US)

( * ) Notice: Subject to any disclaimer, the term of this patent is extended or adjusted under 35 U.S.C. 154(b) by 271 days.

(21) Appl. No.: 10/693,327

(22) Filed: Oct. 24, 2003

(65) Prior Publication Data

US 2004/0162278 A1    Aug. 19, 2004

Related U.S. Application Data

(60) Provisional application No. 60/428,632, filed on Nov. 22, 2002.

(30) Foreign Application Priority Data

Oct. 25, 2002  (GB)  .................. 0224919.1

(51) Int. Cl.
*A61K 31/4965* (2006.01)
*C07D 403/00* (2006.01)
(52) U.S. Cl. ............ 514/256; 514/318; 514/326; 546/193; 546/208; 544/333
(58) Field of Classification Search ........... 546/193, 546/208; 544/333; 514/256, 318, 326
See application file for complete search history.

(56) References Cited

U.S. PATENT DOCUMENTS 6,265,426 B1 *  7/2001  Alanine et al. ............ 514/383

FOREIGN PATENT DOCUMENTS

| DE | 574944 | 2/1932 |
| EP | 1293503 | 10/2003 |
| WO | WO 0158880 | 2/2000 |

OTHER PUBLICATIONS

Kakefuda, A. et al., Bioorganic & Medicinal Chemistry, vol. 10, pp. 1905-1912, 2002, "Discovery of 4,5-Diphenyl-1,2,4-triazole Derivatives as a Novel Class of Selective Antagonists for the Human $V_{1A}$ Receptor."

Kakefuda, A. et al., J. Med. Chem., vol. 45, pp. 2589-2598, 2002, "Synthesis and Pharmacological Evaluation of 5-(4-Biphenyl)-3-methyl-4-phenyl-1,2,4-triazole Derivatives as a Novel Class of Selective Antagonists for the Human Vasopressin $V_{1A}$ Receptor."

* cited by examiner

*Primary Examiner*—Joseph K. McKane
*Assistant Examiner*—Robert Shiao
(74) *Attorney, Agent, or Firm*—Gregg C. Benson; Carl J. Goddard

(57) ABSTRACT

The invention provides compounds of formula (I),

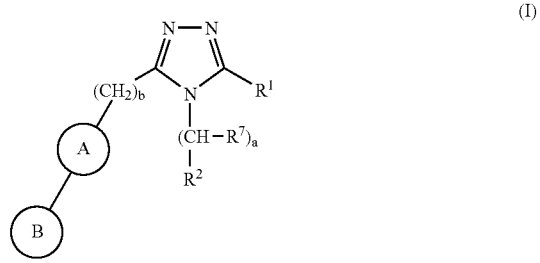

the pharmaceutically acceptable salts and solvates thereof, wherein A, B, $R^1$, $R^2$, and $R^7$ are as defined herein; pharmaceutical compositions thereof; combinations thereof; and uses thereof as vasopressin $V_{1A}$ antagonists.

9 Claims, No Drawings

TRIAZOLE COMPOUNDS USEFUL IN THERAPY

CROSS REFERENCE TO RELATED APPLICATION

This application claims the benefit of U.S. Provisional Application No. 60/428,632 filed Nov. 22, 2002 and U.K. Application No. 0224919.1 filed 25 Oct. 2002.

This invention relates to novel compounds useful in therapy and to processes for the preparation of, intermediates used in the preparation of, compositions containing and the uses of, such compounds.

WO 01/87855 discloses triazole derivatives as inhibitors of glycine transporter activity. WO 01/58880 and JP2000-63363 disclose triazole derivatives useful as arginine Vasopressin $V_{1A}$ receptor antagonists. Kakefuda et al., Bioorg. Med. Chem. 10 (2002) 1905–1912 and Kakefuda et al., J. Med. Chem., 2002, 45, 2589–2598 discuss the utility of 4,5-diphenyl-1,2,4-triazole derivatives as selective antagonists for the human $V_{1A}$ receptor and comment that the 4,5-diphenyl-1,2,4-triazole structure plays an essential role in $V_{1A}$ affinity.

The compounds of the present invention have been found to have useful pharmaceutical properties. They may be used to treat aggression, Alzheimer's disease, anorexia nervosa, anxiety disorder, asthma, atherosclerosis, cardiac failure, cardiovascular disease, cataract, central nervous system disease, cerebrovascular ischemia, cirrhosis, cognitive disorder, Cushing's disease, depression, diabetes mellitus, dysmenorrhoea, edema, emesis, endometriosis, gastrointestinal disease, glaucoma, gynaecological disease including dysmenorrhoea and mittlesmerchz, heart disease, hypertension, hyponatremia, intrauterine growth retardation, ischemia, ischemic heart disease, lung tumor, micturition disorder, motion sickness, neoplasm, nephrotoxicity, non-insulin dependent diabetes, obesity, obsessive/compulsive disorder, ocular hypertension, premature ejaculation, premature labor, pulmonary disease, Raynaud's disease, renal disease, renal failure, male and female sexual dysfunction, sleep disorder, spinal cord injury, thrombosis, urogenital tract infection, urolithiasis. In particular, they exhibit vasopressin antagonistic activity and can be used in the treatment of dysmenorrhoea.

There is a high unmet need in the area of menstrual disorders and it is estimated that up to 90% of all menstruating women are affected to some degree. Up to 42% of women miss work or other activities due to menstrual pain and it has been estimated that around 600 million work hours a year are lost in the US as a result {Coco, A. S. (1999). Primary dysmenorrhoea. [Review] [30 refs]. *American Family Physician*, 60, 489–96.}.

Menstrual pain in the lower abdomen is caused by myometrial hyperactivity and reduced uterine blood flow. These pathophysiological changes result in abdominal pain that radiates out to the back and legs. This may result in women feeling nauseous, having headaches and suffering from insomnia. This condition is called dysmenorrhoea and can be classified as either primary or secondary dysmenorrhoea.

Primary dysmenorrhoea is diagnosed when no abnormality causing the condition is identified. This affects up to 50% of the female population {Coco, A. S. (1999). Primary dysmenorrhoea. [Review] [30 refs]. *American Family Physician*, 60, 489–96; Schroeder, B. & Sanfilippo, J. S. (1999). Dysmenorrhoea and pelvic pain in adolescents. [Review] [78 refs]. *Pediatric Clinics of North America*, 46, 555–71}. Where an underlying gynaecological disorder is present, such as endometriosis, pelvic inflammatory disease (PID), fibroids or cancers, secondary dysmenorrhoea will be diagnosed. Secondary dysmenorrhoea is diagnosed in only approximately 25% of women suffering from dysmenorrhoea. Dysmenorrhoea can occur in conjunction with menorrhagia, which accounts for around 12% of referrals to gynaecology outpatients departments.

Currently, women suffering from primary dysmenorrhoea are treated with non-steroidal anti-inflammatory drugs (NSAID's) or the oral contraceptive pill. In cases of secondary dysmenorrhoea surgery may be undertaken to correct the underlying gynaecological disorder.

Women suffering from dysmenorrhoea have circulating vasopressin levels which are greater than those observed in healthy women at the same time of the menstrual cycle. Inhibition of the pharmacological actions of vasopressin, at the uterine vasopressin receptor, may prevent dysmenorrhoea.

According to the present invention there is provided a compound of formula (I),

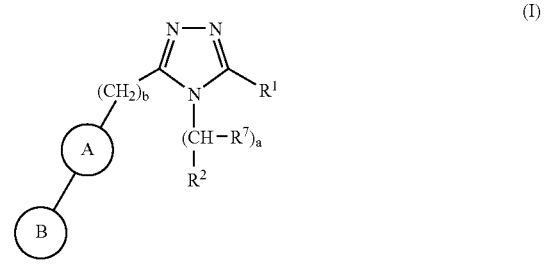

or a pharmaceutically acceptable salt or solvate thereof, wherein $R^1$ represents $C_1$–$C_6$ alkyl, —$(CH_2)_c$—$[C_3$–$C_8$ cycloalkyl]-, —$(CH_2)_c$—W or —$(CH_2)_c$-Z-$(CH_2)_d$—W;

W represents $C_1$–$C_6$ alkyl, $C_1$–$C_6$ alkyloxy, —$CO_2[C_1$–$C_6$ alkyl], —$CONR^4R^5$, a phenyl group, $NR^4R^5$, het$^2$ or het$^3$, the phenyl group being optionally substituted with one or more groups independently selected from halogen, $CF_3$, $OCF_3$, $R^3$, $OR^3$, $CO_2R^3$, $CONR^4R^5$, CN, $SO_2NR^4R^5$ and $NR^3SO_2Me$;

Z represents O or $S(O)_g$;

g represents 0, 1 or 2;

$R^2$ represents a phenyl group, optionally fused to a 5- or 6-membered aryl or heterocyclic group which may contain one or more heteroatoms selected from N, O or S; the phenyl group and the optionally fused group being optionally substituted with one or more groups independently selected from the list defined below;

Ring A represents a 4-, 5- or 6-membered saturated heterocyclic group containing at least one N;

Ring B represents a phenyl group or het$^1$, each group being optionally substituted with one or more groups independently selected from the list defined below;

$R^7$ independently represents H, $C_1$–$C_6$ alkyl, $OR^3$, —$(CH^2)_e$—$R^3$ or —$(CH_2)_f$—O—$(CH_2)_e$—$R^3$;

at each occurrence $R^3$ independently represents H, $C_1$–$C_6$ alkyl optionally substituted by Y, —$(CH_2)_g$-$[C_3$–$C_8$ cycloalkyl], phenyl, benzyl, pyridyl or pyrimidyl;

at each occurrence $R^4$ and $R^5$ independently represent H, $C_1$–$C_6$ alkyl (optionally substituted with $C_1$–$C_6$ alkyloxy), $(CH_2)_gCO_2$—$[C_1$–$C_6$ alkyl], —$SO_2Me$, —$(CH_2)_g$—$[C_3$–$C_8$ cycloalkyl], $SO_2Me$, phenyl, benzyl, pyridyl or pyrimidyl;

or $R^4$ and $R^5$ together with the N atom to which they are attached represent a heterocyclic group of from 3 to 8 atoms;

Y independently represents a phenyl group, $NR^4R^5$ or het$^4$, the phenyl group being optionally substituted with one or more groups independently selected from halogen, $CF_3$, $OCF_3$, $R^4$, $OR^4$, $CO_2R^4$, $CONR^4R^5$, CN, $SO_2NR^4R^5$, $NR^4SO_2Me$ and —$NR^4R^5$;

het$^1$ represents a 4-, 5- or 6-membered saturated, or unsaturated, heterocyclic group containing at least one N (but which may also contain one or more O or S atoms);

het$^2$ represents a 4-, 5-, 6- or 7-membered saturated, or unsaturated, heterocyclic group containing at least one N (but which may also contain one or more O or S atoms), optionally substituted with one or more groups independently selected from the list defined below;

het$^3$ represents a 4-, 5-, 6- or 7-membered saturated, or unsaturated, heterocyclic group containing at least one O (but which may also contain one or more N or S atoms), optionally substituted with one or more groups independently selected from the list defined below;

het$^4$ represents a 4-, 5-, 6- or 7-membered saturated or unsaturated heterocyclic group containing at least one N (but which may also contain one or more O or S atoms), optionally substituted with one or more groups independently selected from the list defined below;

substituents for $R^2$, Ring B, het$^1$, het$^2$, het$^3$ and het$^4$ are independently selected from the following list: halogen, $CF_3$, $OCF_3$, $R^3$, —$(CH_2)_e$—$SO_2Me$, —$(CH_2)_e$—$OR^3$, —$(CH_2)_e$—$CO_2R^3$, —$(CH_2)_e$—$CONR^4R^5$, —$(CH_2)_e$—CN, —$(CH_2)_e$—$SO_2NR^4R^5$, —$(CH_2)_e$—$NR^3SO_2Me$, —$(CH_2)_e$—$COR^3$, —$(CH_2)_e$—$OCOR^3$, —$(CH_2)_e$—$NHCOR^3$, —$(CH^2)_e$—$NR^3COR^6$ and —$(CH_2)_eNR^4R^5$;

at each occurrence $R^6$ independently represents H, $C_1$–$C_6$ alkyl optionally substituted by Y, —$(CH_2)_g$—[$C_3$–$C_8$ cycloalkyl], phenyl, benzyl, pyridyl or pyrimidyl;

a and b independently represent 0 or 1;

c, d, e and g independently represent 0, 1, 2, 3 or 4;

f independently represents 1, 2, 3 or 4;

provided that:
(i) a+b cannot equal 0; and
(ii) provided that when $R^1$ represents —$(CH_2)_c$-Z-$(CH_2)_d$—W and W represents $NR^4R^5$ or any N linked heterocyclic group then d must not be 0 or 1; and
(iii) provided that when $R^2$ represents a phenyl group substituted by a group of formula —$(CH_2)_e OR^3$, —$(CH^2)_e$—$CO_2R^3$ or —$(CH_2)_e OCOR^3$; or het$^1$ and/or het$^2$ are substituted by a group of formula —$(CH_2)_e OR^3$, —$(CH_2)_e$—$CO_2R^3$ or —$(CH_2)_e OCOR^3$; or when $R^7$ represents —$OR^3$ or —$(CH^2)_f$—O—$(CH_2)_e$— $R^3$ and e is 0; or when W represents a phenyl group substituted with —$OR^3$ or —$CO_2R^3$; and $R^3$ represents an alkyl group substituted with Y, and Y represents $NR^4R^5$ or an N-linked het$^3$;

then $R^3$ must represent $C_2$–$C_6$ alkyl substituted with Y.

Proviso (i) distinguishes the compounds of the invention from the prior art. Provisos (ii) and (iii) preclude chemically unstable compounds.

One skilled in the art would understand that an amine moiety spaced from another heteroatom by only a methylene link would be unstable upon exposure to hydrolytic media.

In the above definitions, halogen means fluoro, chloro, bromo or iodo. Alkyl, alkyloxy, alkanoyl, alkylene, alkenyl and alkenylene groups containing the requisite number of carbon atoms, except where indicated, can be unbranched or branched chain. Examples of alkyl include methyl, ethyl, n-propyl, i-propyl, n-butyl, i-butyl, sec-butyl and t-butyl.

Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,3-propylene and 1,2-propylene. Examples of cycloalkyl include cyclopropyl, cyclobutyl, cyclopentyl, cyclohexyl and cycloheptyl. Examples of cycloalkylene include cyclopropylene, cyclobutylene, cyclopentylene, cyclohexylene and cycloheptylene.

Preferred heterocycles included within the definition of "heterocycle" are pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl and quinoxalinyl, together with partially or fully saturated versions thereof as well as azetidinyl, pyrrolidinyl, piperidinyl, piperazinyl, homopiperazinyl and morpholinyl.

Preferred groups of compounds are those in which:
(i) $R^1$ is $C_3$–$C_6$ cycloalkyl or $C_1$–$C_4$ alkyl, and more preferably methyl, i-propyl or n-butyl;
(ii) $R^1$ is —$(CH_2)_c$—W or —$(CH_2)_c$-Z-$(CH_2)_d$—W;
(iii) $R^2$ is a phenyl group optionally substituted with one or more groups selected from halogen or —$(CH_2)_e$—$OR^3$;
(iv) ring A is selected from piperidinyl, piperazinyl, azetidinyl or pyrrolidinyl and more preferably it is piperidinyl or piperazinyl;
(v) ring B is a phenyl group substituted groups one or more groups selected from halogen, $CF_3$, $OCF_3$, $R^3$, —$(CH_2)_e$—$OR^3$ and CN;
(vi) ring B is an unsubstituted phenyl group;
(vii) ring B is het$^1$
(viii) $R^7$ is $C_1$–$C_4$ alkyl, more preferably it is $C_1$–$C_4$ straight chain alkyl and most preferably it is methyl or ethyl;
(ix) $R^7$ is $CH_2OH$;
(x) W is a halo substituted phenyl group;
(xi) W is $NR^4R^5$, preferably it is selected from NHMe, NMe$_2$, NEt$_2$, N(iPr)$_2$, or N(nPr)$_2$;
(xii) W is $C_1$–$C_6$ alkyl, preferably methyl or ethyl;
(xiii) W is $CO_2$[$C_1$–$C_6$ alkyl], preferably $CO_2^tBu$;
(xiv) W is het$^2$ or het$^3$;
(xv) W is OMe;
(xvi) W is $CONR^4R^5$;
(xvii) W is halogen, preferably chloro or fluoro
(xviii) Z is O;
(xix) $R^3$ and $R^6$ are independently $C_{1-4}$ alkyl, more preferably unsubstituted $C_{1-4}$ alkyl, even more preferably methyl or tert-butyl;
(xx) $R^3$ and $R^6$ are independently H or benzyl;
(xxi) $R^4$ and $R^5$ are independently selected from H, methyl, ethyl, n-propyl or i-propyl;
(xxii) $R^4$ and $R^5$ together with the nitrogen to which they are attached form a heterocycle preferably selected from piperidinyl, 2-oxa-5-aza-bicyclo[2.2.1]heptanyl, piperazinyl, azetidinyl, imidazolyl, pyrazolyl, triazolyl, morpholinyl and pyrrolidinyl;
(xxiii) $R^4$ and $R^5$ are independently selected from $SO_2Me$ or benzyl;
(xxiv) $R^4$ and $R^5$ are independently $CH_2CO_2$—[$C_1$–$C_6$ alkyl], preferably $CH_2CO_2^tBu$;
(xxiv) $R^4$ and $R^5$ are independently $C_1$–$C_6$ alkyl substituted by $C_1$–$C_6$ alkyloxy, preferably $C_2$–$C_3$ alkyl substituted by methoxy;
(xxv) het$^1$ is selected from optionally substituted pyridinyl, pyrimidinyl, pyrazinyl, pyridazinyl, triazinyl, triazolyl, tetrazolyl, pyrrolyl, pyrazolyl, imidazolyl, oxazolyl, isoxazolyl, thiazolyl, piperidinyl, piperazinyl, azetidinyl, morpholinyl, 2-oxa-5-aza-bicyclo[2.2.1.]heptanyl or pyrrolidinyl, and more preferably selected from pyridinyl, pyrazinyl or pyrimidinyl, optionally substituted by any one of $R^3$;

(xxvi) $het^2$ is selected from substituted or unsubstituted pyridinyl, pyrimidinyl, pyrazinyl, pyridazinyl, triazinyl, triazolyl, tetrazolyl, pyrrolyl, pyrazolyl, imidazolyl, oxazolyl, isoxazolyl, thiazolyl, piperidinyl, piperazinyl, N-methyl piperazinyl, azetidinyl, morpholinyl, 2-oxa-5-aza-bicyclo[2.2.1]heptanyl or pyrrolidinyl and more preferably selected from imidazolyl, piperidinyl, piperazinyl, N-methyl piperazinyl, azetidinyl, morpholinyl, 2-oxa-5-aza-bicyclo[2.2.1]heptanyl or pyrrolidinyl. Even more preferably it is pyridinyl;

(xxvii) $het^3$ is selected from substituted or unsubstituted tetrahydro-furanyl or tetrahydro-pyranyl;

(xxviii) substituents for $R^2$, Ring B, $het^1$, $het^2$, $het^3$ and $het^4$ are independently $CF_3$, $R^3$, $—(CH_2)_e—OR^3$, $—(CH_2)_e—CO_2R^3$, $—(CH_2)_3—CN$, $—(CH_2)_e—SO_2Me$, $—(CH_2)_e—COR^3$;

(xxix) Z is O or S;

(xxx) a is 1;

(xxxi) b is 0;

(xxxii) c is selected from 0, 1 or 2. More preferably it is selected from 0 or 1;

(xxiii) e is selected from 0, 1 or 2 and more preferably selected from 0 or 1, even more preferably it is 0;

(xxxiv) d is selected from 0, 1, 2 or 3 and more preferably it is selected from 0 to 2;

(xxxv) f is selected from 1 or 2, preferably it is 1;

(xxvi) g is 0.

Preferred compounds according to the present invention are:

(S)-4-[5-Butyl-4-(1-phenyl-ethyl)-4H-[1,2,4]triazol-3-yl]-3,4,5,6-tetrahydro-2H-[1,2']bipyridinyl;

2-[4-(4-Benzyl-5-isobutyl-4H-[1,2,4]triazol-3-yl)-piperidin-1-yl]-pyrimidine;

(S)-4-[5-Methyl-4-(1-phenyl-ethyl)-4H-[1,2,4]triazol-3-yl]-3,4,5,6-tetrahydro-2H-[1,2']bipyridinyl;

4-[4-Benzyl-5-butyl-4H-[1,2,4]triazol-3-yl]-3,4,5,6-tetrahydro-2H-[1,2']bipyridinyl;

2-[4-(4-Benzyl-5-isopropyl-4H-[1,2,4]triazol-3-yl)-piperidin-1-yl]-pyrimidine;

2-[4-(4-Benzyl-5-cyclopropyl-4H-[1,2,4]triazol-3-yl)-piperidin-1-yl]-pyrimidine;

(S)-2-{4-[5-Methyl-4-(1-phenyl-propyl)-4H-[1,2,4]triazol-3-yl)-piperidin-1-yl]-pyrimidine;

2-[4-(4-Benzyl-5-propyl-4H-[1,2,4]triazol-3-yl)-piperidin-1-yl]-pyrimidine;

2-{4-[4-Benzyl-5-(2-chloro-phenoxymethyl)-4H-[1,2,4]triazol-3-yl]-piperidin-1-yl}-pyrimidine;

2-[4-(4-Benzyl-5-butyl-4H-[1,2,4]triazol-3-yl)-piperidin-1-yl]-pyrimidine;

(S)-2-{4-[5-Methyl-4-(1-phenyl-ethyl)-4H-[1,2,4]triazol-3-yl)-piperidin-1-yl]-pyrimidine;

2-{4-[4-Benzyl-5-(4-fluoro-phenoxymethyl)-4H-[1,2,4]triazol-3-yl]-piperidin-1-yl}-pyrimidine;

2-{4-[5-Methyl-4-(3-methyl-benzyl)-4H-[1,2,4]triazol-3-yl)-piperidin-1-yl]-pyrimidine;

(S)-2-{4-[5-Methyl-4-(1-phenyl-ethyl)-4H-[1,2,4]triazol-3-ylmethyl)-piperidin-1-yl}-pyrimidine;

2-{4-[4-(3-Fluoro-benzyl)-5-methyl-4H-[1,2,4]triazol-3-yl)-piperidin-1-yl]-pyrimidine;

4-(4-Benzyl-5-morpholin-4-ylmethyl-4H-[1,2,4]triazol-3-yl)-3,4,5,6-tetrahydro-2H-[1,2']bipyridinyl;

4-(4-Benzyl-5-benzyloxymethyl-4H-[1,2,4]triazol-3-yl)-3,4,5,6-tetrahydro-2H-[1,2']bipyridinyl;

4-(4-Benzyl-5-methyl-4H-[1,2,4]triazol-3-yl)-3,4,5,6-tetrahydro-2H-[1,2']bipyridinyl;

(R)-2-[3-Methyl-5-(1-pyrimidin-2-yl-piperidin-4-yl)-[1,2,4]triazol-4-yl]-2-phenyl-ethanol;

2-[4-(4-Benzyl-5-methyl-4H-[1,2,4]triazol-3-yl)-piperidin-1-yl]-4-methyl-pyrimidine;

2-[4-(4-Benzyl-5-methyl-4H-[1,2,4]triazol-3-yl)-piperidin-1-yl]-pyrimidine;

4-(4-Benzyl-5-methyl-4H-[1,2,4]triazol-3-yl)-1-phenyl-piperidine;

2-[4-(4-Benzyl-5-methyl-4H-[1,2,4]triazol-3-yl)-piperidin-1-yl]-pyrazine;

4-(4-Benzyl-5-piperidin-1-ylmethyl-4H-[1,2,4]triazol-3-yl)-3,4,5,6-tetrahydro-2H-[1,2']bipyridinyl;

(S)-4-[4-(1-Phenyl-ethyl)-5-piperidin-1-ylmethyl-4H-[1,2,4]triazol-3-yl]-3,4,5,6-tetrahydro-2H-[1,2']bipyridinyl;

4-[4-Benzyl-5-(4-methoxy-piperidin-1-ylmethyl)-4H-[1,2,4]triazol-3-yl]-3,4,5,6-tetrahydro-2H-[1,2']bipyridinyl;

(S)-4-[5-(4-Methoxy-piperidin-1-ylmethyl)-4-(1-phenyl-ethyl)-4H-[1,2,4]triazol-3-yl]-3,4,5,6-tetrahydro-2H-[1,2']bipyridinyl;

4-[4-Benzyl-5-(3,4,5,6-tetrahydro-2H-[1,2']bipyridinyl-4-yl)-4H-[1,2,4]triazol-3-ylmethyl]-piperazine-1-carboxylic acid benzyl ester;

4-[4-Benzyl-5-(2-morpholin-4-yl-ethoxymethyl)-4H-[1,2,4]triazol-3-yl]-3,4,5,6-tetrahydro-2H-[1,2']bipyridinyl.

4-[4-Benzyl-5-{(3R)-3-methoxy-pyrrolidin-1-ylmethyl)-4H-[1,2,4]triazol-3-yl]-3,4,5,6-tetrahydro-2H-[1,2']bipyridinyl 4-[4-Benzyl-5-{(3S)-3-methoxy-pyrrolidin-1-ylmethyl)-4H-[1,2,4]triazol-3-yl]-3,4,5,6-tetrahydro-2H-[1,2']bipyridinyl 1-[4-Benzyl-5-(3,4,5,6-tetrahydro-2H-[1,2']bipyridinyl-4-yl)-4H-[1,2,4]triazol-3-ylmethyl]-pyrrolidin-3-ol 4-(4-Benzyl-5-pyrrolidin-1-ylmethyl-4H-[1,2,4]triazol-3-yl)-3,4,5,6-tetrahydro-2H-[1,2']bipyridinyl 4-[4-Benzyl-5-(2-oxa-5-aza-bicyclo[2.2.1]hept-5-ylmethyl)-4H-[1,2,4]triazol-3-yl]-3,4,5,6-tetrahydro-2H-[1,2']bipyridinyl 4-[4-Benzyl-5-(4-methoxy-piperidin-1-ylmethyl)-4H-[1,2,4]triazol-3-yl]-3,4,5,6-tetrahydro-2H-[1,2']bipyridinyl 4-[4-(4-Fluoro-benzyl)-5-methyl-4H-[1,2,4]triazol-3-yl]-3,4,5,6-tetrahydro-2H-[1,2']bipyridinyl 4-[4-(3-Methoxy-benzyl)-5-methyl-4H-[1,2,4]triazol-3-yl]-3,4,5,6-tetrahydro-2H-[1,2']bipyridinyl 4-[5-Methyl-4-(3-methyl-benzyl)-4H-[1,2,4]triazol-3-yl]-3,4,5,6-tetrahydro-2H-[1,2']bipyridinyl 4-[4-(3-Chloro-benzyl)-5-methyl-4H-[1,2,4]triazol-3-yl]-3,4,5,6-tetrahydro-2H-[1,2']bipyridinyl N-Benzyl-2-[4-benzyl-5-(3,4,5,6-tetrahydro-2H-[1,2']bipyridinyl-4-yl)-4H-[1,2,4]triazol-3-yl]-acetamide 2-[4-Benzyl-5-(3,4,5,6-tetrahydro-2H-[1,2']bipyridinyl-4-yl)-4H-[1,2,4]triazol-3-ylmethoxy]-ethylamine

[4-Benzyl-5-(3,4,5,6-tetrahydro-2H-[1,2']bipyridinyl-4-yl)-4H-[1,2,4]triazol-3-ylmethyl]-ethyl-amine

[4-Benzyl-5-(3,4,5,6-tetrahydro-2H-[1,2']bipyridinyl-4-yl)-4H-[1,2,4]triazol-3-ylmethyl]-(2-methoxy-ethyl)-amine

[4-Benzyl-5-(3,4,5,6-tetrahydro-2H-[1,2']bipyridinyl-4-yl)-4H-[1,2,4]triazol-3-ylmethyl]-(3-methoxy-propyl)-amine 1-{4-[4-Benzyl-5-(3,4,5,6-tetrahydro-2H-[1,2']bipyridinyl-4-yl)-4H-[1,2,4]triazol-3-ylmethyl]-piperazin-1-yl}-ethanone
4-[4-Benzyl-5-(4-methanesulfonyl-piperazin-1-ylmethyl)-4H-[1,2,4]triazol-3-yl]-3,4,5,6-tetrahydro-2H-[1,2]bipyridinyl
N-[4-Benzyl-5-(3,4,5,6-tetrahydro-2H-[1,2']bipyridinyl-4-yl)-4H-[1,2,4]triazol-3-ylmethyl]-methanesulfonamide
[4-Benzyl-5-(3,4,5,6-tetrahydro-2H-[1,2']bipyridinyl-4-yl)-4H-[1,2,4]triazol-3-ylmethyl]-(2-methoxy-ethyl)-methyl-amine
[4-Benzyl-5-(3,4,5,6-tetrahydro-2H-[1,2']bipyridinyl-4-yl)-4H-[1,2,4]triazol-3-ylmethyl]-(3-methoxy-propyl)-methyl-amine
4-(4-Benzyl-5-morpholin-4-ylmethyl-4H-[1,2,4]triazol-3-yl)-3'-methyl-3,4,5,6-tetrahydro-2H-[1,2']bipyridinyl
4-(4-Benzyl-5-morpholin-4-ylmethyl-4H-[1,2,4]triazol-3-yl)-3'-trifluoromethyl-3,4,5,6-tetrahydro-2H-[1,2']bipyridinyl
4-(4-Benzyl-5-morpholin-4-ylmethyl-4H-[1,2,4]triazol-3-yl)-3,4,5,6-tetrahydro-2H-[1,2']bipyridinyl-3'-carbonitrile
4-(4-Benzyl-5-morpholin-4-ylmethyl-4H-[1,2,4]triazol-3-yl)-3,4,5,6-tetrahydro-2H-[1,2']bipyridinyl-3'-carboxylic acid amide
(S)-4-[4-(1-Phenyl-ethyl)-5-(4-pyridin-2-yl-piperazin-1-ylmethyl)-4H-[1,2,4]triazol-3-ylmethyl]-morpholine trihydrochloride
(S)-4-[4-(1-Phenyl-ethyl)-5-(4-pyrimidin-2-yl-piperazin-1-ylmethyl)-4H-[1,2,4]triazol-3-ylmethyl]-morpholine trihydrochloride
1-[4-Benzyl-5-(1-pyrimidin-2-yl-piperidin-4-yl)-4H-[1,2,4]triazol-3-ylmethyl]-piperidin-3-ol
(R)-2-[4-Benzyl-5-(3,4,5,6-tetrahydro-2H-[1,2']bipyridinyl-4-yl)-4H-[1,2,4]triazol-3-yl]-pyrrolidine-1-carboxylic acid tert-butyl ester
(R)-4-[4-Benzyl-5-(tetrahydro-furan-3-yloxymethyl)-4H-[1,2,4]triazol-3-yl]3,4,5,6-tetrahydro-2H-[1,2']bipyridinyl
(S)-4-[4-Benzyl-5-(tetrahydro-furan-3-yloxymethyl)-4H-[1,2,4]triazol-3-yl]3,4,5,6-tetrahydro-2H-[1,2']bipyridinyl
{[4-Benzyl-5-(3,4,5,6-tetrahydro-2H-[1,2']bipyridinyl-4-yl)-4H-[1,2,4]triazol-3-ylmethyl]-methyl-amino}-acetic acid tert-butyl ester
4-[4-Benzyl-5-(tetrahydro-pyran-4-ylmethyl)-4H-[1,2,4]triazol-3-yl]-3,4,5,6-tetrahydro-2H-[1,2']bipyridinyl
4-[4-Benzyl-5-(tetrahydro-furan-2-yl)-4H-[1,2,4]triazol-3-yl]-3,4,5,6-tetrahydro-2H-[1,2']bipyridinyl
4-(4-Benzyl-5-ethoxymethyl-4H-[1,2,4]triazol-3-yl)-3,4,5,6-tetrahydro-2H-[1,2']bipyridinyl
4-[4-Benzyl-5-(2-methoxy-ethoxymethyl)-4H-[1,2,4]triazol-3-yl]-3,4,5,6-tetrahydro-2H-[1,2']bipyridinyl
[4-Benzyl-5-(3,4,5,6-tetrahydro-2H-[1,2']bipyridinyl-4-yl)-4H-[1,2,4]triazol-3-ylmethoxy]-acetic acid tert-butyl ester
N-Benzyl-2-[4-benzyl-5-(3,4,5,6-tetrahydro-2H-[1,2']bipyridinyl-4-yl)-4H-[1,2,4]triazol-3-ylmethoxy]-acetamide
4-(4-Benzyl-5-methylsulfanylmethyl-4H-[1,2,4]triazol-3-yl)-3,4,5,6-tetrahydro-2H-[1,2']bipyridinyl
4-(4-Benzyl-5-pyrazol-1-ylmethyl-4H-[1,2,4]triazol-3-yl)-3,4,5,6-tetrahydro-2H-[1,2']bipyridinyl
4-(4-Benzyl-5-[1,2,3]triazol-2-ylmethyl-4H-[1,2,4]triazol-3-yl)-3,4,5,6-tetrahydro-2H-[1,2']bipyridinyl
4-(4-Benzyl-5-[1,2,3]triazol-1-ylmethyl-4H-[1,2,4]triazol-3-yl)-3,4,5,6-tetrahydro-2H-[1,2']bipyridinyl
4-[4-Benzyl-5-(pyridin-4-yloxymethyl)-4H-[1,2,4]triazol-3-yl]-3,4,5,6-tetrahydro-2H-[1,2']bipyridinyl Of particular interest are the following compounds:
4-[4-Benzyl-5-butyl-4H-[1,2,4]triazol-3-yl]-3,4,5,6-tetrahydro-2H-[1,2']bipyridinyl
4-(4-Benzyl-5-morpholin-4-ylmethyl-4H-[1,2,4]triazol-3-yl)-3,4,5,6-tetrahydro-2H-[1,2']bipyridinyl
4-(4-Benzyl-5-benzyloxymethyl-4H-[1,2,4]triazol-3-yl)-3,4,5,6-tetrahydro-2H-[1,2']bipyridinyl
4-(4-Benzyl-5-piperidin-1-ylmethyl-4H-[1,2,4]triazol-3-yl)-3,4,5,6-tetrahydro-2H-[1,2']bipyridinyl
(S)-4-[4-(1-Phenyl-ethyl)-5-piperidin-1-ylmethyl-4H-[1,2,4]triazol-3-yl]-3,4,5,6-tetrahydro-2H-[1,2']bipyridinyl
4-[4-Benzyl-5-(4-methoxy-piperidin-1-ylmethyl)-4H-[1,2,4]triazol-3-yl]-3,4,5,6-tetrahydro-2H-[1,2']bipyridinyl The pharmaceutically acceptable salts of the compounds of formula (I) include the acid addition and base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, accharate, benzoate, methanesulphonate, ethanesulphonate, benzenesulphonate, p-toluenesulphonate, palmoate and pamoate salts.

Suitable base salts are formed from bases, which form non-toxic salts and examples are the sodium, potassium, aluminium, calcium, magnesium, zinc and diethanolamine salts.

For a review on suitable salts see Berge et al, J. Pharm. Sci., 66, 1–19, 1977.

The pharmaceutically acceptable solvates of the compounds of formula (I), or salts thereof include the hydrates thereof.

Also included within the scope of the present invention are the polymorphs of compounds of formula (I).

A compound of the formula (I) may contain one or more asymmetric carbon atoms and therefore exist in two or more stereoisomeric forms. The present invention also includes the individual stereoisomers of the compounds of the formula (I) and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as H.P.L.C. of the corresponding racemate using a suitable chiral support or by fractional crystallisation of the diastereoisomeric salts formed by reaction of the corresponding racemate with a suitable optically active acid or base, as appropriate.

The present invention also includes all suitable isotopic variations of a compound of the formula (I), or a pharmaceutically acceptable salt thereof. An isotopic variation of a compound of the formula (I) or a pharmaceutically acceptable salt thereof is defined as one in which at least one atom is replaced by an atom having the same atomic number but an atomic mass different from the atomic mass usually found in nature. Examples of isotopes that can be incorporated into compounds of the formula (I) and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the compounds of the formula (I) and pharmaceutically acceptable salts thereof, for example, those in which a radioactive isotope such as $^3H$ or $^{14}C$ is incorporated, are useful in drug and/or substrate tissue distribution studies. Tritiated, i.e. $^3H$, and carbon-14, i.e. $^{14}C$, isotopes are particularly preferred for their ease of preparation and detectability. Further, substitution with isotopes such as deuterium, i.e. $^2H$, may afford certain therapeutic advantages resulting from greater metabolic stability, for example, increased in vivo half-life or reduced dosage requirements and hence may be preferred in some circumstances. Isotopic variations of the compounds of formula (I) and pharmaceutically acceptable salts thereof, according to this invention, can generally be prepared by conventional procedures such as by the illustrative methods or by the preparations described in the Examples and Preparations hereafter using appropriate isotopic variations of suitable reagents.

According to the present invention there is also provided a process for the production of a compound of formula (I), which comprises:

a) reacting a compound of formula (II) with a compound of formula (III)

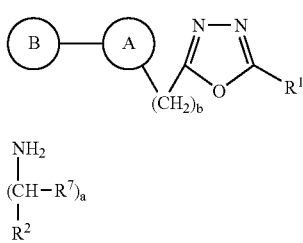

(II)

(III)

in which ring A and ring B, $R^1$, $R^2$, $R^7$, a and b are as hereinbefore defined.

b) reacting a compound of formula (VI)

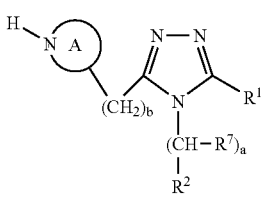

(VI)

in which ring A, $R^1$, $R^2$, $R^7$, a and b are as hereinbefore defined, with a compound of formula (VII)

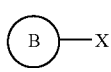

(VII)

in which ring B is as defined above and X represents a leaving group such as halogen.

Unless otherwise provided herein:
WSCDI means 1-(3-dimethylaminopropyl)-3-ethylcarbodiimide hydrochloride;
DCC means N,N'-dicyclohexylcarbodiimide;
HOAT means 1-hydroxy-7-azabenzotriazole;
HOBT means 1-hydroxybenzotriazole hydrate;
PyBOP® means Benzotriazol-1-yloxytris(pyrrolidino) phosphoniumhexa fluorophosphate;
PyBrOP® means bromo-tris-pyrrolidino-phosphonium-hexafluoro phosphate;
Mukaiyama's reagent means 2-chloro-1-methylpyridinium iodide;
KHMDS means potassium bis(trimethylsilyl)amide;
Hünig's base means N-ethyldiisopropylamine;
$Et_3N$ means triethylamine;
NMM means N-methylmorpholine;
HMDS means hexamethyldisilazane
BINAP means 2,2'-bis(diphenylphosphino)-1,1'-binaphthyl;
Dba means dibenzylideneacetone;
Boc means tert-butoxycarbonyl;
CBz means benzyloxycarbonyl;
p-TSA means p-toluenesulphonic acid
TBAF means tetra-butyl ammonium fluoride
MeOH means methanol, EtOH means ethanol, and EtOAc means ethyl acetate;
THF means tetrahydrofuran, DMSO means dimethyl sulphoxide, and DCM means dichloromethane, DMF means N,N-dimethylformamide, NMP means N-methyl-2-pyrrolidinone;
AcOH means acetic acid, TFA means trifluoroacetic acid.

The following schemes illustrate the preparation of compounds of the formula (I), throughout which Rings A and B, $R^1$, $R^2$, $R^7$, a and b are as hereinbefore defined:

Scheme 1.

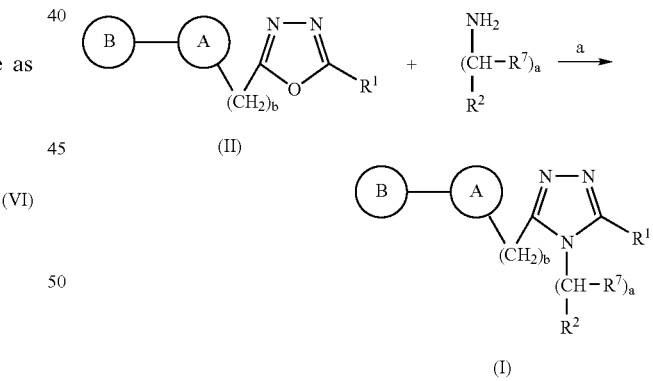

Amines suitable for use as compound (III) are commercially available or are known in the literature.

Step (a): Benzylamine (III) is reacted with oxadiazole (II) to give the compound of formula (I). This reaction is carried out by heating the starting materials to elevated temperatures such as 100–150° C. for 1 to 48 hours with a suitable acidic catalyst such as p-TSA, or Lewis acid catalyst such as magnesium chloride, optionally using a high boiling solvent such as xylene.

Preferred conditions are: 2 eq. of amine (III) with 0.4 eq. magnesium chloride at 140° C. for 1–18 hours, or 1.2 eq. amine (III), cat. P-TSA, in xylene for 48 hrs.

When ring B is linked to A via an N atom, then:

Scheme 2.

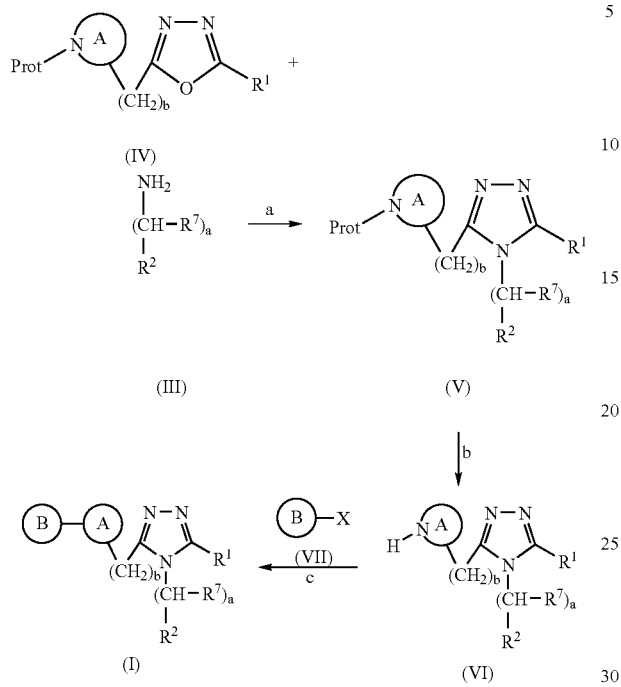

Prot represents a suitable protecting group for nitrogen. Standard methodology for nitrogen protecting groups is used, such as that found in textbooks, (e.g. "Protecting Groups in Organic Synthesis" by T. W. Greene and P. Wutz).

X represents a leaving group such as halogen.

Compounds suitable for use as compound (VII) are commercially available or are known in the literature.

Step (b): Deprotection of compound (V) is undertaken using standard methodology, as described in "Protecting Groups in Organic Synthesis" by T. W. Greene and P. Wutz".

When Prot is Boc the preferred method is hydrogen chloride in a suitable solvent such as 1,4-dioxane at room temperature for 1–16 hours, or a solution of trifluoroacetic acid in dichloromethane for 1–2 hours.

When Prot is CBz the preferred method is hydrogenolysis using a suitable palladium catalyst in a solvent such as ethanol.

When Prot is an allyl carbamate, preferred conditions are thiobenzoic acid and a suitable palladium catalyst such as Pd$_2$(Dba)$_3$ with a suitable phosphine additive such as 1,4-bis(diphenylphosphino)butane in tetrahydrofuran for 20 minutes.

Step (c): Arylation of compound (VI) can be carried out by a palladium catalysed cross-coupling reaction using a suitable base (t-BuONa), a catalytic amount of suitable additive such as 2,2'-bis(diphenylphosphino)-1,1'-binaphthyl and a suitable palladium catalyst in toluene at elevated temp for 1 to 24 hours under an inert atmosphere, to give compound (I). Alternatively compound (I) can be prepared by reaction of the amine (VI) with compound (VII) by heating at elevated temperature such as 50° C.–140° C. in a suitable solvent such as DMF, NMP or 1,4-dioxan for about 1–48 hrs with a base such as potassium carbonate, sodium hydrogen carbonate or Hünig's base.

Preferred conditions are: 1–2.5 eq. Halide (VII) 1–2 eq. potassium carbonate in N,N-dimethylformamide at 50° C. for 4–18 hours, or, 1–2.5 eq. Halide (VII), 2–3 eq. Hünig's base, in 1,4-dioxan or NMP at reflux for 18–48 hrs, or, 1 eq. Halide (VII), 3.5 eq. NaOt-Bu, 0.08 eq BINAP, 0.4 eq. Pd(dba)$_2$, in toluene for 8 hrs at 70° C.

Compounds suitable for use as compounds (II) and (IV) are known in the literature or can be prepared as shown in scheme 3.1 and 3.2.

Scheme 3.1

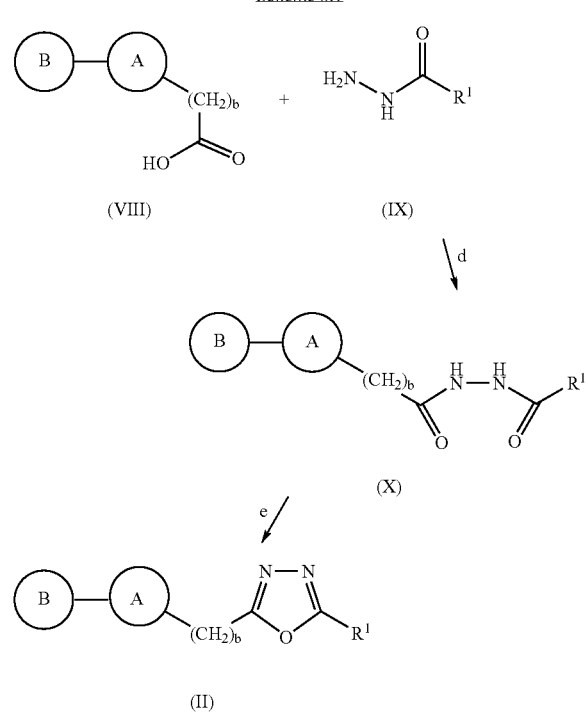

When rings A and B are linked through an N atom then:

Scheme 3.2

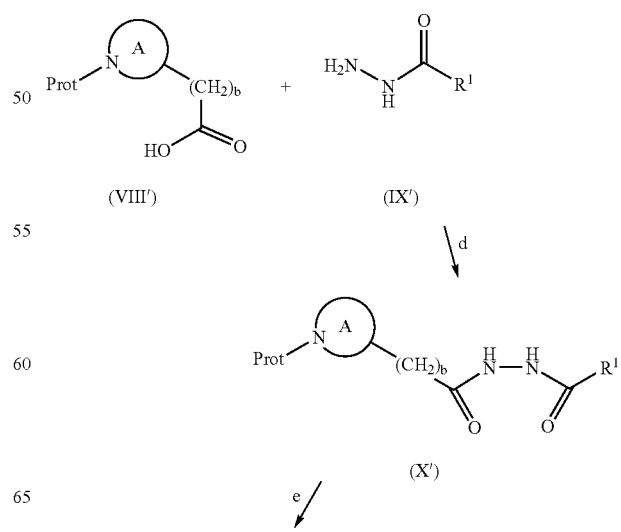

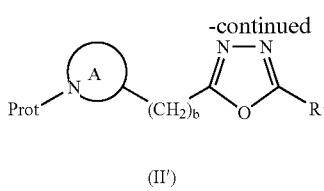

(II')

Compounds (VIII)/(VIII') and (IX) are either commercially available or are known in methodology such as the hydrolysis of the corresponding ester. (see Preparation 1).

Step (d): Reaction of carboxylic acid (VIII/VIII') with hydrazide (IX) can be carried out by standard methods.

Coupling may be undertaken by using either (i) an acyl chloride derivative of acid (VIII/VIII')+hydrazide (IX), with an excess of acid acceptor in a suitable solvent, or
(ii) the acid (VIII/VIII') with a conventional coupling agent+hydrazide (IX), optionally in the presence of a catalyst, with an excess of acid acceptor in a suitable solvent.

Typically the conditions are as follows:
(i) acid chloride of acid (VIII/VIII') (generated in-situ), an excess of hydrazide, optionally with an excess of 3° amine such as $Et_3N$, Hünig's base or NMM, in DCM or THF, without heating for 1 to 24 hrs, or
(ii) acid (VIII/VIII'), WSCDI/DCC and HOBT/HOAT, an excess of hydrazide (IX), with an excess of NMM, $Et_3N$, Hünig's base in THF, DCM or EtOAc, at rt. for 4 to 48 hrs; or, acid (VIII/VIII'), PYBOP®/PyBrOP®/Mukaiyama's reagent, an excess of hydrazide (IX), with an excess of NMM, $Et_3N$, Hünig's base in THF, DCM or EtOAc, at rt. for 4 to 24 hrs.

The preferred conditions are: acid chloride of acid (VIII/VIII') (generated in-situ), 2 eq. hydrazide, in DCM at rt. for 16 hours, or the carboxylic acid (VIII/VIII'), 1 eq HOBT, 1 eq. WSCDI, 1.2 eq. hydrazide (IX) in dichloromethane at room temperature for 18 hours.

Step (e): Cyclisation of compound (X/X') is carried out under suitable dehydrating conditions, at elevated temperatures for up to 18 hours.

Typically, dehydrating agents such as polyphosphoric acid or phosphorous oxychloride are used at temperatures from 50 to 120° C. for 5 minutes to 12 hours, optionally the reaction can be carried out under an inert atmosphere. Alternatively, the oxadiazole (II/II') may be prepared according to the method of Rigo et. al. Synth. Commun. 16(13), 1665, 1986.

Preferred conditions are: Phosphorous oxychloride at 100° C. for 2 hours, or 1.8 eq. HMDS, cat. imidazole, cat. TBAF in chlorobenzene at 150° C. for 18 hours.

Alternative routes to compound (X/X') are shown below in schemes 4.1 and 4.2:

Scheme 4.1

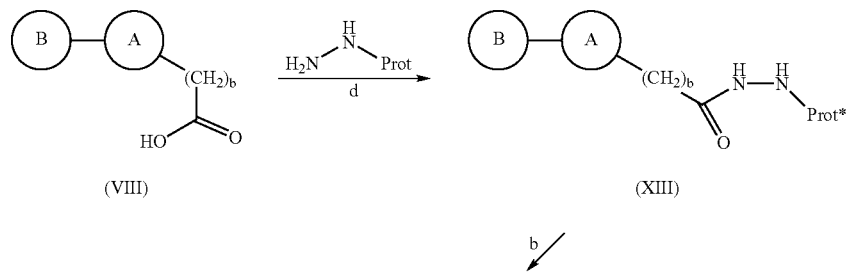

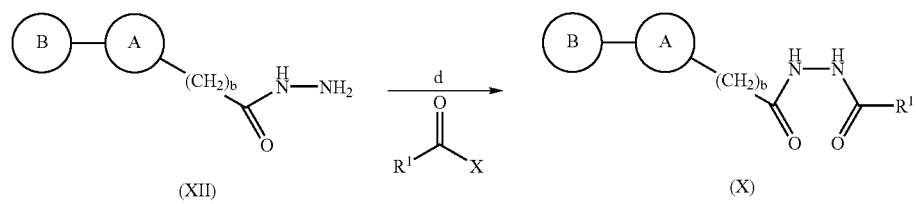

Scheme 4.2

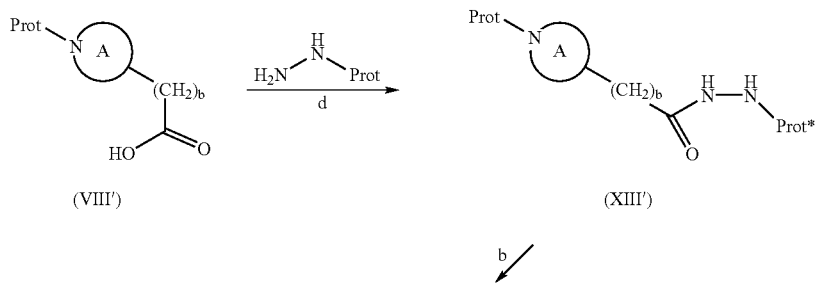

-continued

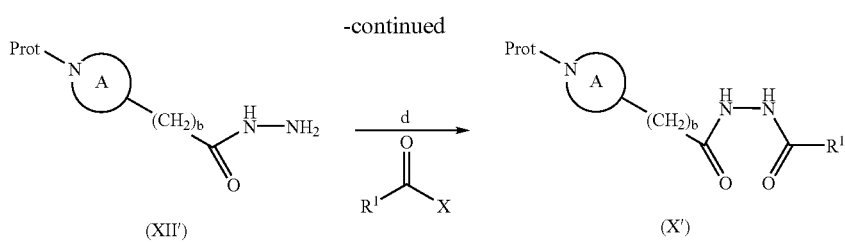

(XII')       (X')

X is OH or Cl.

Carboxylic acid (VIII/VIII') and protected hydrazine, where prot* is typically Boc, may be coupled to give compound (XIII/XIII'), using the conditions described for the preparation of (X/X') above, and then prot* is removed using standard methodology as described in step b, to give (XII/XII').

Compound (X/X') may then be obtained by the coupling of hydrazide (XII/XII') with a carboxylic acid or it's derivative ($R^1C(O)X$, where X is OH or Cl), under the conditions described previously for step d.

Alternative routes to compound (XII/XII') are shown below in schemes 5.1 and 5.2:

Scheme 5.1

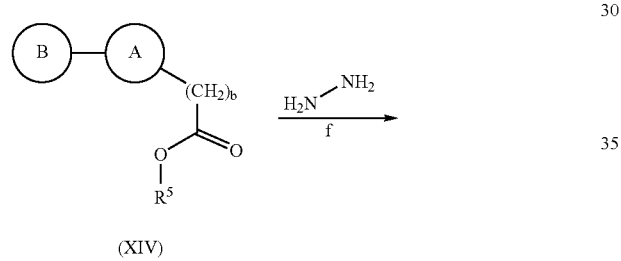

(XIV)

(XII)

Scheme 5.2

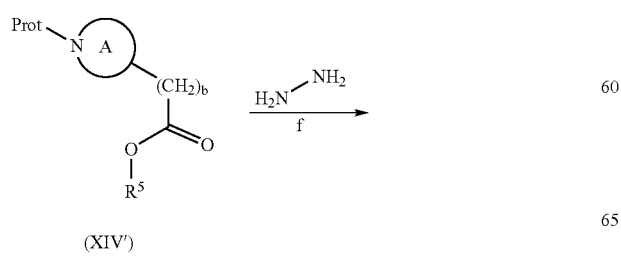

(XIV')

-continued

Prot—N—A—(CH₂)ᵦ—C(O)—N(H)—NH₂

(XII')

Step (f): The ester (XIV/XIV') may be reacted with hydrazine in a suitable solvent, such as methanol at elevated temperature to provide the hydrazide (XII/XII').

Preferred conditions: 3 eq. hydrazine, in methanol, at reflux for 18 hrs.

Compounds of the formula (I/V') may be prepared according to the routes described in Schemes 6.1 and 6.2:

Scheme 6.1

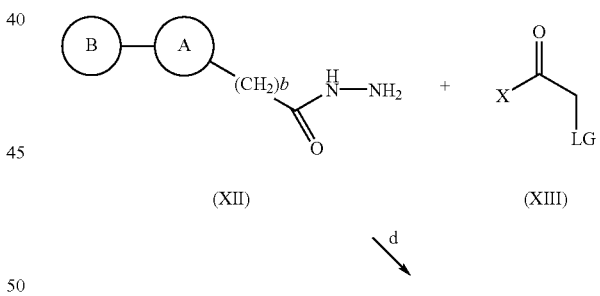

(XII)      (XIII)

↓ d

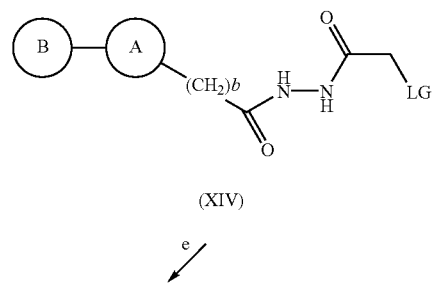

(XIV)

↙ e

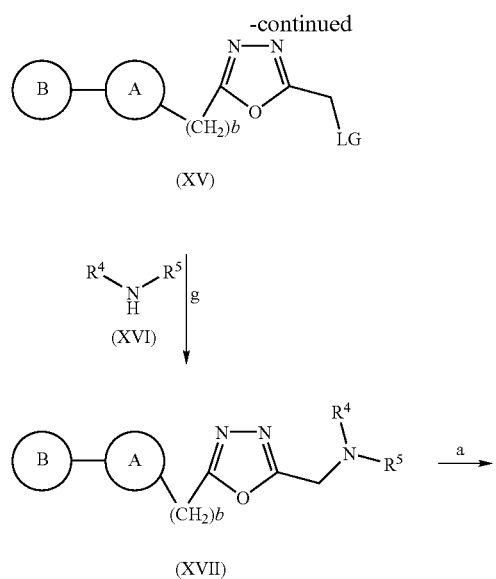

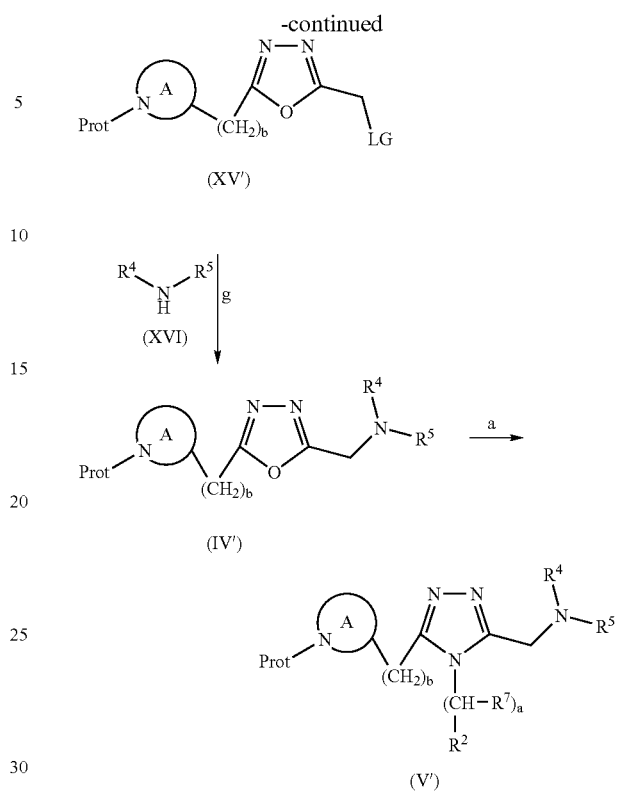

X is OH or Cl.

LG is a leaving group, typically halo, and preferably chloro or bromo

Compounds suitable for use as compound (XIII) and (XVI) are commercially available or are known in the literature.

Step (d): Coupling of compound (XIII) with hydrazide (XII/XII') may be carried out using standard methodology as outlined above.

Step (e): Dehydration and cyclisation of compound (XIV/XIV') to give oxadiazole (XV/XV') is achieved by the methodology outlined above.

Step (g): Compound (XV/XV') is reacted with amine (XVI) to give compound (XVII/IV') in the presence of an excess of base, such as triethylamine, Hünig's base or potassium carbonate as proton acceptor. In a suitable high boiling solvent such as Toluene or DMF at temperatures from 50° C. to 100° C. for 1 to 24 hours.

Alternatively a palladium catalysed cross-coupling reaction can be carried out using a suitable base (t-BuONa), a catalytic amount of a suitable additive such as tri n-butyl phosphine and a suitable palladium catalyst in toluene at reflux from 12 to 24 hours under an inert atmosphere.

Preferred conditions are: 1 eq. of amine, 2 eq. of potassium carbonate in DMF at 60° C. for 3 hours.

Step (a): Amination of compound (XVII/IV') to give compound (I/V') is carried out using the methodology outlined above.

It will be appreciated by those skilled in the art that when appropriate the order of steps (a) and (g) may be reversed.

X is OH or Cl.

LG is a leaving group, typically halo, and preferably chloro or bromo

Scheme 6.2

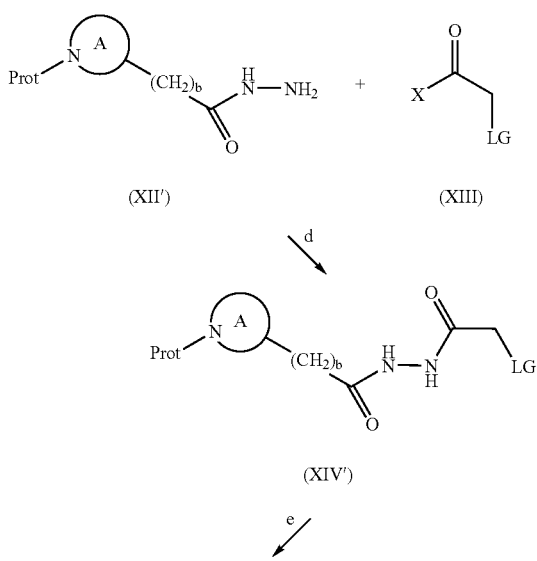

Compounds (V') may be converted to compounds of formula (I) according to the reactions shown in scheme 2.

It will be apparent to those skilled in the art that sensitive functional groups may need to be protected and deprotected during synthesis of a compound of formula (I/I'). This may be achieved by conventional techniques, for example as described in "Protective Groups in Organic Synthesis" by T W Greene and P G M Wuts, John Wiley and Sons Inc, 1991.

In accordance with the present invention there is further provided a novel intermediate of formula (II):

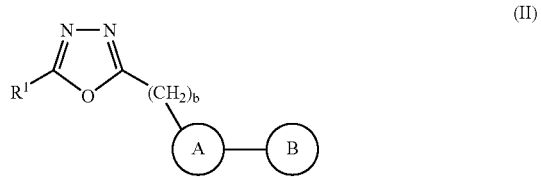

wherein $R^1$, rings A and B, and b are as defined above.

The compounds of the present invention are useful because they possess pharmacological activity in animals. In particular they are V1a receptor antagonists and so are useful in the treatment of a number of conditions including aggression, Alzheimer's disease, anorexia nervosa, anxiety disorder, asthma, atherosclerosis, cardiac failure, cardiovascular disease, cataract, central nervous system disease, cerebrovascular ischemia, cirrhosis, cognitive disorder, Cushing's disease, depression, diabetes mellitus, dysmenorrhoea, edema, emesis, endometriosis, gastrointestinal disease, glaucoma, gynaecological disease, heart disease, hypertension, hyponatremia, intrauterine growth retardation, ischemia, ischemic heart disease, lung tumor, micturition disorder, mittleschmerz, motion sickness, neoplasm, nephrotoxicity, non-insulin dependent diabetes, obesity, obsessive/compulsive disorder, ocular hypertension, premature ejaculation, premature labor, pulmonary disease, Raynaud's disease, renal disease, renal failure, male and female sexual dysfunction, sleep disorder, spinal cord injury, thrombosis, urogenital tract infection, urolithiasis. Particularly of interest is dysmenorrhoea.

Thus, according to another aspect of the invention, there is provided a method of treatment of dysmenorrhoea which comprises administering a therapeutically effective amount of a compound of the invention to a patient suffering from such a disorder. The use of the compounds as a medicament and the use of the compounds of the present invention in the manufacture of a medicament for the treatment of aggression, Alzheimer's disease, anorexia nervosa, anxiety disorder, asthma, atherosclerosis, cardiac failure, cardiovascular disease, cataract, central nervous system disease, cerebrovascular ischemia, cirrhosis, cognitive disorder, Cushing's disease, depression, diabetes mellitus, dysmenorrhoea, edema, emesis, endometriosis, gastrointestinal disease, glaucoma, gynaecological disease, heart disease, hypertension, hyponatremia, intrauterine growth retardation, ischemia, ischemic heart disease, lung tumor, micturition disorder, mittleschmerz, motion sickness, neoplasm, nephrotoxicity, non-insulin dependent diabetes, obesity, obsessive/compulsive disorder, ocular hypertension, premature ejaculation, premature labor, pulmonary disease, Raynaud's disease, renal disease, renal failure, male and female sexual dysfunction, sleep disorder, spinal cord injury, thrombosis, urogenital tract infection, urolithiasis, particularly dysmenorrhoea, are also provided.

The compounds of the present invention may be administered by any convenient route, for example orally, parenterally (e.g. intravenously, transdermally), or rectally. The daily dose required will, of course, vary with the particular compound used, the particular condition being treated and with the severity of that condition. However, in general a total daily dose of from about 0.01 to about 15 mg/kg of body weight, and preferably about 0.1 to about 5 mg/kg, is suitable, administered from 1 to 3 times daily. Oral administration is of particular interest.

The compounds of the present invention will generally be administered in the form of a pharmaceutical formulation. Thus, according to another aspect of the present invention, there is provided a pharmaceutical formulation comprising a compound of formula (I) in admixture with a pharmaceutically acceptable adjuvant, diluent or carrier. The pharmaceutical formulation is preferably in unit dose form. Such forms include solid dosage forms, for example tablets, pills, capsules, powders, granules and suppositories for oral, parenteral or rectal administration, and liquid dosage forms, for example sterile parenteral solutions or suspensions, suitably flavoured syrups, flavoured emulsions with edible oils such as cottonseed oil, sesame oil, coconut oil and peanut oil, and elixirs and similar pharmaceutical vehicles.

Solid formulations may be prepared by mixing the active ingredient with pharmaceutical carriers, for example conventional tabletting ingredients such as corn starch, lactose, sucrose, sorbitol, talc, stearic acid, magnesium stearate, dicalcium phosphate, gums and other diluents, for example water, to form a homogeneous preformulation formulation in which the active ingredient is uniformly dispersed so that it may be readily subdivided into equally effective unit dosage forms containing typically from 0.1 to 500 mg of the active ingredient. The solid dosage forms may be coated or otherwise compounded to prolong the action of the formulation.

The compounds of he present invention may be administered in combination with an oral contraceptive. The compounds of the present invention may be administered in combination with a PDE5 inhibitor. The compounds of the present invention may be administered in combination with an NO donor. The compounds of the present invention may be administered in combination with L-arginine, or as an arginate salt.

The compounds of the present invention may be tested in the screens set out below:

1.0 $V_{1A}$ Filter Binding Assay 1.1 Membrane Preparation

Receptor binding assays were performed on cellular membranes prepared from CHO cells stably expressing the human $V_{1A}$ receptor, (CHO-h$V_{1A}$). The CHO-h$V_{1A}$ cell line was kindly provided under a licensing agreement by Marc Thibonnier, Dept. of Medicine, Case Western Reserve University School of Medicine, Cleveland, Ohio. CHO-h$V_{1A}$ cells were routinely maintained at 37° C. in humidified atmosphere with 5% $CO_2$ in DMEM/Hams F12 nutrient mix supplemented with 10% fetal bovine serum, 2 mM L-glutamine, 15 mM HEPES and 400 µg/ml G418. For bulk production of cell pellets, adherent CHO-h$V_{1A}$ cells were grown to confluency of 90–100% in 850 $cm^2$ roller bottles containing a medium of DMEM/Hams F12 Nutrient Mix supplemented with 10% fetal bovine serum, 2 mM L-glutamine and 15 mM HEPES. Confluent CHO-h$V_{1A}$ cells were washed with phosphate-buffered saline (PBS), harvested into ice cold PBS and centrifuged at 1,000 rpm.

Cell pellets were stored at −80° C. until use. Cell pellets were thawed on ice and homogenised in membrane preparation buffer consisting of 50 mM Tris-HCl, pH 7.4, 5 mM $MgCl_2$ and supplemented with a protease inhibitor cocktail, (Roche). The cell homogenate was centrifuged at 1000 rpm, 10 min, 4° C. and the supernatant was removed and stored on ice. The remaining pellet was homogenised and centrifuged as before. The supernatants were pooled and centrifuged at 25,000×g for 30 min at 4° C. The pellet was resuspended in freezing buffer consisting of 50 mM Tris-HCl, pH 7.4, 5 mM $MgCl_2$ and 20% glycerol and stored in small aliquots at −80° C. until use. Protein concentration was determined using Bradford reagent and BSA as a standard.

1.2 $V_{1A}$ Filter Binding

Protein linearity followed by saturation binding studies were performed on each new batch of membrane. Membrane concentration was chosen that gave specific binding on the linear portion of the curve. Saturation binding studies were then performed using various concentrations of [$^3$H]-arginine vasopressin, [$^3$H]-AVP (0.05 nM–100 nM) and the $K_d$ and $B_{max}$ determined.

Compounds were tested for their effects on [$^3$H]-AVP binding to CHO-h$V_{1A}$ membranes, ($^3$H-AVP; specific activity 65.5 Ci/mmol; NEN Life Sciences). Compounds were solubilised in dimethylsulfoxide (DMSO) and diluted to working concentration of 10% DMSO with assay buffer containing 50 mM Tris-HCL pH 7.4, 5 mM $MgCl_2$ and 0.05% BSA. 25 µl compound and 25 µl [$^3$H]-AVP, (final concentration at or below $K_d$ determined for membrane batch, typically 0.5 nM–0.6 nM) were added to a 96-well round bottom polypropylene plate. The binding reaction was initiated by the addition of 200 µl membrane and the plates were gently shaken for 60 min at room temperature. The reaction was terminated by rapid filtration using a Filtermate Cell Harvester (Packard Instruments) through a 96-well GF/B UniFilter Plate which had been presoaked in 0.5% polyethyleneimine to prevent peptide sticking. The filters were washed three times with 1 ml ice cold wash buffer containing 50 mM Tris-HCL pH 7.4 and 5 mM $MgCl_2$. The plates were dried and 50 µl Microscint-0 (Packard instruments) was added to each well. The plates were sealed and counted on a TopCount Microplate Scintillation Counter (Packard Instruments). Non-specific binding (NSB) was determined using 1 µM unlabelled d(CH2)5Tyr(Me)AVP ([β-mercapto-β,β-cyclopentamethylenepropionyl,0-Me-Tyr$^2$,Arg$^8$]-vasopressin) (βMCPVP), (Sigma). The radioligand binding data was analysed using a four parameter logistic equation with the min forced to 0%. The slope was free fitted and fell between −0.75 and −1.25 for valid curves. Specific binding was calculated by subtracting the mean NSB cpm from the mean Total cpm. For test compounds the amount of ligand bound to the receptor was expressed as % bound=(sample cpm−mean NSB cpm)/specific binding cpm ×100. The % bound was plotted against the concentration of test compound and a sigmoidal curve was fitted. The inhibitory dissociation constant ($K_i$) was calculated using the Cheng-Prusoff equation: $K_i=IC_{50}/(1+[L]/K_d)$ where [L] is the concentration of ligand present in the well and $K_d$ is the dissociation constant of the radioligand obtained from Scatchard plot analysis.

2.0 $V_{1A}$ Functional Assay; Inhibition of AVP/$V_{1A}$-R Mediated $Ca^{2+}$ Mobilization by FLIPR (Fluorescent Imaging Plate Reader) (Molecular Devices)

Intracellular calcium release was measured in CHO-h$V_{1A}$ cells using FLIPR, which allows the rapid detection of calcium following receptor activation. The CHO-h$V_{1A}$ cell line was kindly provided under a licensing agreement by Marc Thibonnier, Dept. of Medicine, Case Western Reserve University School of Medicine, Cleveland, Ohio. CHO-$V_{1A}$ cells were routinely maintained at 37° C. in humidified atmosphere with 5% $CO_2$ in DMEM/Hams F12 nutrient mix supplemented with 10% fetal bovine serum, 2 mM L-glutamine, 15 mM HEPES and 400 µg/ml G418. On the afternoon before the assay cells were plated at a density of 20,000 cells per well into black sterile 96-well plates with clear bottoms to allow cell inspection and fluorescence measurements from the bottom of each well. Wash buffer containing Dulbecco's phosphate buffered saline (DPBS) and 2.5 mM probenecid and loading dye consisting of cell culture medium containing 4 µM Fluo-3-AM (dissolved in DMSO and pluronic acid), (Molecular Probes) and 2.5 mM probenecid was prepared fresh on the day of assay. Compounds were solubilised in DMSO and diluted in assay buffer consisting of DPBS containing 1% DMSO, 0.1% BSA and 2.5 mM probenecid. The cells were incubated with 100 µl loading dye per well for 1 hour at 37° C. in humidified atmosphere with 5% $CO_2$. After dye loading the cells were washed three times in 100 µl wash buffer using a Denley plate washer. 100 µl wash buffer was left in each well. Intracellular fluorescence was measured using FLIPR. Fluorescence readings were obtained at 2 s intervals with 50 µl of the test compound added after 30 s. An additional 155 measurements at 2 s intervals were then taken to detect any compound agonistic activity. 50 µl of arginine vasopressin (AVP) was then added so that the final assay volume was 200 µl. Further fluorescence readings were collected at 1 s intervals for 120 s. Responses were measured as peak fluorescence intensity (FI). For pharmacological characterization a basal FI was subtracted from each fluorescence response. For AVP dose response curves, each response was expressed as a % of the response to the highest concentration of AVP in that row. For $IC_{50}$ determinations, each response was expressed as a % of the response to AVP. IC50 values were converted to a modified $K_b$ value using the Cheng-Prusoff equation which takes into account the agonist concentration, [A], the agonist $EC_{50}$ and the slope: $K_b=IC_{50}/(2+[A]/A_{50}]^n)^{1/n}-1$ where [A] is the concentration of AVP, $A_{50}$ is the $EC_{50}$ of AVP from the dose response curve and n=slope of the AVP dose response curve.

The compounds of the invention have the advantage that they are more potent, have a longer duration of action, have a broader range of activity, are more stable, have fewer side effects or are more selective, or have other more useful properties than the compounds of the prior art.

Thus the invention provides:

(i) a compound of formula (I) or a pharmaceutically acceptable salt or solvate thereof;

(ii) a process for the preparation of a compound of formula (I) or a pharmaceutically acceptable salt or solvate thereof;

(iii) a pharmaceutical formulation including a compound of formula (I) or a pharmaceutically acceptable salt or solvate thereof, together with a pharmaceutically acceptable excipients, diluent or carrier;

(iv) a compound of formula (I) or a pharmaceutically acceptable salt, solvate or composition thereof, for use as a medicament;

(v) the use of a compound of formula (I) or of a pharmaceutically acceptable salt, solvate or composition thereof, for the manufacture of a medicament for the treatment of aggression, Alzheimer's disease, anorexia nervosa, anxiety disorder, asthma, atherosclerosis, cardiac failure, cardiovascular disease, cataract, central nervous system disease, cerebrovascular ischemia, cirrhosis, cognitive disorder, Cushing's disease, depression, diabetes mellitus, dysmenorrhoea, edema, emesis, endometriosis, gastrointestinal disease, glaucoma, gynaecological disease, heart disease, hypertension, hyponatremia, ischemia, ischemic heart disease, intrauterine growth retardation, lung tumor, micturition disorder, motion sickness, mittleschmerz, neoplasm, nephrotoxicity, non-insulin dependent diabetes, obesity, obsessive/compulsive disorder, ocular hypertension, premature ejaculation, premature labor, pulmonary disease, Raynaud's disease, renal disease, renal failure, male and female sexual dysfunction, sleep disorder, spinal cord injury, thrombosis, urogenital tract infection, urolithiasis;

(vi) use as in (v) where the disease or disorder is dysmenorrhoea;

(vii) a method of treatment of a mammal to treat aggression, Alzheimer's disease, anorexia nervosa, anxiety disorder, asthma, atherosclerosis, cardiac failure, cardiovascular disease, cataract, central nervous system disease, cerebrovascular ischemia, cirrhosis, cognitive disorder, Cushing's disease, depression, diabetes mellitus, dysmenorrhoea, edema, emesis, endometriosis, gastrointestinal disease, glaucoma, gynaecological disease, heart disease, hypertension, hyponatremia, ischemia, ischemic heart disease, intrauterine growth retardation, lung tumor, micturition disorder, motion sickness, mittleschmerz, neoplasm, nephrotoxicity, non-insulin dependent diabetes, obesity, obsessive/compulsive disorder, ocular hypertension, premature ejaculation, premature labor, pulmonary disease, Raynaud's disease, renal disease, renal failure, male and female sexual dysfunction, sleep disorder, spinal cord injury, thrombosis, urogenital tract infection, urolithiasis including treating said mammal with an effective amount of a compound of formula (I) or with a pharmaceutically acceptable salt, solvate or composition thereof;

(viii) a method as in (vii) where the disease or disorder is dysmenorrhoea;

(ix) a novel intermediate of the formula (II);

(x) the use of a V1a antagonist in combination with an oral contraceptive for the treatment of dysmenorrhoea.

(xi) the use of a combination of a compound of formula (I) with an oral contraceptive for the treatment of dysmenorrhoea.

The invention is illustrated by the following preparations and examples:

PREPARATION 1

3,4,5,6-Tetrahydro-2H-[1,2']bipyridinyl-4-carboxylic acid

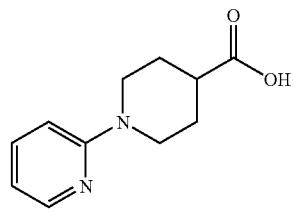

Sodium hydroxide solution (5M, 24.8 ml, 0.12 mol) was added drop wise to a solution of 3,4,5,6-tetrahydro-2H-[1, 2']-bipyridinyl-4-carboxylic acid ethyl ester (5.8 g, 24 mmol)(see reference Farmaco, 1993, 48(10), 1439) in 1,4-dioxane (100 ml). The mixture was stirred at room temperature for 72 hours and then evaporated under reduced pressure. The residue was purified by ion exchange chromatography on Dowex® 50 WX8 resin using methanol and ammonium hydroxide solution in water as eluant (gradient from 0:0:100 to 0:5:95 to 5:5:90). The material obtained was triturated with diethyl ether to give the title compound (4.42 g).

LCMS: m/z ES$^+$ 288 [M+H]$^+$

PREPARATION 2

1-Pyrimidin-2-yl-piperidine-4-carboxylic acid N'-butyryl-hydrazide

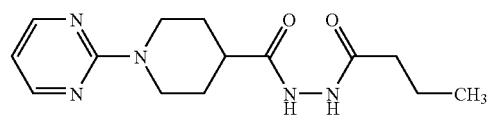

A mixture of 1-pyrimidin-2-yl-piperidine-4-carboxylic acid (3.0 g, 14.5 mmol)(see reference U.S. Pat. No. 4,826, 843), 1-hydroxybenzotriazole hydrate (1.96 g, 14.5 mmol) and 1-(3-dimethylaminopropyl-3-ethylcarbodiimide hydrochloride (2.78 g, 14.5 mmol) in dichloromethane (100 ml) was stirred for 10 minutes. Butyric acid hydrazide (1.78 g, 17.4 mmol) was added and the reaction mixture was stirred under a nitrogen atmosphere for 18 hours. The reaction mixture was diluted with dichloromethane (100 ml) and sodium hydrogen carbonate solution was added. The reaction mixture was concentrated under reduced pressure and the solid formed was isolated by filtration. The material obtained was dried under vacuum at 40° C. to give the title compound (2.62 g).

LCMS: m/z ES$^+$ 314 [M+Na]$^+$

PREPARATIONS 3–11

The compounds of the following tabulated Preparations (Table 1) of the general formula:

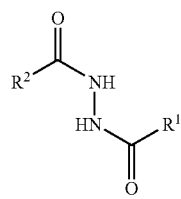

were prepared by a similar method to that of Preparation 2 using the appropriate carboxylic acid and hydrazide.
TABLE 1
| Preparation Number | R¹ | R² |
|---|---|---|
| 3 | 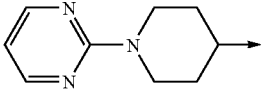 | 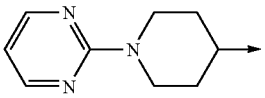 |
| 4 | 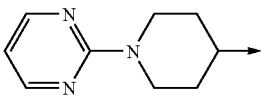 | 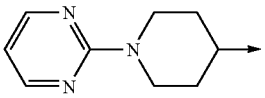 |
| 5 | 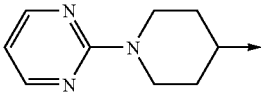 | 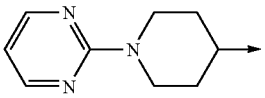 |
| 6 | 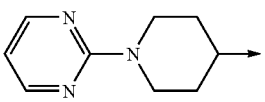 | 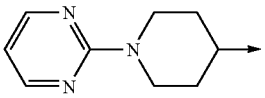 |
| 7 | 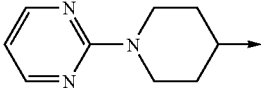 | 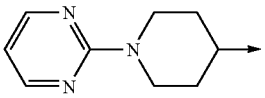 |
| 8 | 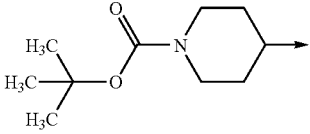 | 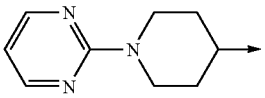 |
| 9 | $CH_3$ | 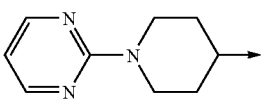 |
| 10 | 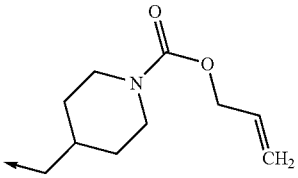 | 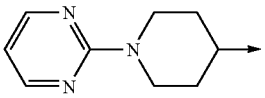 |
| 11[A] | $CH_3$ |  |
[A]See reference WO 9821210 (intermediate 96) for the starting carboxylic acid

PREPARATION 3

LCMS: m/z ES$^+$ 328 [M+Na]$^+$

PREPARATION 4

LCMS: m/z ES$^+$ 314 [M+Na]$^+$

PREPARATION 5

LCMS: m/z ES$^+$ 396 [M+Na]$^+$

PREPARATION 6

LCMS: m/z ES$^+$ 314 [M+Na]$^+$

PREPARATION 7

$^1$H NMR (400 MHz, DMSO-d$_6$): δ 0.69 (m, 4H), 1.58 (m, 6H), 2.93 (m, 2H), 4.62 (d, 2H), 6.59 (t, 1H), 8.34 (d, 2H), 9.67 (s, 1H), 9.94 (s, 1H).

PREPARATION 8

$^1$H NMR (400 MHz, DMSO-d$_6$): δ 1.50 (m, 2H), 1.80 (d, 2H), 2.90 (t, 2H), 4.60 (d, 2H), 4.70 (s, 2H), 6.60 (t, 1H), 6.95 (t, 2H), 7.10 (d, 1H), 7.20 (t, 1H), 7.40 (d, 1H), 8.30 (m, 2H), 10.0 (m, 2H).

PREPARATION 9

$^1$H NMR (400 MHz, DMSO-d$_6$): δ 1.39 (m, 11H), 1.64 (m, 2H), 1.81 (s, 3H), 2.35 (m, 1H), 2.74 (m, 2H), 3.92 (d, 2H), 9.88 (s, 2H).

PREPARATION 10

LCMS: m/z ES$^-$ 320 [M−H]$^-$

PREPARATION 11

LCMS: m/z ES$^+$ 306 [M+Na]$^+$

PREPARATION 12

3,4,5,6-Tetrahydro-2H-[1,2']bipyridinyl-4-carboxylic acid N'-pentanoyl-hydrazide

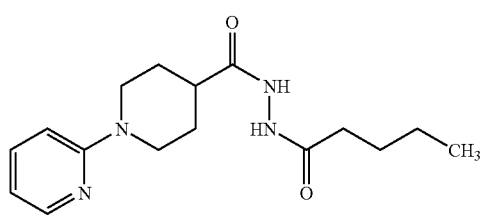

The carboxylic acid from Preparation 1 (1.5 g, 7.3 mmol) was suspended in dichloromethane (40 ml) containing N,N-dimethylformamide (2 drops) and oxalyl chloride (1.27 ml, 14 mmol) in dichloromethane (5 ml) was added drop wise. The mixture was stirred for 5 hours at room temperature and then was evaporated under reduced pressure. The residue was suspended in hexane and evaporated (3×20 ml). The residue was dissolved in dichloromethane and cooled to 0° C. and pentanoic acid hydrazide (1.7 g, 14.6 mmol) was added. 1-Methyl-pyrrolidin-2-one (1.6 ml, 14.6 mmol) in dichloromethane (10 ml) was added drop wise and the mixture was stirred at room temperature for 16 hours. The solvent was evaporated under reduced pressure and the residue was triturated with diethyl ether. The material obtained was dissolved in water and acidified to pH2 by addition of 2N hydrochloric acid. The acidic solution filtered and the filtrate was washed with ethyl acetate (3×20 ml) then basified with sodium carbonate. The solid formed was triturated with diethyl ether and isolated by filtration to give the title compound as a white solid (0.68 g).

LCMS: m/z ES$^-$ 303 [M−H$^-$

PREPARATION 13

3,4,5,6-Tetrahydro-2H-[1,2']bipyridinyl-4-carboxylic acid N'-acetyl-hydrazide

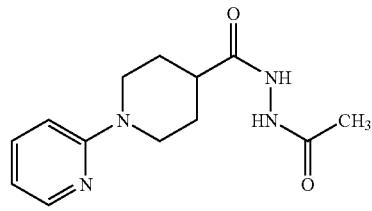

The title compound was obtained from the carboxylic acid of Preparation 1 and acetyl hydrazide in 39% yield following the procedure described in Preparation 12.

APCI MS m/z 263 [M+H]$^+$

PREPARATION 14

3,4,5,6-Tetrahydro-2H-[1,2']bipyridinyl-4-carboxylic acid N'-(2-morpholin-4-yl-acetyl)-hydrazide

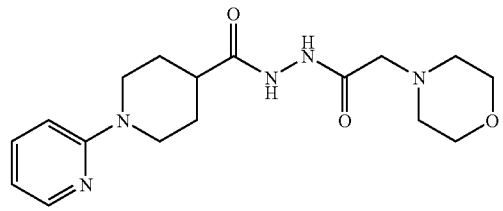

The title compound was obtained from the carboxylic acid of Preparation 1 and morpholin-4-yl-acetic acid hydrazide (see reference Bull. Soc. Chim. Fr. 1962, 250), in 36% yield following the procedure described in Preparation 12.

$^1$H NMR (400 MHz, CDCl$_3$): δ 1.87 (m, 2H), 1.96 (m, 2H), 2.60 (m, 5H), 2.59 (s, 2H), 3.01 (m, 2H), 3.75 (m, 4H), 4.35 (s, 2H), 6.63 (m, 1H), 6.72 (d, 1H), 7.32 (m, 1H), 8.14 (m, 1H), 8.81 (s, 1H), 9.26 (s, 1H).

PREPARATION 15

1-Pyrimidin-2-yl-piperidine-4-carboxylic acid hydrazide hydrochloride

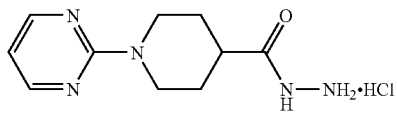

Hydrogen chloride solution in 1,4-dioxane (4M, 75 ml, 0.3 mol) was added to the hydrazone of Preparation 10 (5.5 g, 17 mmol) in methanol (20 ml) at 0° C. The mixture was warmed to room temperature and then was stirred at room temperature for 16 hours.

The solvent was evaporated under reduced pressure to give the title compound as a white solid (3 g)

$^1$H NMR (400 MHz, DMSO-$d_6$): δ 1.57 (m, 2H), 1.83 (d, 2H), 2.70 (m, 1H), 3.08 (t, 2H), 4.64 (d, 2H), 6.78 (t, 1H), 8.47 (d, 2H), 11.35 (s, 1H).

PREPARATION 16

1-Pyrimidin-2-yl-piperidine-4-carboxylic acid N'-isobutyryl-hydrazide

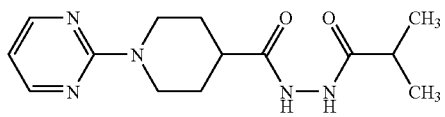

The hydrazide of Preparation 15 (1.5 g, 4.6 mmol) was dissolved in N,N-dimethylformamide (15 ml) containing triethylamine (1.95 ml, 4.6 mmol) and isobutyryl chloride (0.53 ml, 5.1 mmol) was added. The mixture was stirred at room temperature for 16 hours and then at 60° C. for 24 hours. The reaction mixture was cooled to room temperature and partitioned between dichloromethane and water. The organic solution was washed with sodium hydrogen carbonate solution, and brine, then dried over sodium sulphate and evaporated under reduced pressure. The residue was purified by chromatography on silica gel using methanol in dichloromethane as eluant (gradient from 0:100 to 4:96) to give the title compound (300 mg).

LCMS: m/z ES$^+$ 314 [M+Na]$^+$

PREPARATION 17

1-Pyrimidin-2-yl-piperidine-4-carboxylic acid N'-(3-methyl-butyryl)-hydrazide

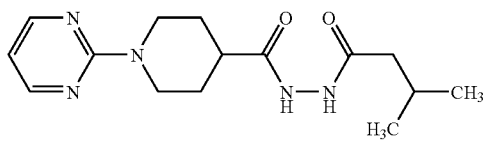

Diisopropylethylamine (10.2 ml, 56.8 mmol) and 3-methylbutyryl chloride (4.62 ml, 38 mmol) were added to a solution of hydrazinecarboxylic acid tert-butyl ester in dichloromethane (50 ml) and the mixture was stirred at room temperature for 18 hours. The reaction mixture was washed with water (100 ml) and the aqueous layer was extracted with dichloromethane (100 ml). The combined organic solutions were washed with sodium hydrogen carbonate solution (50 ml) and brine (50 ml), dried over magnesium sulphate and evaporated under reduced pressure.

The residue was dissolved in dichloromethane (100 ml) and hydrogen chloride (4M solution in 1,4-dioxane) was added. The mixture was stirred at room temperature under a nitrogen atmosphere for 56 hours and the solvent was evaporated under reduced pressure.

The residue was added to a mixture of 1-pyrimidin-2-yl-piperidine-4-carboxylic acid (6.6 g, 31.7 mmol) (see reference U.S. Pat. No. 4,826,843), 1-hydroxybenzotriazole hydrate (4.28 g, 31.7 mmol) and 1-(3-dimethylaminopropyl-3-ethylcarbodiimide hydrochloride (6.09 g, 31.7 mmol) in dichloromethane (50 ml). Diisopropylethylamine (17 ml, 95 mmol) was added and the mixture was stirred for 3 days. The solvent was evaporated and the residue was triturated with water and then with diethyl ether to give the title compound as a white solid (4.49 g).

$^1$H NMR (400 MHz, DMSO-$d_6$): δ 0.90 (s, 6H), 1.50 (m, 2H), 1.74 (m, 2H), 1.99 (m, 2H), 2.99 (m, 4H), 4.61 (d, 2H), 6.59 (t, 1H), 8.34 (d, 2H), 9.59 (d, 1H), 9.67 (d, 1H).

LCMS: m/z ES$^-$ 304 [M–H]$^-$

PREPARATION 18

2-[4-(5-Isobutyl-[1,3,4]oxadiazol-2-yl)-piperidin-1-yl]-pyrimidine

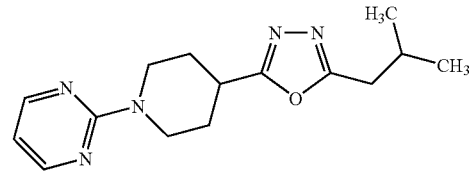

The hydrazide from preparation 17 (4.49 g, 14.7 mmol) was suspended in phosphorus oxychloride (50 ml) at 100° C. under a nitrogen atmosphere for 2 hours. The mixture was cooled and the solvent was evaporated under reduced pressure and the last traces of phosphorus oxychloride were removed by toluene azeotrope. The residue was basified with sodium hydrogen carbonate solution and the aqueous solution was extracted with dichloromethane (2×100 ml). The combined organic layers were washed with brine, dried over magnesium sulphate and evaporated under reduced pressure to give the title compound as a brown oil (4.23 g).

$^1$H NMR (400 MHz, DMSO-$d_6$): δ 0.92 (s, 6H), 1.64 (m, 2H), 2.04 (m, 3H), 2.71 (d, 2H), 3.18 (m, 2H), 3.28 (m, 1H), 4.54 (m, 2H), 6.60 (t, 1H), 8.34 (d, 2H).

LCMS: m/z ES$^+$ 288 [M+H]$^+$

PREPARATIONS 19–30

The compounds of the following tabulated Preparations (Table 2) of the general formula:

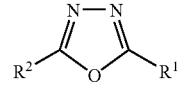

were prepared by a similar method to that of Preparation 18 using the appropriate hydrazide.

TABLE 2

| Preparation Number | R¹ | R² |
|---|---|---|
| 19[a] | 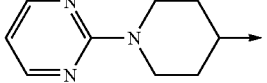 | 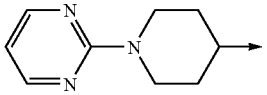 |
| 20[b] | 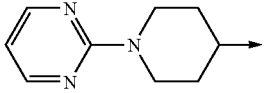 | |
| 21[c] | 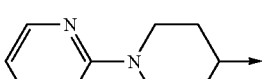 | |
| 22[d] | 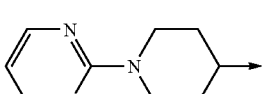 | |
| 23[e] | 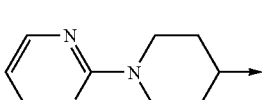 | |
| 24[f] | 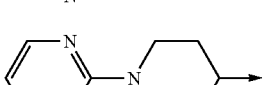 | |
| 25[g] | 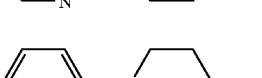 | |
| 26[h] | 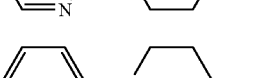 | |
| 27[i] | $CH_3$ | |
| 28[j] | $CH_3$ | 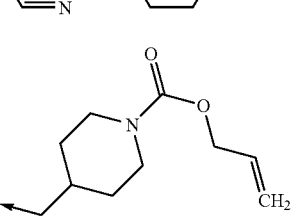 |
| 29[k] | 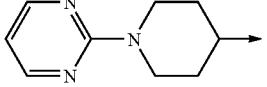 | |

[a] Hydrazide from preparation 3 used as starting material
[b] Hydrazide from preparation 2 used as starting material
[c] Hydrazide from preparation 8 used as starting material
[d] Hydrazide from preparation 7 used as starting material
[e] Hydrazide from preparation 4 used as starting material
[f] Hydrazide from preparation 17 used as starting material
[g] Hydrazide from preparation 5 used as starting material
[h] Hydrazide from preparation 12 used as starting material
[i] Hydrazide from preparation 13 used as starting material
[j] Hydrazide from preparation 11 used as starting material
[k] Hydrazide from preparation 14 used as starting material

PREPARATION 19

APCI MS m/z 288 [M+H]+

PREPARATION 20

LCMS: m/z ES+ 274 [M+H]+

PREPARATION 21

LCMS: m/z ES+ 272,274 [M+H]+

PREPARATION 22

1H NMR (400 MHz, CDCl3): δ 1.08 (m, 4H), 1.86 (m, 2H), 2.11 (m, 2H), 3.18 (m, 3H), 4.72 (m, 2H), 6.50 (t, 1H), 8.33 (d, 2H).

PREPARATION 23

LCMS: m/z ES+ 296 [M+Na]+

PREPARATION 24

LCMS: m/z ES+ 288 [M+H]+

PREPARATION 25

1H NMR (400 MHz, DMSO-d6): δ 1.68 (m, 2H), 2.08 (m, 2H), 3.19 (m, 2H), 4.54 (m, 2H), 5.35 (s, 2H), 6.61 (t, 1H), 7.08 (m, 4H), 8.36 (d, 2H).

PREPARATION 26

LCMS: m/z ES+ 309 [M+Na]+

PREPARATION 27

LCMS: m/z ES+ 267 [M+Na]+

PREPARATION 28

LCMS: m/z ES+ 288 [M+Na]+

PREPARATION 29

APCI MS m/z 330 [M+H]+

PREPARATION 30

2-[4-(5-Methyl-[1,3,4]oxadiazol-2-yl)-piperidin-1-yl]-pyrimidine

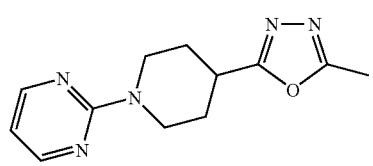

A solution of the hydrazide of preparation 35a (203 mg, 0.92 mmol) and NN-dimethylaminoacetamide dimethylacetal in N,N-dimethylformamide (10 ml) was heated to 50° C. for 2 hr and then evaporated under reduced pressure. The residue was suspended in Xylene (20 ml) and para-toluene sulphonic acid (10 mg) added. The mixture was heated to 150° C. for 18 hr and then evaporated under reduced pressure. The residue was purified by chromatography on silica gel using methanol in dichloromethane as eluant (5:95). The material isolated was triturated with diethyl ether/pentane (1:1) to give the title compound as a buff solid (205 mg).

1H NMR (400 MHz, CDCl3): δ 1.87 (m, 2H), 2.16 (m, 2H), 2.51 (s, 3H), 3.18 (m, 3H), 4.76 (m, 2H), 6.50 (t, 1H), 8.31 (d, 2H).

LCMS: m/z ES+ 246 [M+Na]+

PREPARATION 31

4-(4-Benzyl-5-methyl-4H-[1,2,4]triazol-3-yl)-piperidine-1-carboxylic acid tert-butyl ester

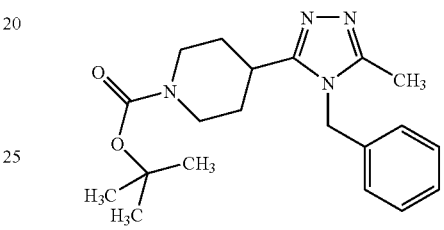

4-(5-Methyl-[1,3,4]oxadiazol-2-yl)-piperidine-1-carboxylic acid tert-butyl ester (5 g, 18.7 mmol) (see reference WO 0039125), benzylamine (2.5 ml, 22 mmol) and magnesium chloride (100 mg) were heated at 150° C. for 1 hour, a further quantity of benzylamine (2.5 ml, 22 mmol) was added and the mixture was heated at 150° C. for 4 hours. The reaction mixture was cooled to room temperature and the reaction mixture was purified by chromatography on silica gel using methanol in dichloromethane as eluant (3:97). The material isolated was triturated with diethyl ether to give the title compound as a white solid (4.69 g).

LCMS: m/z ES+ 379 [M+Na]+

PREPARATION 32

4-(4-Benzyl-5-methyl-4H-[1,2,4]triazol-3-yl)-piperidine hydrochloride

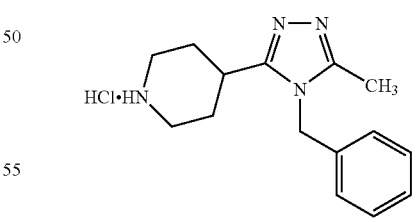

The protected piperidine of Preparation 31 (4.5 g, 12.6 mmol) was added to hydrogen chloride solution in 1,4-dioxane (4M, 80 ml) and the mixture was stirred at 15° C. for 18 hours. The solvent was evaporated and the residue was triturated with diethyl ether to give the title compound as a white solid (3.25 g).

1H NMR (400 MHz, CF3CO2D): δ 2.03 (m, 2H), 2.32 (m, 2H), 2.76 (s, 3H), 3.27 (m, 2H), 3.47 (m, 1H), 3.66 (m, 2H), 5.46 (m, 2H), 7.32 (m, 5H), 11.40 (s, 2H).

PREPARATION 33

4-(5-Methyl-[1,3,4]oxadiazol-2-ylmethyl)-piperidine hydrochloride

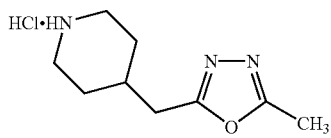

The protected piperidine of Preparation 28 (934 mg, 3.5 mmol) was dissolved in tetrahydrofuran (20 ml) and tris(dibenzylideneacetone)dipalladium (65 mg, 0.18 mmol), 1,4-bis(diphenylphosphino)butane (75 mg, 0.18 mmol) and 2-thiobenzoic acid (1.9 g, 12.3 mmol) were added. The mixture was stirred at room temperature for 20 minutes and then was diluted with ethyl acetate (50 ml). The organic solution was acidified with 2M hydrochloric acid and was extracted with 2M hydrochloric acid (50 ml). The acidic solution was washed with ethyl acetate and then freeze dried to give the title compound as a white foam 900 mg).

$^1$H NMR (400 MHz, DMSO-d$_6$): δ 1.46 (m, 2H), 1.79 (m, 2H), 2.04 (m, 1H), 2.45 (s, 3H), 2.79 (d, 2H), 2.85 (m, 2H), 3.20 (m, 2H), 8.76 (s, 1H), 9.05 (s, 1H).

PREPARATION 34

2-[4-(5-Methyl-[1,3,4]oxadiazol-2-ylmethyl)-piperidin-1-yl]-pyrimidine

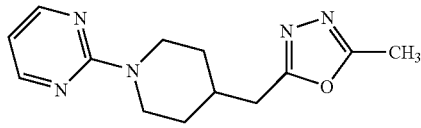

The piperidine from Preparation 33 (766 mg, 3.52 mmol) was dissolved in N,N-dimethylformamide (10 ml) and 2-chloropyrimidine (510 mg, 3.52 mmol) and potassium carbonate (1.46 g, 10.6 mmol) were added. The mixture was heated to 100° C. for 4 hours and then was cooled to room temperature. Ethyl acetate (50 ml) was added and the mixture was washed with water and brine, then dried over magnesium sulphate and evaporated under reduced pressure. The material obtained was recrystallised from ethyl acetate/methanol and the residue was purified by chromatography on silica gel using methanol in dichloromethane as eluant (gradient from 0:100 to 1:99) to give the title compound as a white solid (310 mg).

APCI MS m/z 260 [M+H]$^+$

PREPARATION 35

3,4,5,6-Tetrahydro-2H-[1,2']bipyridinyl-4-carboxylic acid hydrazide

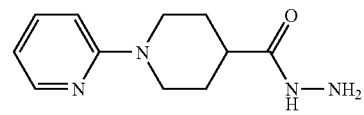

3,4,5,6-Tetrahydro-2H-[1,2']bipyridinyl-4-carboxylic acid ethyl ester (1 g, 4.3 mmol)(see reference Farmaco, 1993, 48(10), 1439) was dissolved in methanol (20 ml) containing hydrazine hydrate (620 µl, 20 mmol) and was heated under reflux for 18 hours. The mixture was cooled to room temperature and evaporated under reduced pressure. The solid formed was triturated with propan-2-ol to give the title compound as a white solid (493 mg).

APCI MS m/z 221 [M+H]$^+$

PREPARATION 35a

1-Pyrimidin-2-yl-piperidine-4-carboxylic acid hydrazide

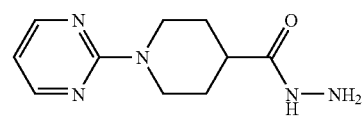

The title compound was obtained from 1-Pyrimidin-2-yl-piperidine-4-carboxylic acid ethyl ester (see Farmaco, 1993, 48(10), 1439) in 91% yield following the procedure described in preparation 35.

APCI MS m/z 222 [M+H]$^+$

PREPARATION 36

3,4,5,6-Tetrahydro-2H-[1,2']bipyridinyl-4-carboxylic acid N'-(2-benzyloxyacetyl)-hydrazide

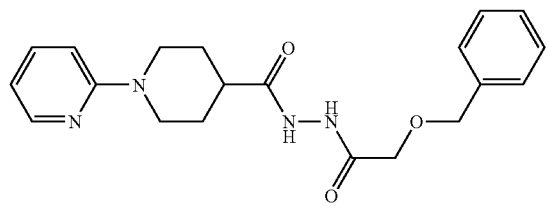

The hydrazide from preparation 35 (190 mg, 8.6 mmol) was suspended in dichloromethane containing 4-methymorpholine (136 µl, 1.5 mmol) and bezyloxyacetyl chloride (136 µl, 8.6 mmol) in dichloromethane (2 ml) was added drop wise. The mixture was stirred at room temperature for 1 hour and then was diluted with dichloromethane (50 ml). The organic solution was washed with water (50 ml) dried over magnesium sulphate ad evaporated under reduced pressure to give the title compound as a cream solid (285 mg).

APCI MS m/z 369 [M+H]$^+$

PREPARATION 37

4-(5-Benzyloxymethyl-[1,3,4]oxadiazol-2-yl)-3,4,5,6-tetrahydro-2H-[1,2']bipyridinyl

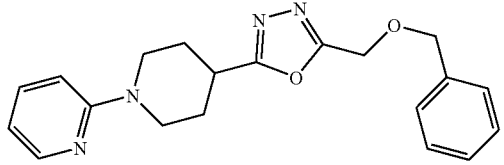

The hydrazide from preparation 36 (260 mg, 0.7 mmol) was mixed with 1,1,1,3,3,3-hexamethyldisylazane (268 µl, 12.7 mmol), tetrabutyl ammonium fluoride trihydrate (22 mg, 0.07 mmol) and imidazole (20 mg) in chlorobenzene (5 ml). The mixture was heated at 150° C. for 16 hours and then evaporated under reduced pressure. The residue was purified by chromatography on silica gel using ethyl acetate as eluant to give the title compound (140 mg).

APCI MS m/z 350 [M+H]$^+$

PREPARATION 38

3,4,5,6-Tetrahydro-2H-[1,2']bipyridinyl-4-carboxylic acid N'-(2-chloroacetyl)-hydrazide

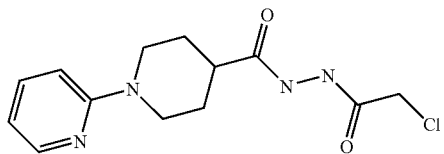

The hydrazide of Preparation 35 (23.6 g, 0.11 mol) was suspended in dichloromethane (500 ml) and 4-methylmorpholine (17.7 ml, 0.16 mol) was added. The mixture was cooled using an ice bath and chloroacetyl chloride (12.8 ml, 0.16 mol) was added drop wise. The reaction was warmed to room temperature and was stirred for 3 hours. The solid formed was isolated by filtration washed with dichloromethane and diethyl ether and dried under vacuum to give the title compound (20.4 g).

LCMS: m/z ES$^+$ 297 [M+H]$^+$

PREPARATION 38a

1-Pyrimidin-2-yl-piperidine-4-carboxylic acid N'-(2-chloro-acetyl)-hydrazide

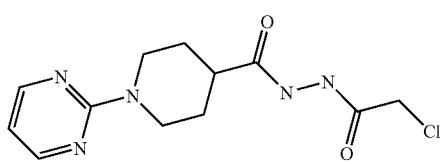

The title compound was prepared from the hydrazide of preparation 35a and chloroacetyl chloride, in 96% yield, using the procedure described in preparation 38.

APCI MS m/z 298 [M+H]$^+$

PREPARATION 39

4-(5-Chloromethyl-[1,3,4]oxadiazol-2-yl)-3,4,5,6-tetrahydro-2H-[1,2']bipyridinyl

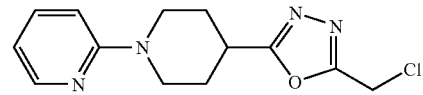

The hydrazide of Preparation 38 (20.4 g, 69 mmol) was suspended in phosphorus oxychloride (150 ml) at 100° C. for 4 hours. The mixture was cooled and the solvent was evaporated under reduced pressure. The residue was dissolved in ethyl acetate and was added to water. The aqueous layer was basified by addition of solid sodium hydrogen carbonate and the phases were separated. The aqueous phase was extracted with ethyl acetate (×2) and the combined organic layers were dried over magnesium sulphate and evaporated under reduced pressure. The material isolated was triturated with diethyl ether to give the title compound as a beige solid (15 g).

$^1$H NMR (400 MHz, CD$_3$OD): δ 1.91 (m, 2H), 2.19 (m, 2H), 3.14 (m, 2H), 3.30 (m, 1H), 4.29 (m, 2H), 4.86 (s, 2H), 6.69 (m, 1H), 6.89 (d, 1H), 7.58 (m, 1H), 8.08 (d, 1H)

PREPARATION 39a

2-[4-(5-Chloromethyl-[1,3,4]oxadiazol-2-yl)-piperidin-1-yl]-pyrimidine

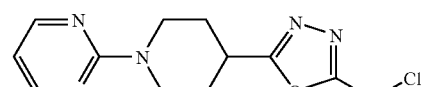

The title compound was prepared from the hydrazide of preparation 38a, in 84% yield, using the procedure described in preparation 39.

APCI MS m/z 280 [M+H]$^+$

PREPARATION 40

4-(5-Piperidin-1-ylmethyl-[1,3,4]oxadiazol-2-yl)-3,4,5,6-tetrahydro-2H-[1,2']bipyridinyl

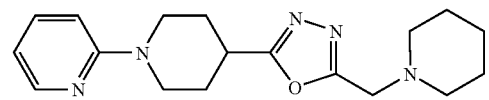

The chloromethyl compound of Preparation 39 (0.5 g, 1.8 mmol) was added to piperidine (0.18 ml, 1.8 mmol) and potassium carbonate (0.5 g, 3.6 mmol) in N,N-dimethylformamide (8 ml) and the mixture was heated at 60° C. for 3 hours. The reaction mixture was evaporated under reduced pressure and the residue was partitioned between water and ethyl acetate. The organic solution was washed with water and then with 2N hydrochloric acid and the combined aqueous solutions were basified with solid sodium hydrogen carbonate. The aqueous mixture was extracted with ethyl acetate (×3) and the combined organic layers were dried over magnesium sulphate and evaporated under reduced pressure. The residue was purified by chromatography on silica gel using methanol and ammonium hydroxide in dichloromethane as eluant (2:0.25:98) to give the title compound as a pale pink solid (0.48 g).

LCMS: m/z ES+ 328 [M+H]+

PREPARATIONS 41–42

The compounds in Table 3 having the general formula:

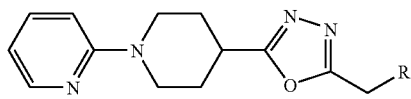

were prepared by a similar method to that described in Preparation 40, using the product of Preparation 39 and an appropriate amine.

TABLE 3

| Preparation number | R |
|---|---|
| 41 | ![structure] |
| 42 | ![structure] |

PREPARATION 41

$^1$H NMR (400 MHz, CD$_3$OD): δ 1.61 (m, 2H), 1.91 (m, 4H), 2.18 (m, 2H), 2.39 (m, 2H), 2.80 (m, 2H), 3.12 (m, 2H), 3.30 (m, 5H), 3.82 (s, 2H), 4.29 (m, 2H), 6.66 (m, 1H), 6.87 (d, 1H), 7.57 (m, 1H), 8.08 (m, 1H)

PREPARATION 42

$^1$H NMR (400 MHz, CD$_3$OD): δ 1.48 (m, 2H), 2.15 (m, 2H), 2.54 (m, 4H), 3.08 (m, 2H), 3.24 (m, 1H), 3.50 (s, 2H), 3.84 (s, 2H), 4.25 (m, 2H), 5.09 (s, 2H), 6.65 (m, 1H), 6.84 (d, 1H), 7.35 (m, 5H), 8.05 (m, 1H)

PREPARATION 43

4-[5-(2-Morpholin-4-yl-ethoxymethyl)-[1,3,4]oxadiazol-2-yl]-3,4,5,6-tetrahydro-2H-[1,2']bipyridinyl

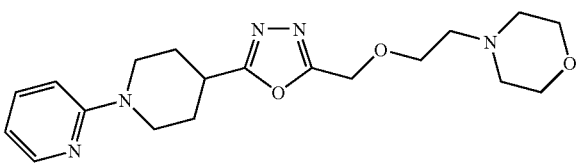

2-Morpholin-4-yl-ethanol (313 μl, 2.6 mmol) in tetrahydrofuran (2 ml) was added to a suspension of sodium hydride (60% in mineral oil, 103 mg, 2.6 mmol) in tetrahydrofuran (2 ml) and the mixture was stirred at room temperature for 1 hour. A suspension of the chloromethyl compound of Preparation 39 (600 mg, 2.16 mmol) in tetrahydrofuran (10 ml) was added in 4 aliquots and the mixture was stirred at room temperature for 16 hours. Ethyl acetate (100 ml) was added and the solution was extracted with water (100 ml). The aqueous solution was washed with ethyl acetate (2×100 ml) and the combined organic layers were dried over magnesium sulphate and evaporated under reduced pressure. The residue was purified by chromatography on silica gel using methanol and ammonium hydroxide in dichloromethane as eluant (5:0.5:95) to give the title compound (500 mg).

$^1$H NMR (400 MHz, CD$_3$OD): δ 1.85 (m, 2H), 2.17 (m, 2H), 2.52 (m, 4H), 2.62 (t, 2H), 3.11 (m, 2H), 3.30 (m, 1H), 3.68 (m, 4H), 3.73 (m, 2H), 4.28 (m, 2H), 4.72 (s, 2H), 6.66 (m, 1H), 6.85 (d, 1H), 7.55 (m, 1H), 8.06 (m, 1H)

PREPARATION 44

3-Oxo-3-[N'-(3,4,5,6-tetrahydro-2H-[1,2']bipyridinyl-4-carbonyl)-hydrazino]-propionic acid tert-butyl ester

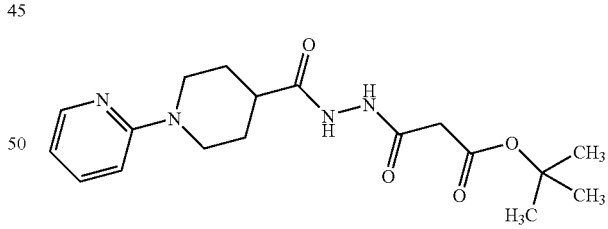

A mixture of the hydrazine from preparation 35 (2.2 g, 10 mmol), tert-butyl malonate (1.6 g, 10 mmol), 1-hydroxybenzotriazole hydrate (2.02 g, 15 mmol), triethylamine (4.8 ml, 20 mmol) and 1-(3-dimethylaminopropyl)-3-ethylcarbodiimide hydrochloride (2.4 g, 12.5 mmol) in dichloromethane (50 ml) was stirred at room temperature for 5 hours. The reaction was diluted with dichloromethane (200 ml), washed with water (150 ml), dried (MgSO$_4$) and evaporated under reduced pressure. The residual oil was purified by column chromatography on silica gel using ethyl acetate as eluant to afford the title compound, as a white solid, 1.4 g.

¹H NMR (CD₃OD, 400 MHz) δ: 1.42 (s, 9H), 1.78 (m, 2H), 1.89 (m, 2H), 2.53 (m, 1H), 2.91 (m, 2H), 3.24 (s, 2H), 4.27 (m, 2H), 6.62 (m, 1H), 6.81 (d, 1H), 7.52 (m, 1H), 8.25 (d, 1H).
LRMS: m/z (APCI⁺) 363 [MH⁺]

PREPARATION 45

[5-(3,4,5,6-Tetrahydro-2H-[1,2′]bipyridinyl-4-yl)-[1,3,4]oxadiazol-2-yl]-acetic acid tert-butyl ester

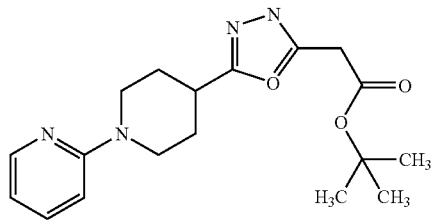

Trifluoroacetic anhydride (1.62 ml, 11.6 mmol) was added drop wise to an ice-cooled solution of the hydrazide from preparation 44 (1.4 g, 3.86 mmol), in dichloromethane (50 ml) and pyridine (1.56 ml, 19.3 mmol), so as to maintain the temperature below 15° C. The reaction was stirred with ice cooling for a further 2 hours, and was then diluted with dichloromethane (50 ml), and washed with 4% aq ammonia. This aqueous wash was extracted with dichloromethane (50 ml), and the combined organic extracts were dried (MgSO₄) and evaporated under reduced pressure to give an oil. This was purified by column chromatography on silica gel using an elution gradient of dichloromethane:ethyl acetate (100:0 to 70:30) to afford the title compound as a yellow oil, 633 mg.
¹H NMR (CD₃OD, 400 MHz) δ: 1.42 (s, 9H), 1.89 (m, 2H), 2.17 (m, 2H), 3.11 (m, 2H), 3.26 (m, 1H), 3.30 (s, 2H), 4.23 (m, 2H), 6.63 (m, 1H), 6.84 (d, 1H), 7.55 (m, 1H), 8.07 (m, 1H).
LRMS: m/z (APCI⁺) 345 [MH⁺]

PREPARATION 46

(3R)-3-Methoxy-pyrrolidine-1-carboxylic acid tert-butyl ester

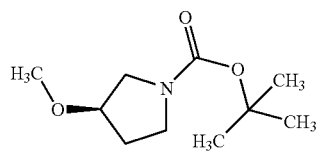

(3R)-3-Hydroxy-pyrrolidine-1-carboxylic acid tert-butyl ester (12.5 g, 66.70 mmol) was dissolved in tetrahydrofuran (334 ml) and the reaction mixture cooled to 0° C. in an ice bath. The reaction mixture was treated with sodium hydride (2.20 g, 80% dispersion in mineral oil, 73.3 mmol) and allowed to warm to room temperature. The reaction mixture was then treated with methyl iodide (14.5 g, 100 mmol) and stirred at room temperature for 18 hours. The reaction mixture was diluted with water (100 ml) and concentrated in vacuo until just the aqueous remained. The aqueous was extracted with ethyl acetate (750 ml), the organic layer separated, dried (MgSO₄) and concentrated in vacuo to yield the title product as a brown oil, 12.48 g.
¹H NMR (CDCl₃, 400 MHz) δ: 1.44 (s, 9H), 1.92 (m, 2H), 3.27 (s, 3H), 3.40 (m, 4H), 3.86 (m, 1H)

PREPARATION 47

(3S)-3-Methoxy-pyrrolidine-1-carboxylic acid tert-butyl ester

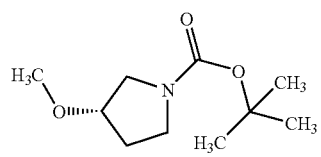

The title product was prepared by a method similar to that described for preparation 46 using (3S)-3-Hydroxy-pyrrolidine-1-carboxylic acid tert-butyl ester.
¹H NMR (CDCl₃, 400 MHz) δ: 1.44 (s, 9H), 1.92 (m, 2H), 3.27 (s, 3H), 3.40 (m, 4H), 3.86 (m, 1H)

PREPARATION 48

(3R)-3-Methoxy-pyrrolidine hydrochloride

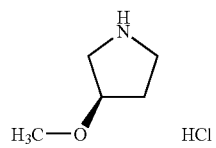

A solution of HCl in dioxan (4M, 13 ml) was added drop wise to an ice-cooled solution of the product of preparation 46 (2.12 g, 10.5 mmol) in dioxan (2 ml). The reaction was allowed to warm to room temperature and stirred for a further 4 hours. The reaction mixture was concentrated under reduced pressure, and the residue azeotroped with ether. The solid was triturated with ether, and the solid filtered off and dried in vacuo to give the product as a brown oil, 1.34 g.

PREPARATION 49

(3S)-3-Methoxy-pyrrolidine hydrochloride

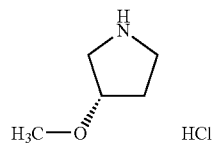

The title product was prepared by a method similar to that described for preparation 48 using the product of preparation 47 as a starting material.

PREPARATIONS 50–57

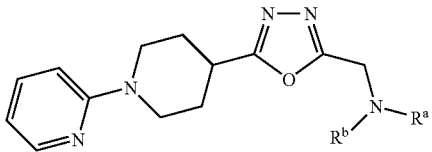

A mixture of the chloride from preparation 39 (1 eq), the amine ($R^aR^bNH$), (1.0–1.5 eq) and potassium carbonate (2–5 eq) in N,N-dimethylformamide (1–5 ml mmol$^{-1}$) was stirred at between 50–100° C. for up to 4 hours. The cooled mixture was concentrated under reduced pressure and the residue partitioned between ethyl acetate and water and the layers separated. The organic phase was dried (MgSO$_4$) and evaporated under reduced pressure. The crude product was purified by column chromatography on silica gel using an elution gradient of pentane:ethyl acetate:methanol (35:65:0 to 0:100:0 to 0:90:10) or dichloromethane:methanol:0.88 ammonia (99:2:0.12 to 96:4:0.25) to give the title compounds.

TABLE 4

| Prep No | NR$^a$R$^b$ | Data |
|---|---|---|
| 50 | NH-CH$_2$CH$_2$-O-CH$_3$ | $^1$H NMR (CD$_3$OD, 400 MHz) δ: 1.82–1.92 (m, 2H), 2.15 (m, 2H), 2.81 (t, 2H), 3.10 (m, 2H), 3.26 (m, 1H), 3.33 (s, 3H), 3.49 (t, 2H), 4.01 (s, 2H), 4.26 (m, 2H), 6.65 (m, 1H), 6.86 (d, 1H), 7.55 (m, 1H), 8.07 (d, 1H). LRMS: m/z (APCl$^+$) 318 [MH$^+$] |
| 51 | NH-CH$_2$CH$_2$CH$_2$-O-CH$_3$ | $^1$H NMR (CD$_3$OD, 400 MHz) δ: 1.73–1.79 (m, 2H), 1.83–1.93 (m, 2H), 2.15 (m, 2H), 2.70 (t, 2H), 3.11 (m, 2H), 3.27 (m, 1H), 3.31 (s, 3H), 3.44 (t, 2H), 3.97 (s, 2H), 4.25 (m, 2H), 6.65 (m, 1H), 6.86 (d, 1H), 7.55 (m, 1H), 8.07 (d, 1H). LRMS: m/z (APCl$^+$) 332 [MH$^+$] |
| 52$^a$ | pyrrolidinyl | $^1$H NMR (CD$_3$OD, 400 MHz) δ: 1.80–1.94 (m, 6H), 2.13–2.20 (m, 2H), 2.65–2.72 (m, 4H), 3.07–3.15 (m, 2H), 3.24–3.29 (m, 1H), 3.93 (m, 2H), 4.26 (m, 2H), 6.65 (dd, 1H), 6.85 (d, 1H), 7.55 (m, 1H), 8.07 (m, 1H). LRMS: m/z (APCl$^+$) 314 [MH$^+$] |
| 53 | 3-hydroxypyrrolidinyl | $^1$H NMR (CD$_3$OD, 400 MHz) δ: 1.71–1.78 (m, 1H), 1.82–1.93 (m, 2H), 2.09–2.20 (m, 3H), 2.60–2.69 (m, 2H), 2.85–2.94 (m, 2H), 3.07–3.15 (m, 2H), 3.23–3.29 (m, 1H), 3.94 (s, 2H), 4.25 (m, 2H), 4.31–4.37 (m, 1H), 6.65 (dd, 1H), 6.85 (d, 1H), 7.54 (m, 1H), 8.07 (d, 1H). LRMS: m/z (APCl$^+$) 330 [MH$^+$] |
| 54$^b$ | (3R)-3-methoxypyrrolidinyl | $^1$H NMR (CD$_3$OD, 400 MHz) δ: 1.80–1.94 (m, 3H), 2.05–2.20 (m, 3H), 2.62–2.68 (m, 1H), 2.73–2.89 (m, 3H), 3.11 (m, 2H), 3.23–3.29 (m, 4H), 4.26 (m, 2H), 6.65 (dd, 1H), 6.86 (d, 1H), 8.07 (d, 1H). LRMS: m/z (APCl$^+$) 344 [MH$^+$] |
| 55$^c$ | (3S)-3-methoxypyrrolidinyl | $^1$H NMR (CD$_3$OD, 400 MHz) δ: 1.80–2.20 (m, 6H), 2.62–2.89 (m, 4H), 3.11 (m, 2H), 3.24–3.29 (m, 4H), 3.92–4.00 (m, 3H), 4.26 (m, 2H), 6.65 (dd, 1H), 6.86 (d, 1H), 7.55 (m, 1H), 8.07 (d, 1H). LRMS: m/z (APCl$^+$) 344 [MH$^+$] |
| 56 | 4-(benzyloxycarbonyl)piperazinyl | $^1$H NMR (CD$_3$OD, 400 MHz) δ: 1.84 (m, 2H), 2.15 (m, 2H), 2.53 (m, 4H), 3.08 (m, 2H), 3.24 (m, 1H), 3.50 (m, 4H), 3.84 (s, 2H), 4.25 (m, 2H), 5.09 (s, 2H), 6.65 (m, 1H), 6.84 (d, 1H), 7.33 (m, 5H), 7.54 (m, 1H), 8.05 (m, 1H). LRMS: m/z (APCl$^+$) 463 [MH$^+$] |

TABLE 4-continued

| Prep No | NR<sup>a</sup>R<sup>b</sup> | Data |
|---|---|---|
| 57<sup>d</sup> | 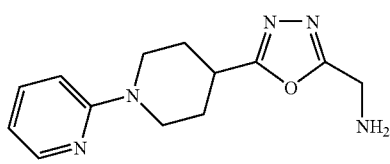 | <sup>1</sup>H NMR (CD<sub>3</sub>OD, 400 MHz) δ: 1.83 (m, 2H), 1.87 (m, 2H), 2.18 (m, 2H), 2.70, 2.95 (2xm, 2H), 3.10 (m, 2H), 3.30 (m, 1H), 3.64 (m, 2H), 4.01 (m, 2H), 4.25 (m, 2H), 4.42 (s, 1H), 6.65 (m, 1H), 6.86 (d, 1H), 7.55 (m, 1H), 8.04 (m, 1H). LRMS: m/z (APCI<sup>+</sup>) 342 [MH<sup>+</sup>] |

$^a$the reaction was performed with pyrrolidine as solvent
$^b$the amine from preparation 49 was used
$^c$the amine from preparation 48 was used
$^d$the HCl salt of the amine was used

PREPARATION 58

C-[5-(3,4,5,6-Tetrahydro-2H-[1,2']bipyridinyl-4-yl)-[1,3,4]oxadiazol-2-yl]-methylamine

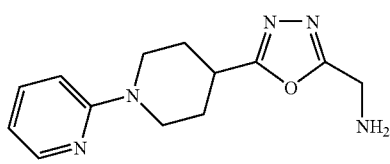

A mixture of the chloride from preparation 39 (2 g, 7.28 mmol) in 0.88 ammonia (100 ml) was heated at 60° C. for 3 hours. The solution was concentrated under reduced pressure to give an orange oil. This was pre-adsorbed onto silica gel and purified by column chromatography on silica gel using an elution gradient of dichloromethane:methanol:0.88 ammonia (98:2:0.25 to 95:5:0.5) to give the title compound as a yellow solid, 1.3 g.

$^1$H NMR (CD$_3$OD, 400 MHz) δ: 1.82–1.94 (m, 2H), 2.15 (m, 2H), 3.06–3.13 (m, 2H), 3.26 (m, 1H), 3.98 (s, 2H), 4.27 (m, 2H), 6.65 (m, 1H), 6.86 (d, 1H), 7.55 (m, 1H), 8.06 (d, 1H).

LRMS: m/z (APCI$^+$) 283 [MH$^+$]

PREPARATION 59

Ethyl-[5-(3,4,5,6-Tetrahydro-2H-[1,2']bipyridinyl-4-yl)-[1,3,4]oxadiazol-2-ylmethyl]-amine

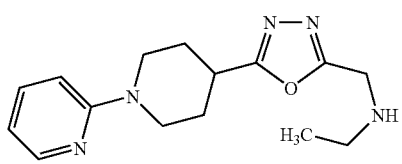

A solution of the chloride from preparation 39 (500 mg, 1.8 mmol) in ethylamine in tetrahydrofuran (5 ml, 2M, 10 mmol) was stirred at 60° C. for 4 hours in a sealed vessel. The solution was evaporated under reduced pressure and the residue was partitioned between dichloromethane and sodium carbonate solution. The layers were separated, the aqueous extracted with further dichloromethane and the combined organic extracts dried (MgSO$_4$) and evaporated under reduced pressure. The residual oil was purified by column chromatography on silica gel using dichloromethane:methanol:0.88 ammonia (99:1:0.25 to 96:4:0.5) as eluant to afford the title compound as a solid.

$^1$H NMR (CD$_3$OD, 400 MHz) δ: 1.13 (t, 3H), 1.85–1.96 (m, 2H), 2.22 (m, 2H), 2.67 (q, 2H), 3.15 (m, 2H), 3.34 (m, 1H), 3.93 (s, 2H), 4.24 (m, 2H), 6.64 (m, 1H), 6.87 (d, 1H), 7.54 (m, 1H), 8.07 (d, 1H).

LRMS: m/z (APCI$^+$) 288 [MH$^+$]

PREPARATION 60

{2-[5-(3,4,5,6-Tetrahydro-2H-[1,2']bipyridinyl-4-yl)-[1,3,4]oxadiazol-2-ylmethoxy]-ethyl}-carbamic acid tert-butyl ester

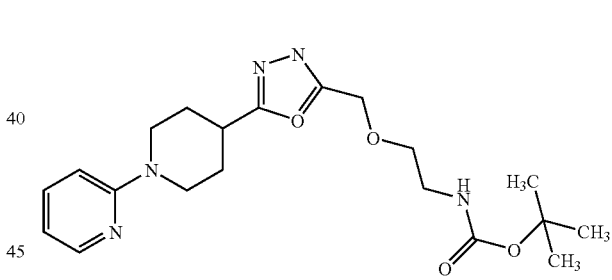

A solution of the tert-butyl N-(2-hydroxyethyl)carbamate (0.42 g, 2.61 mmol) in tetrahydrofuran (2 ml) was added drop wise to a suspension of sodium hydride (103 mg, 60% dispersion in mineral oil, 2.58 mmol) in tetrahydrofuran (2 ml), and the mixture stirred for 30 minutes. A suspension of the chloride from preparation 39 (600 mg, 2.15 mmol) in tetrahydrofuran (10 ml) was added and the reaction stirred at room temperature for 18 hours. The reaction was diluted with ethyl acetate (100 ml) and washed with water (100 ml). The organic solution was dried (MgSO$_4$) and evaporated under reduced pressure. The residue was purified twice by column chromatography on silica gel using dichloromethane:ethyl acetate (50:50) to afford the title compound as a colourless oil, 410 mg.

$^1$H NMR (CD$_3$OD, 400 MHz) δ: 1.43 (s, 9H), 1.90 (m, 2H), 2.18 (m, 2H), 3.10 (m, 2H), 3.17 (t, 2H), 3.25 (m, 1H), 3.52 (t, 2H), 4.26 (m, 2H), 4.70 (s, 2H), 6.64 (m, 1H), 6.83 (d, 1H), 7.53 (m, 1H), 8.04 (m, 1H).

LRMS: m/z (APCI$^+$) 404 [MH$^+$]

PREPARATION 61

[5-(3,4,5,6-Tetrahydro-2H-[1,2']bipyridinyl-4-yl)-[1,3,4]oxadiazol-2-ylmethyl]-carbamic acid tert-butyl ester

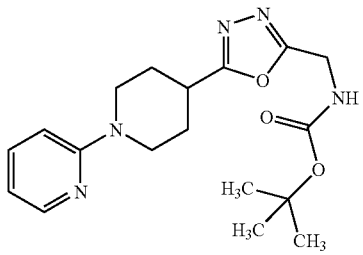

A solution of di-tert-butyl dicarbonate (1.31 g, 6.02 mmol) in dichloromethane (10 ml) was added drop wise to an ice-cooled solution of the amine from preparation 58 (1.3 g, 5.01 mmol) in dichloromethane (15 ml), and once addition was complete the solution was stirred at 0° C. for 10 minutes. The reaction was then allowed to warm to room temperature and stirred for a further 18 hours. The mixture was washed with saturated sodium carbonate solution, dried (MgSO$_4$) and evaporated under reduced pressure. The residual oil was purified by column chromatography on silica gel using an elution gradient of dichloromethane:methanol:0.88 ammonia (100:0:0 to 98:2:0.25). The product was triturated with pentane:ether solution, then evaporated under reduced pressure to give the title compound as a white solid, 1.9 g.

$^1$H NMR (CD$_3$OD, 400 MHz) δ: 1.45 (s, 9H), 1.82–1.92 (m, 2H), 2.13 (m, 2H), 3.08–3.15 (m, 2H), 3.26 (m, 1H), 4.25 (m, 2H), 4.43 (s, 2H), 6.65 (m, 1H), 6.85 (d, 1H), 7.55 (m, 1H), 8.07 (d, 1H); LRMS: m/z (APCI$^+$) 360 [MH$^+$]

PREPARATIONS 62–64

The following compounds of general formula:

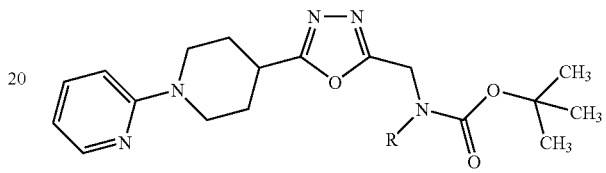

were obtained quantitatively as colourless oils, from the appropriate amines and di-tert-butyl dicarbonate, following a similar procedure to that described in preparation 61.

TABLE 5

| Prep No. | R | Data |
|---|---|---|
| 62[a] | ⌇CH$_3$ | $^1$H NMR (CD$_3$OD, 400 MHz) δ: 1.14 (t, 3H), 1.43 (br s, 9H), 1.82–1.92 (m, 2H), 2.16 (m, 2H), 3.12 (m, 2H), 3.28 (m, 1H), 3.39 (m, 2H), 4.25 (m, 2H), 4.62 (s, 2H), 6.65 (m, 1H), 6.86 (d, 1H), 7.55 (m, 1H), 8.08 (d, 1H). LRMS: m/z (APCI$^+$) 388 [MH$^+$] |
| 63[b] | ⌇O-CH$_3$ | $^1$H NMR (CD$_3$OD, 400 MHz) δ: 1.39–1.46 (m, 9H), 1.81–1.91 (m, 2H), 2.12 (m, 2H), 3.11 (m, 2H), 3.26 (m, 3H), 3.28 (m, 1H), 3.51 (s, 4H), 4.25 (m, 2H), 4.68 (s, 2H), 6.66 (m, 1H), 6.86 (d, 1H), 7.55 (m, 1H), 8.07 (d, 1H). LRMS: m/z (APCI$^+$) 418 [MH$^+$] |
| 64[c] | ⌇O-CH$_3$ | $^1$H NMR (CD$_3$OD, 400 MHz) δ: 1.38–1.51 (m, 9H), 1.78–1.91 (m, 4H), 2.13 (m, 2H), 3.10 (m, 2H), 3.27 (m, 1H), 3.31 (s, 3H), 3.40 (m, 4H), 4.25 (m, 2H), 4.62 (5, 2H), 6.65 (m, 1H), 6.86 (d, 1H), 7.55 (m, 1H), 8.07 (d, 1H). LRMS: m/z (APCI$^+$) 432 [MH$^+$] |

[a]oxadiazole of preparation 59 used as starting material.
[b]oxadiazole of preparation 50 used as starting material.
[c]oxadiazole of preparation 51 used as starting material.

PREPARATION 65

[4-Benzyl-5-(3,4,5,6-tetrahydro-2H-[1,2']bipyridinyl-4-yl)-4H-[1,2,4]triazol-3-ylmethyl]-carbamic acid tert-butyl ester

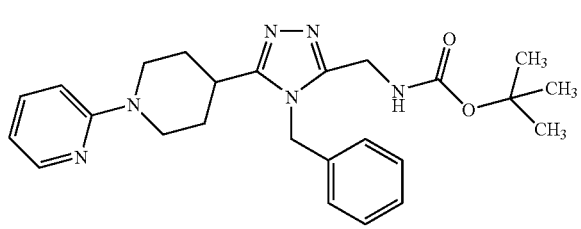

A mixture of the oxadiazole from preparation 61 (900 mg, 2.5 mmol), benzylamine (1.1 ml, 10 mmol), and para-toluenesulphonic acid (90 mg, 0.47 mmol) in xylene (10 ml) was stirred at 150° C. for 18 hours. The cooled mixture was evaporated under reduced pressure and the residue partitioned between dichloromethane and aqueous sodium carbonate solution, and the layers separated. The organic phase was dried (MgSO$_4$) and evaporated under reduced pressure to give an orange oil. This was triturated with ether to afford the title compound as a white solid, 666 mg.

$^1$H NMR (CD$_3$OD, 400 MHz) δ: 1.31 (s, 9H), 1.77–1.87 (m, 2H), 2.74–2.81 (m, 2H), 2.91 (m, 2H), 4.25 (m, 2H), 4.45 (s, 2H), 5.42 (s, 2H), 6.62 (m, 1H), 6.80 (d, 1H), 7.10 (d, 2H), 7.32–7.40 (m, 4H), 7.51 (m, 1H), 8.03 (d, 1H); LRMS: m/z (APCl$^+$) 449 [MH$^+$]

PREPARATIONS 66–68

The title compounds of general formula:

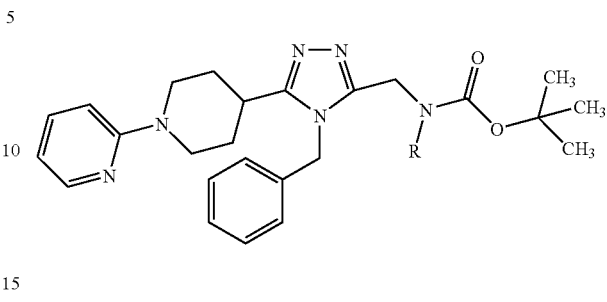

were prepared from the corresponding oxadiazoles and benzylamine, following a similar procedure to that described in preparation 65, except, all products were purified by column chromatography on silica gel using an elution gradient of dichloromethane:methanol:0.88 ammonia (100:0:0 to 95:5:0.5) to give the final products.

TABLE 6

| Prep No. | R | Yield/form | Data |
|---|---|---|---|
| 66[a] | —CH$_3$ (ethyl) | 31% White solid | $^1$H NMR (CD$_3$OD, 400 MHz) δ: 1.10 (t, 3H), 1.31 (s, 9H), 1.72 (m, 2H), 1.82–1.91 (m, 2H), 2.87–3.00 (m, 4H), 3.23 (m, 1H), 4.23 (m, 2H), 4.67 (s, 2H), 5.47 (s, 2H), 6.70 (m, 1H), 6.92 (d, 1H), 7.01 (nr s, 2H), 7.31–7.40 (m, 3H), 7.62 (m, 1H), 8.00 (d, 1H). LRMS: m/z (APCl$^+$) 477 [MH$^+$] |
| 67[b] | —CH$_2$CH$_2$OCH$_3$ | 35% White solid | $^1$H NMR (CD$_3$OD, 400 MHz) δ: 1.29 (s, 9H), 1.71 (m, 2H), 1.83 (m, 2H), 2.86 (m, 2H), 2.94 (m, 1H), 3.30 (s, 3H), 3.36 (m, 2H), 3.51 (t, 2H), 4.24 (m, 2H), 4.74 (s, 2H), 5.43 (s, 2H), 6.63 (m, 1H), 6.81 (d, 1H), 7.04 (m, 2H), 7.36 (m, 3H), 7.52 (m, 1H), 8.03 (d, 1H). LRMS: m/z (APCl$^+$) 507 [MH$^+$] |
| 68[c] | —(CH$_2$)$_3$OCH$_3$ | Quant've White solid | $^1$H NMR (CD$_3$OD, 400 MHz) δ: 1.31 (s, 9H), 1.68–1.90 (m, 6H), 2.79 (m, 2H), 2.91 (m, 1H), 3.28 (m, 2H), 3.31 (s, 3H), 3.37 (t, 2H), 4.25 (m, 2H), 4.65 (s, 2H), 5.44 (s, 2H), 6.62 (m, 1H), 6.80 (d, 1H), 7.01 (m, 2H), 7.31–7.40 (m, 3H), 7.51 (m, 1H), 8.03 (d, 1H). LRMS: m/z (APCl$^+$) 521 [MH$^+$] |

[a] oxadiazole from preparation 62 used as starting material. The product was additionally dissolved in dichloromethane, treated with solid phase isocyanate (12 eq), the mixture stood for 2 hours with occasional stirring, then filtered and evaporated under reduced pressure to give the desired product.
[b] oxadiazole from preparation 63 used as staring material. Product obtained after trituration from ether.
[c] oxadiazole from preparation 64 used as starting material.

PREPARATION 69

{2-[4-Benzyl-5-(3,4,5,6-tetrahydro-2H-[1,2']bipyridinyl-4-yl)-4H-[1,2,4]triazol-3-ylmethoxy]-ethyl}-carbamic acid tert-butyl ester

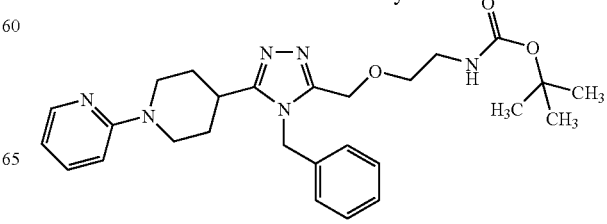

A mixture of the oxadiazole from preparation 60 (200 mg, 0.5 mmol), para-toluene sulphonic acid (20 mg), and benzylamine (162 μl, 1.5 mmol) in xylene (2 ml) was heated at 150° C. for 18 hours. The cooled mixture was evaporated under reduced pressure and the residue purified by column chromatography on silica gel using ethyl acetate:methanol: 0.88 ammonia (100:0:0 to 95:5:0.5). The product was triturated with ether, and the resulting solid filtered off and dried to afford the title compound as a white solid, 120 mg.

$^1$H NMR (CD$_3$OD, 400 MHz) δ: 1.41 (s, 9H), 1.71 (m, 2H), 1.83 (m, 2H), 2.82 (m, 2H), 3.01 (m, 1H), 3.18 (t, 2H), 3.49 (t, 2H), 4.25 (m, 2H), 4.61 (s, 2H), 5.41 (s, 2H), 6.61 (m, 1H), 6.80 (d, 1H), 7.18 (d, 2H), 7.39 (m, 3H), 7.51 (m, 1H), 8.03 (d, 1H).

LRMS: m/z (APCI$^+$) 493 [MH$^+$]

PREPARATION 70

4-[4-Benzyl-5-(3,4,5,6-tetrahydro-2H-[1,2']bipyridinyl-4-yl)-4H-[1,2,4]triazol-3-ylmethyl]-piperazine-1-carboxylic acid benzyl ester

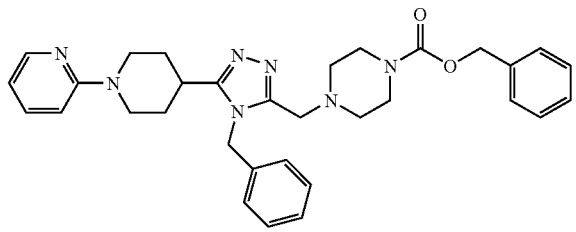

A mixture of the oxadiazole from preparation 56 (250 mg, 0.54 mmol), para-toluene sulphonic acid (20 mg), and benzylamine (176 μl, 1.62 mmol) in xylene (8 ml) was heated at 150° C. for 18 hours. The cooled reaction was evaporated under reduced pressure and the residue partitioned between ethyl acetate (100 ml) and water (50 ml), and the layers separated. The organic solution was dried (MgSO$_4$), evaporated under reduced pressure and the residue triturated with ether to afford the title compound as a white solid, 155 mg.

$^1$H NMR (CD$_3$OD, 400 MHz) δ: 1.77 (m, 2H), 1.84 (m, 2H), 2.18 (br s, 4H), 2.82 (m, 2H), 3.01 (m, 1H), 3.33 (s, 4H), 3.63 (s, 2H), 4.28 (m, 2H), 5.09 (s, 2H), 5.47 (s, 2H), 6.62 (m, 1H), 6.81 (d, 1H), 7.11 (m, 2H), 7.22–7.41 (m, 8H), 7.52 (m, 1H), 8.02 (m, 1H).

LRMS: m/z (APCI$^+$) 552 [MH$^+$]

PREPARATION 71

C-[4-Benzyl-5-(3,4,5,6-tetrahydro-2H-[1,2']bipyridinyl-4-yl)-4H-[1,2,4]triazol-3-yl]-methylamine

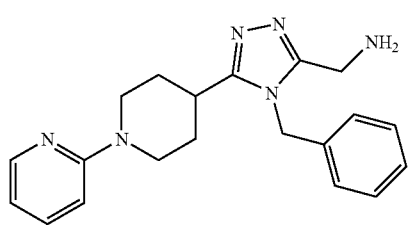

A mixture of the protected amine from preparation 65 (660 mg, 1.47 mmol) in dichloromethane (10 ml) and trifluoroacetic acid (10 ml) was stirred at room temperature for 2.5 hours. The reaction was evaporated under reduced pressure and the residue partitioned between aqueous sodium carbonate solution and dichloromethane. The layers were separated, the aqueous extracted further with dichloromethane and the combined organic solutions washed with brine and dried (MgSO$_4$), then evaporated under reduced pressure to afford the title compound as a white solid, 500 mg.

$^1$H NMR (CD$_3$OD, 400 MHz) δ: 1.77 (m, 2H), 1.82–1.91 (m, 2H), 2.86 (m, 2H), 3.03 (m, 1H), 3.88 (br s, 2H), 4.28 (m, 2H), 5.40 (s, 2H), 6.63 (m, 1H), 6.82 (d, 1H), 7.11 (d, 2H), 7.33–7.41 (m, 3H), 7.52 (m, 1H), 8.04 (d, 1H).

LRMS: m/z (APCI$^+$) 349 [MH$^+$]

PREPARATION 72

4-(4-Benzyl-5-piperazin-1-ylmethyl-4H-[1,2,4]triazol-3-yl)-3,4,5,6-tetrahydro-2H-[1,2']bipyridinyl

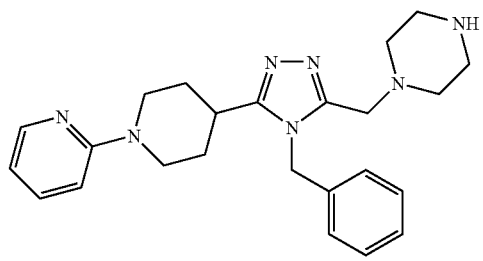

A mixture of the protected piperazine from preparation 70 (225 mg, 0.4 mmol) and 10% palladium on charcoal (30 mg) in ethanol (20 ml) was hydrogenated at 60 psi and room temperature for 2 hours. The mixture was filtered through Arbocel® and the filtrate evaporated under reduced pressure. The residue was purified by column chromatography on silica gel using an Isolute® silica cartridge and an elution gradient of dichloromethane:methanol:0.88 ammonia (95: 5:0 to 90:10:1) to give the title compound as a white solid, 125 mg.

$^1$H NMR (CD$_3$OD, 400 MHz) δ: 1.76 (m, 2H), 1.88 (m, 2H), 2.41 (m, 4H), 2.70 (m, 4H), 2.83 (m, 2H), 2.99 (m, 1H), 3.61 (s, 2H), 4.28 (d, 2H), 5.47 (s, 2H), 6.63 (dd, 1H), 6.81 (d, 1H), 7.13 (d, 1H), 7.36 (m, 3H), 7.52 (m, 1H), 8.04 (m, 1H).

LRMS: m/z (APCI$^+$) 418 [MH$^+$]

PREPARATION 73

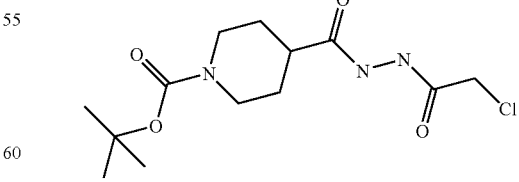

4-[N'-(2-Chloro-acetyl)-hydrazinocarbonyl]-piperidine-1-carboxylic acid tert-butyl ester 4-Hydrazinocarbonyl-piperidine-1-carboxylic acid tert-butyl ester (see reference WO 9703986 A1 19970206)(25 g, 103 mmol) was dissolved in dichloromethane (300 ml) and 4-methylmorpholine (12.5 ml, 113 mmol) was added. The mixture was cooled using an ice bath and chloroacetyl chloride (8.2 ml, 103 mmol) was added drop wise. The reaction was warmed to room temperature and was stirred for 4 hours. The reaction mixture was partitioned with aqueous sodium hydrogen carbonate solution, dried over magnesium sulphate, filtered and the filtrate evaporated to give the title compound as an off white solid (29.6 g).

APCI MS m/z 318 [M–H]+

Found; C, 48.01; H, 6.91; N, 12.85; $C_{13}H_{22}N_3O_4Cl$ 0.3$H_2O$ requires; C, 48.02; H, 7.01; N, 12.92%.

PREPARATION 74

4-(5-Chloromethyl-[1,3,4]oxadiazol-2-yl)-piperidine-1-carboxylic acid tert-butyl ester

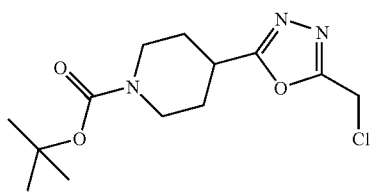

The hydrazide of preparation 73 (5.0 g, 15.6 mmol) was suspended in dichloromethane (200 ml) and pyridine (6.4 ml, 78 mmol) added before cooling the mixture to 10° C. Trifluoroacetic anhydride (6.6 ml, 39 mmol) was added drop wise over 15 min and then stirred at room temperature for 3 hr. Reaction mixture partitioned with water (50 ml), the organic layer was dried over magnesium sulphate, filtered and the filtrate evaporated under reduced pressure. The residue was purified by chromatography on silica gel using methanol in dichloromethane as eluant (2:98) to give the title compound as a white solid (2.95 g).

$^1$H NMR (400 MHz, CD$_3$OD): δ 1.45 (s, 9H), 1.74 (m, 2H), 2.19 (m, 2H), 3.04 (m, 2H), 3.24 (m, 1H), 4.09 (m, 2H), 4.85 (s, 2H)

PREPARATION 75

4-(5-Morpholin-4-ylmethyl-[1,3,4]oxadiazol-2-yl)-piperidine-1-carboxylic acid tert-butyl ester

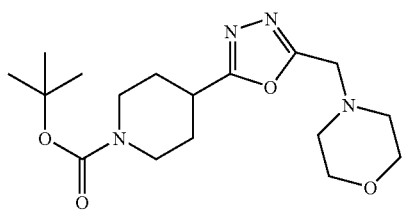

The title compound was prepared from the chloride of preparation 74 and morpholine as an orange oil, in 73% yield, using a procedure similar to that described in preparation 40.

LCMS: m/z APCI+ 253 [MH-BOC]+, 353 [MH]+

PREPARATION 76

4-(4-Benzyl-5-morpholin-4-ylmethyl-4H-[1,2,4]triazol-3-yl)-piperidine-1-carboxylic Acid tert-butyl ester

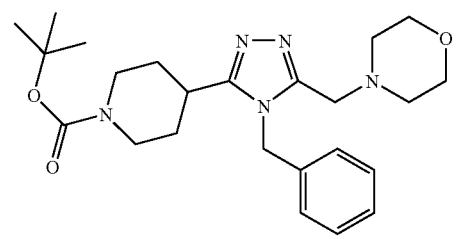

The title compound was prepared from the oxadiazole of preparation 75 and benzylamine as a pale yellow solid, in 73% yield, using a procedure similar to that described in preparation 65.

LCMS: m/z APCI+ 342[MH-BOC]+, 442 [MH]+

PREPARATION 77

4-(4-Benzyl-5-piperidin-4-yl-4H-[1,2,4]triazol-3-ylmethyl)-morpholine

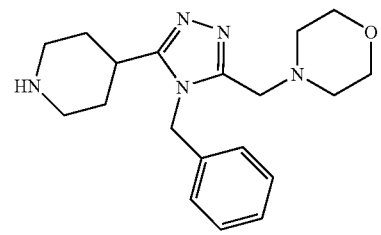

The protected piperidine of Preparation 76 (7.8 g, 17.7 mmol) was added to hydrogen chloride solution in 1,4-dioxane (4M, 25 ml) and the mixture was stirred at 15° C. for 18 hours. The solvent was evaporated and the residue was partition between dichloromethane and aqueous sodium carbonate solution. The organic phase was dried (MgSO$_4$) and evaporated under reduced pressure to give the title compound as a pale yellow gum (4.45 g).

LCMS: m/z APCI+ 342 [MH]+

PREPARATION 78

Chloro-acetic acid N'-(2-morpholin-4-yl-acetyl)-hydrazide

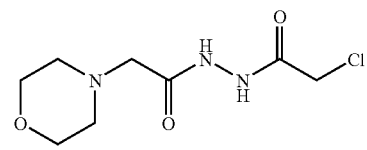

The title compound was obtained from morpholin-4-yl-acetic acid hydrazide (see reference Bull. Soc. Chim. Fr.

1962, 250) and chloroacetyl chloride in 87% yield as an off white solid, following the procedure described in Preparation 38.
LCMS: m/z ES⁺ 236 [M+H]⁺

PREPARATION 79

4-(5-Chloromethyl-[1,3,4]oxadiazol-2-ylmethyl)-morpholine

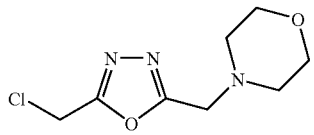

The title compound was obtained from the hydrazide of preparation 78 in 35% yield as a buff solid, following the procedure described in Preparation 18.
LCMS: m/z ES⁺ 218 [M+H]⁺

PREPARATION 80

4-[5-(4-Pyridin-2-yl-piperazin-1-ylmethyl)-[1,3,4]oxadiazol-2-ylmethyl]-morpholine

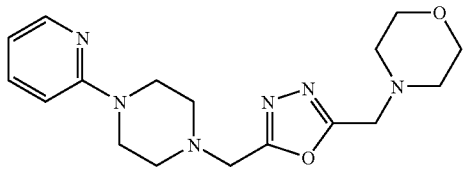

The title compound was obtained from the oxadiazole of preparation 79 and 1-(2-pyridyl)-piperidine in 28% yield as a yellow oil, following the procedure described in Preparation 40.
LCMS: m/z ES⁺ 346 [M+H]⁺

PREPARATION 81

4-[5-(4-Pyrimidin-2-yl-piperazin-1-ylmethyl)-[1,3,4]oxadiazol-2-ylmethyl]-morpholine

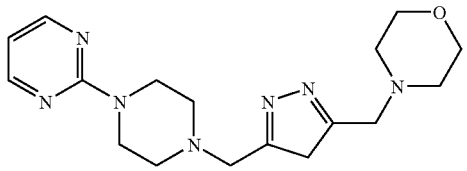

The title compound was obtained from the oxadiazole of preparation 79 and 1-(2-pyrimidyl)-piperidine in 42% yield as a yellow oil, following the procedure described in Preparation 40.
LCMS: m/z ES⁺ 368 [M+Na]⁺

PREPARATION 82

(R/S)-1-[5-(1-Pyrimidin-2-yl-piperidin-4-yl)-[1,3,4]oxadiazol-2-ylmethyl]-piperidin-3-ol

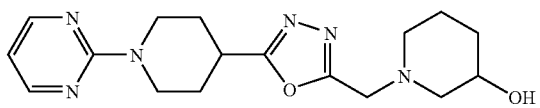

The title compound was obtained from the chloride of preparation 39a and piperidin-3-ol, following the procedure described in Preparation 40.
¹H NMR (400 MHz, d₆-DMSO): δ 0.98 (1H, m), 1.38 (1H, m). 1.52–1.67 (3H, m), 1.74 (1H, m), 1.80 (1H, m), 1.97 (1H, m), 2.03 (2H, m), 2.61 (1H, m), 2.79 (1H, m), 1.16 (2H, t), 3.30 (1H, m), 3.41 (1H, m), 3.72 (2H, ABq), 4.55 (2H, br d), 4.61 (1H, d), 6.60 (1H, t), 8.36 (2H, d).
LCMS: m/z ES⁺ 345 [M+H]⁺

PREPARATION 83

(R)-2-[N'-(3,4,5,6-Tetrahydro-2H-[1,2']bipyridinyl-4-carbonyl)-hydrazinocarbonyl]-pyrrolidine-1-carboxylic acid tert-butyl ester

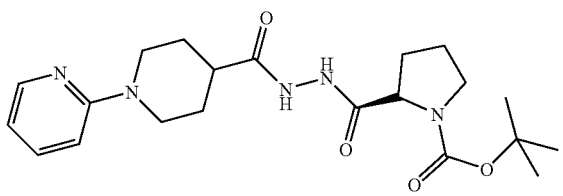

A mixture of (R)-proline-1-tert-butyl ester (3.08 g, 14.33 mmol), 1-hydroxybenzotriazole hydrate (1.93 g, 14.33 mmol) and 1-(3-dimethylaminopropyl-3-ethylcarbodiimide hydrochloride (3.43 g, 17.9 mmol) in dichloromethane (100 ml) was stirred for 10 minutes. The hydrazide of preparation 35 (3.5 g, 11.94 mmol) and triethylamine (5.8 ml, 41.8 mmol) were added and the reaction mixture was stirred under a nitrogen atmosphere for 18 hours. The reaction mixture was diluted with dichloromethane (100 ml) and partitioned with 2M aqueous sodium hydroxide solution (50 ml). The organic layer was washed with saturated aqueous sodium chloride solution and dried (MgSO₄). The reaction mixture was concentrated under reduced pressure and the solid formed was triturated with ether and isolated by filtration. The material obtained was dried under vacuum at 40° C. to give the title compound (4.45 g) as a white solid.
LCMS: m/z ES⁺ 418 [M+H]⁺

PREPARATION 84

(R)-2-[5-(3,4,5,6-Tetrahydro-2H-[1,2']bipyridinyl-4-yl)-[1,3,4]oxadiazol-2-yl]-pyrrolidine-1-carboxylic acid tert-butyl ester

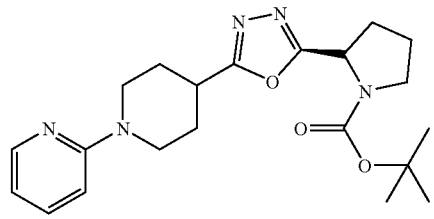

Trifluoromethane sulphonic anhydride (0.49 ml, 3.0 mmol) was added drop wise to an ice-cooled solution of the hydrazide from preparation 83 (500 mg, 1.2 mmol), in dichloromethane (50 ml) and pyridine (0.48 ml, 6.0 mmol), so as to maintain the temperature below 5° C. The reaction was stirred with ice cooling for a further 2 hours, and was then diluted with dichloromethane (50 ml), and washed with 4% aq ammonia. This aqueous wash was extracted with dichloromethane (50 ml), and the combined organic extracts were dried (MgSO$_4$) and evaporated under reduced pressure to give an oil. This was purified by column chromatography on silica gel using an elution gradient of diethyl ether to afford the title compound as a yellow foam, 365 mg.

$^1$H NMR (400 MHz, CDCl$_3$): δ 1.22–1.56 (m, 9H), 1.82–2.20 (m, 7H), 2.35 (m, 1H), 3.02-3.20 (m, 3H), 3.38–3.64 (m, 2H), 4.32 (bd, 2H), 4.96–5.13 (m, 1H), 6.62 (t, 1H), 6.68 (d, 1H), 7.50 (bt, 1H), 8.18 (d, 1H)

PREPARATION 85

(R)-4-[5-(Tetrahydro-furan-3-yloxymethyl)-[1,3,4] oxadiazol-2-yl]-3,4,5,6-tetrahydro-2H-[1,2']bipyridinyl

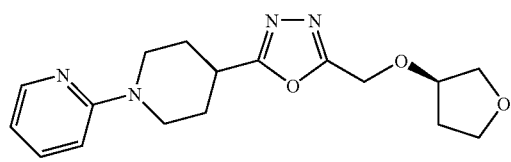

The title compound was obtained from the chloride of preparation 39 and (R)— tetrahydrofuran-3-ol, following the procedure described in Preparation 43, as a yellow oil in 46% yield.

LCMS: m/z ES$^+$ 331 [M+H]$^+$

PREPARATION 86

(S)-4-[5-(Tetrahydro-furan-3-yloxymethyl)-[1,3,4] oxadiazol-2-yl]-3,4,5,6-tetrahydro-2H-[1,2']bipyridinyl

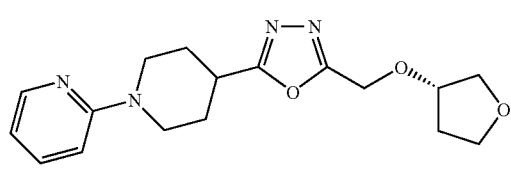

The title compound was obtained from the chloride of preparation 39 and (S)-tetrahydro-furan-3-ol, following the procedure described in Preparation 43.

LCMS: m/z ES$^+$ 331 [M+H]$^+$

PREPARATION 87

{Methyl-[5-(3,4,5,6-tetrahydro-2H-[1,2']bipyridinyl-4-yl)-[1,3,4]oxadiazol-2-ylmethyl]-amino}-acetic acid tert-butyl ester

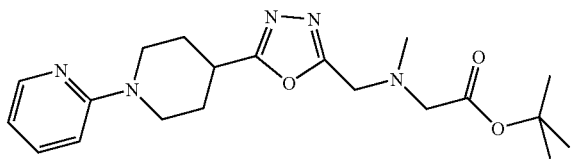

The title compound was obtained from the chloride of preparation 39 and methylamino-acetic acid tert-butyl ester, following the procedure described in Preparation 40, as a pale yellow oil in 86% yield.

LCMS: m/z ES$^+$ 410 [M+Na]$^+$

PREPARATION 88

Tetrahydro-furan-2-carboxylic acid N'-(3,4,5,6-tetrahydro-2H[1,2']bipyridinyl-4-carbonyl)-hydrazide

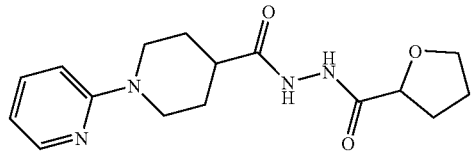

The title compound was obtained from the hydrazide of preparation 35 and tetrahydro-furan-2-carboxylic acid, following the procedure described in Preparation 83, as a white solid.

$^1$H NMR (400 MHz, CDCl$_3$): δ 1.65–1.99 (6H, m), 2.13 (1H, q), 2.30 (1H, m), 2.52 (1H, m), 2.91 (2H, t), 3.87 (1H, q), 4.00 (1H, q), 4.32 (2H, br d), 4.46 (1H, t), 6.60 (1H, t), 6.66 (1H, d), 7.45 (1H, t), 8.16, (1H, d), 8.72 (1H, d), 9.00 (1H, d).

LCMS: m/z ES$^+$ 341 [M+Na]$^+$

PREPARATION 89

4-[5-(Tetrahydro-furan-2-yl)-[1,3,4]oxadiazol-2-yl]-3,4,5,6-tetrahydro-2H-[1,2']bipyridinyl

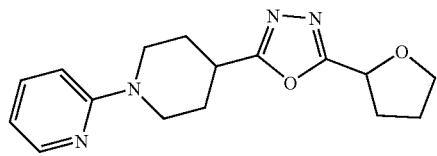

The title compound was obtained from the hydrazide of preparation 88 following the procedure described in Preparation 84, as a yellow oil.

$^1$H NMR (400 MHz, d$_4$-MeOH): δ 1.89 (2H, dq), 2.00–2.10 (4H, m), 2.17 (2H, m), 3.12 (2H, t), 3.27 (1H, m), 3.96 (2H, dq), 4.26 (2H, d), 5.15 (1H, dd), 6.65 (1H, dd), 6.87 (1H, d), 7.55 (1H, t), 8.07 (1H, d).
LCMS: m/z ES⁺ 323 [M+Na]⁺

PREPARATION 90

3,4,5,6-Tetrahydro-2H-[1,2']bipyridinyl-4-carboxylic acid N'-(2-tetrahydro-pyran-4-yl-acetyl)-hydrazide

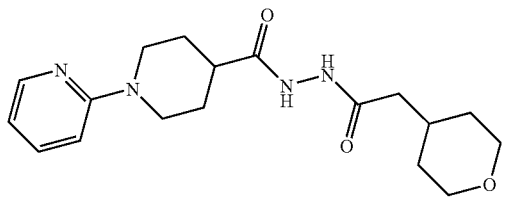

The title compound was obtained from the hydrazide of preparation 35 and tetrahydro-furan-2-carboxylic acid, following a procedure similar to that described in Preparation 83, as a white solid in 59% yield.
MS: m/z ES⁺ 347 [M+H]⁺

PREPARATION 91

4-[5-(Tetrahydro-pyran-4-ylmethyl)-[1,3,4]oxadiazol-2-yl]-3,4,5,6-tetrahydro-2H-[1,2']bipyridinyl

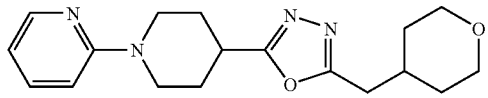

The title compound was obtained from the hydrazide of preparation 90 following the procedure described in Preparation 84, as an orange oil in 53% yield.
MS: m/z ES⁺ 329 [M+H]⁺

PREPARATION 92

4-(5-Ethoxymethyl-[1,3,4]oxadiazol-2-yl)-3,4,5,6-tetrahydro-2H-[1,2']bipyridinyl

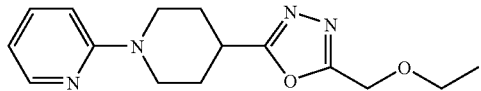

The title compound was obtained from the chloride of preparation 39 and ethanol, following the procedure described in Preparation 43, as a clear oil in 35% yield.
¹H NMR (400 MHz, CDCl₃): δ 1.25 (3H, t), 1.96 (2H, dq), 2.20 (2H, br d), 3.08 (2H, dt), 3.19 (1H, m), 3.62 (2H, q), 4.32 (2H, d), 4.67 (2H, s), 6.62 (1H, dd), 6.72 (1H, d), 7.48 (1H, t), 8.20 (1H, d).
LCMS: m/z ES⁺ 311 [M+Na]⁺

PREPARATION 93

4-[5-(2-Methoxy-ethoxymethyl)-[1,3,4]oxadiazol-2-yl]-3,4,5,6-tetrahydro-2H-[1,2']bipyridinyl

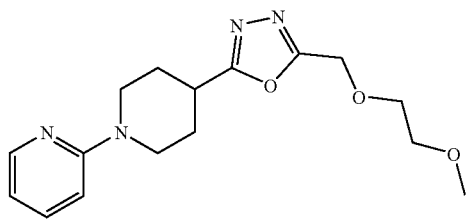

The title compound was obtained from the chloride of preparation 39 and 2-methoxy-ethanol, following the procedure described in Preparation 43, as pale yellow oil in 65% yield.
MS: m/z ES⁺ 319 [M+H]⁺

PREPARATION 94

[5-(3,4,5,6-Tetrahydro-2H-[1,2']bipyridinyl-4-yl)-[1,3,4]oxadiazol-2-ylmethoxy]-acetic acid tert-butyl ester

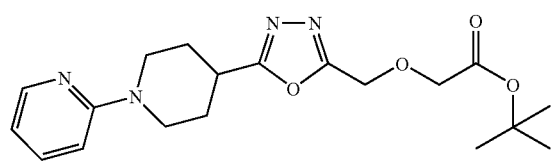

The title compound was obtained from the chloride of preparation 39 and Hydroxy-acetic acid tert-butyl ester, following the procedure described in Preparation 43, as a pale pink oil in 54% yield.
MS: m/z ES⁺ 375 [M+H]⁺

PREPARATION 95

4-(5-Methylsulfanylmethyl-[1,3,4]oxadiazol-2-yl)-3,4,5,6-tetrahydro-2H-[1,2']bipyridinyl

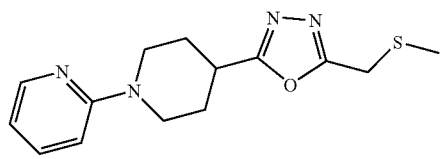

Sodium methane thiolate (565 mg, 2.25 mmol) was added to a suspension of the chloromethyl compound of Preparation 39 (1.0 g, 3.59 mmol) in tetrahydrofuran (20 ml). The mixture was stirred at room temperature for 16 hours. Ethyl acetate (100 ml) was added and the solution was extracted with water (100 ml). The aqueous solution was washed with ethyl acetate (2×100 ml) and the combined organic layers were dried over magnesium sulphate and evaporated under reduced pressure to give the title compound as a pale yellow solid (1.17 g).

PREPARATION 96

4-(5-Pyrazol-1-ylmethyl-[1,3,4]oxadiazol-2-yl)-3,4,5,6-tetrahydro-2H-[1,2']bipyridinyl

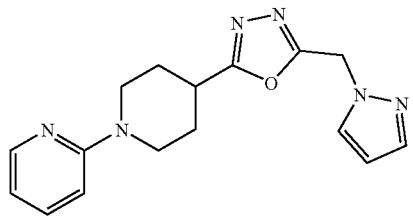

The title compound was obtained from the chloride of preparation 39 and 1H-pyrazole, following the procedure described in Preparation 40, as a yellow oil in 47% yield.

LCMS: m/z ES$^+$ 311 [M+H]$^+$

PREPARATION 97

4-(5-[1,2,3]Triazol-2-ylmethyl-[1,3,4]oxadiazol-2-yl)-3,4,5,6-tetrahydro-2H-[1,2']bipyridinyl

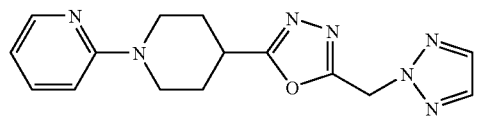

The title compound was obtained from the chloride of preparation 39 and 2H-[1,2,3]-triazole, following the procedure described in Preparation 40, as a clear oil in 35% yield.

LCMS: m/z ES$^+$ 312[M+H]$^+$, 334 [M+Na]$^+$

PREPARATION 98

4-(5-[1,2,3]Triazol-1-ylmethyl-[1,3,4]oxadiazol-2-yl)-3,4,5,6-tetrahydro-2H-[1,2']bipyridinyl

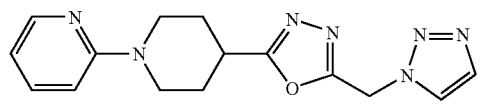

The title compound was obtained from the chloride of preparation 39 and 2H-[1,2,3]-triazole, following the procedure described in Preparation 40, as a clear oil in 25% yield.

LCMS: m/z ES$^+$ 312 [M+H]$^+$, 334 [M+Na]$^+$ $^1$H NMR (400 MHz, CDCl$_3$): δ 1.96 (dq, 2H), 2.16–2.23 (m, 5H), 3.08 (dt, 2H), 3.18 (m, 1H), 3.80 (s, 2H), 4.32 (td, 2H), 6.62 (dd, 1H), 6.71 (dd, 1H), 7.48 (t, 1H), 8.20 (d, 1H).

LCMS: m/z ES$^+$ 291 [M+H]$^+$

PREPARATION 99

4-[5-(Pyridin-4-yloxymethyl)-[1,3,4]oxadiazol-2-yl]-3,4,5,6-tetrahydro-2H-[1,2']bipyridinyl

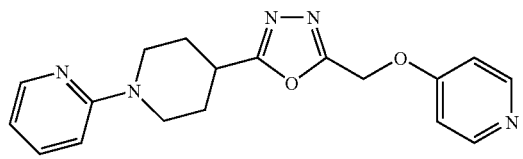

The title compound was obtained from the chloride of preparation 39 and 4-hydroxypyridine, following the procedure described in Preparation 40, as a yellow oil in 50% yield.

LCMS: m/z ES$^+$ 338 [M+H]$^+$

EXAMPLE 1

(S)-4-[5-Butyl-4-(1-phenyl-ethyl)-4H-[1,2,4]triazol-3-yl]-3,4,5,6-tetrahydro-2H-[1,2']bipyridinyl

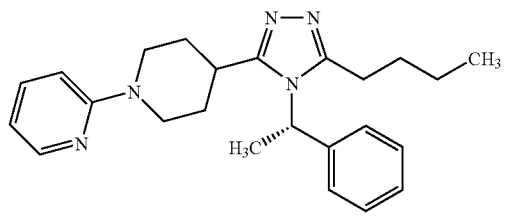

The oxadiazole of Preparation 26 (149 mg, 0.52 mmol), anhydrous magnesium chloride (20 mg, 0.21 mmol) and S-(−)-1-phenylethylamine (120 μl, 1 mmol) were heated at 150° C. for 18 hours. The reaction mixture was cooled to room temperature and dissolved in dichloromethane. The organic solution was washed with brine (3×20 ml) dried over sodium sulphate and evaporated under reduced pressure. The residue was purified by chromatography on silica gel using methanol in dichloromethane as eluant (4:96). The material obtained was co-evaporated with diethyl ether and then co-evaporated with methanol to give the title compound as a brown oil (90 mg).

$^1$H NMR (400 MHz, CD$_3$OD): δ 0.90 (t, 3H), 1.37 (m, 4H), 1.68 (m, 3H), 1.98 (m, 3H), 2.63 (m, 2H), 2.73 (m, 1H), 2.91 (m, 2H), 4.19 (d, 1H), 4.35 (d, 1H), 5.82 (q, 1H), 6.64 (m, 1H), 6.81 (d, 1H), 7.26 (d, 2H), 7.38 (m, 2H), 7.44 (m, 1H), 7.52 (m, 1H), 8.04 (d, 1H).

LCMS: m/z ES$^+$ 390 [M+H]$^+$

Found; C, 72.54; H, 8.11; N, 17.28; C$_{24}$H$_{31}$N$_5$0.5H$_2$O requires; C, 72.33; H, 8.09; N, 17.57%.

EXAMPLES 2–17

The compounds of the following tabulated examples (Table 7) of the general formula:

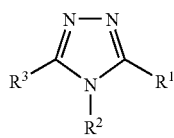

were prepared by a similar method to that of example 1 using the appropriate oxadiazole and amine.

TABLE 7

| Example number | R¹ | R² | R³ |
|---|---|---|---|
| 2^A | isopentyl (CH(CH₃)CH₂CH(CH₃)... 2-methylbutyl) | benzyl | 2-(pyrimidin-2-yl)piperidin-4-yl |
| 3^B | CH₃ | (S)-1-phenylethyl | 2-(pyrimidin-2-yl)piperidin-4-yl |
| 4^C | n-butyl | benzyl | 2-(pyrimidin-2-yl)piperidin-4-yl |
| 5^D | isobutyl | benzyl | 2-(pyrimidin-2-yl)piperidin-4-yl |
| 6^E | cyclopropyl | benzyl | 2-(pyrimidin-2-yl)piperidin-4-yl |
| 7^F | CH₃ | 1-phenylpropyl | 2-(pyrimidin-2-yl)piperidin-4-yl |
| 8^G | n-propyl | benzyl | 2-(pyrimidin-2-yl)piperidin-4-yl |
| 9^H | (2-chlorophenoxy)methyl | benzyl | 2-(pyrimidin-2-yl)piperidin-4-yl |
| 10^I | n-butyl | benzyl | 2-(pyrimidin-2-yl)piperidin-4-yl |
| 11^F | CH₃ | (R)-1-phenylethyl | 2-(pyrimidin-2-yl)piperidin-4-yl |
| 12^J | (4-fluorophenoxy)methyl | benzyl | 2-(pyrimidin-2-yl)piperidin-4-yl |
| 13^F | CH₃ | 3-methylbenzyl | 2-(pyrimidin-2-yl)piperidin-4-yl |
| 14^K | CH₃ | (R)-1-phenylethyl | 2-(pyrimidin-2-yl)piperidin-4-yl |

TABLE 7-continued

| Example number | R¹ | R² | R³ |
|---|---|---|---|
| 15$^F$ | CH₃ | 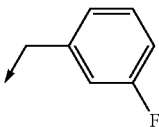 | 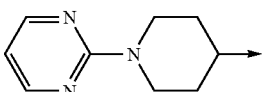 |
| 16$^L$ | 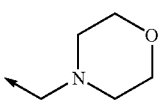 | 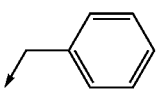 | 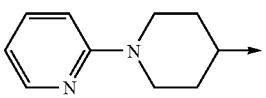 |
| 17$^M$ | 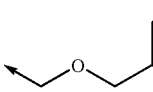 | 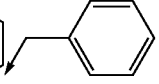 | 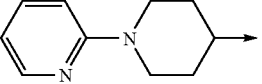 |

$^A$see Preparation 18 for the oxadiazole
$^B$see Preparation 27 for the oxadiazole
$^C$see Preparation 26 for the oxadiazole
$^D$see Preparation 23 for the oxadiazole
$^E$see Preparation 22 for the oxadiazole
$^F$see Preparation 30 for the oxadiazole
$^G$see Preparation 20 for the oxadiazole
$^H$see Preparation 21 for the oxadiazole
$^I$see Preparation 19 for the oxadiazole
$^J$see Preparation 25 for the oxadiazole
$^K$see Preparation 34 for the oxadiazole
$^L$see Preparation 29 for the oxadiazote
$^M$see Preparation 37 for the oxadiazole

EXAMPLE 2

2-[4-(4-Benzyl-5-isobutyl-4H-[1,2,4]triazol-3-yl)-piperidin-1-yl]-pyrimidine $^1$H NMR (400 MHz, DMSO-d₆): δ 0.86 (d, 6H), 1.68 (m, 4H), 1.93 (m, 1H), 2.43 (d, 2H), 2.98 (m, 3H), 4.61 (d, 2H), 5.27 (s, 2H), 6.59 (m, 1H), 6.99 (d, 2H), 7.31 (m, 1H), 7.37 (m, 2H), 8.33 (d, 2H).
LRMS: m/z APCI 377 [M+H]$^+$

EXAMPLE 3

(S)-4-(5-Methyl-4-(1-phenyl-ethyl)-4H-[1,2,4]triazol-3-yl]-3,4,5,6-tetrahydro-2H-[1,2']bipyridinyl $^1$H NMR (400 MHz, CDCl₃): δ 1.72 (m, 3H), 1.93 (d, 3H), 2.08 (m, 4H), 2.23 (s, 3H), 2.80 (m, 2H), 2.93 (m, 1H), 4.33 (d, 1H), 4.40 (d, 2H), 5.54 (q, 1H), 6.60 (m, 1H), 6.66 (d, 1H), 7.12 (d, 1H), 7.28 (m, 3H), 7.46 (m, 1H), 8.15 (d, 1H).
LCMS: m/z ES$^+$ 348 [M+H]$^+$
Found; C, 70.57; H, 7.47; N, 19.49; C₂₁H₂₅N₅0.5H₂O requires; C, 70.76; H, 7.35; N, 19.65%.

EXAMPLE 4

4-[4-Benzyl-5-butyl-4H-[1,2,4]triazol-3-yl]-3,4,5,6-tetrahydro-2H-[1,2']bipyridinyl $^1$H NMR (400 MHz, CDCl₃): δ 0.88 (t, 3H), 1.40 (m, 2H), 1.70 (m, 2H), 1.85 (m, 2H), 2.07, (m, 2H), 2.67 (m, 2H), 1.79 (m, 1H), 2.89 (m, 2H), 4.34 (d, 2H), 5.11 (s, 2H), 6.59 (m, 1H), 6.65 (d, 1H), 7.36 (m 3H), 7.44 (m, 1H), 8.15 (d, 1H).
LCMS: m/z ES$^+$ 398 [M+Na]$^+$
Found; C, 73.40; H, 7.82; N, 18.59; C₂₃H₂₉N₅ requires; C, 73.57; H, 7.78; N, 18.65%.

EXAMPLE 5

2-[4-(4-Benzyl-5-isopropyl-4H-[1,2,4]triazol-3-yl)-piperidin-1-yl]-pyrimidine $^1$H NMR (400 MHz, CDCl₃): δ 1.33 (d, 6H), 1.81 (m, 2H), 1.99 (m, 2H), 2.90 (m, 4H), 4.75 (m, 2H), 5.13 (s, 2H), 6.45 (t, 1H), 6.94 (d, 2H), 7.34 (m 3H), 8.27 (d, 2H).
LCMS: m/z ES$^-$ 361 [M−H]$^-$

EXAMPLE 6

2-[4-(4-Benzyl-5-cyclopropyl-4H-[1,2,4]triazol-3-yl)-piperidin-1-yl]-pyrimidine

HPLC Waters Xterra™ C18 5 μm 19×100 mm 50:50 (H₂O+0.1% diethylamine/acetonitrile), 18 ml/min. 1.04 min
LRMS: m/z APCI 353[M+H]$^+$

EXAMPLE 7

(S)-2-{4-[5-Methyl-4-(1-phenyl-propyl)-4H-[1,2,4]triazol-3-yl)-piperidin-1-yl]-pyrimidine $^1$H NMR (400 MHz, CDCl₃): δ 0.92 (m, 2H), 1.10 (m, 2H), 1.60 (m, 1H), 1.80 (m, 2H), 2.99 (m, 2H), 4.78 (m, 2H), 5.22 (s, 2H), 6.46 (t, 1H), 7.01 (d, 2H), 7.37 (m 3H), 8.27 (d, 2H).
APCI MS m/z 361 [M+H]$^+$

EXAMPLE 8

2-[4-(4-Benzyl-5-propyl-4H-[1,2,4]triazol-3-yl)-piperidin-1-yl]-pyrimidine $^1$H NMR (400 MHz, CDCl$_3$): δ 0.99 (t, 3H), 1.43 (d, 1H), 1.91 (m, 3H), 2.19 (m, 1H), 2.29 (s, 3H), 2.54 (m, 1H), 2.77 (m 2H), 3.92 (m, 1H), 4.72 (d, 1H), 4.81 (d, 1H), 5.26 (m, 1H), 6.44 (t, 1H), 7.13 (d, 2H), 7.35 (m, 3H), 8.28 (d, 2H).
LCMS: m/z ES$^+$ 363 [M+H]$^+$

EXAMPLE 9

2-{4-[4-Benzyl-5-(2-chloro-phenoxymethyl)-4H-[1,2,4]triazol-3-yl]-piperidin-1-yl}-pyrimidine $^1$H NMR (400 MHz, CDCl$_3$): δ 0.95 (t, 3H), 1.78 (m, 4H), 1.96 (m, 2H), 2.60 (t, 2H), 2.79 (m, 1H), 2.94 (t, 2H), 4.78 (d, 2H), 5.09 (s, 2H), 6.44 (t, 1H), 6.95 (d, 2H), 7.34 (m, 3H), 8.28 (d, 2H).
LCMS: m/z ES$^+$ 363 [M+H]$^+$

EXAMPLE 10

2-[4-(4-Benzyl-5-butyl-4H-[1,2,4]triazol-3-yl)-piperidin-1-yl]-pyrimidine $^1$H NMR (400 MHz, CDCl$_3$): δ 0.84 (m, 2H), 2.01 (m, 2H), 2.93 (m, 3H), 4.80 (d, 2H), 5.17 (s, 2H), 5.40 (s, 2H), 6.48 (t, 1H), 6.93 (m, 1H), 7.04 (m, 2H), 7.11 (d, 1H), 7.20 (m, 1H), 7.33 (m, 3H), 8.30 (d, 2H).
LCMS: m/z ES$^+$ 461, 463 [M+H]$^+$

EXAMPLE 11

(S)-2-{4-[5-Methyl-4-(1-phenyl-ethyl)-4H-(1,2,4]triazol-3-yl)-piperidin-1-yl}-pyrimidine $^1$H NMR (400 MHz, CDCl$_3$): δ 0.89 (t, 3H), 1.38 (q, 2H), 1.70 (m, 2H), 1.80 (d, 2H), 1.99 (m, 2H), 2.63 (t, 2H), 2.80 (m, 1H), 2.94 (m, 2H), 4.76 (d, 2H), 5.10 (s, 2H), 6.46, (t, 1H), 6.95 (d, 2H), 7.33 (m, 3H), 8.27 (d, 2H).
APCI MS m/z 377 [M+H]$^+$

EXAMPLE 12

2-{4-[4-Benzyl-5-(4-fluoro-phenoxymethyl)-4H-[1,2,4]triazol-3-yl]-piperidin-1-yl}-pyrimidine $^1$H NMR (400 MHz, CDCl$_3$): δ 1.79 (m, 2H), 1.99 (m, 2H), 2.90 (m, 3H), 4.77 (m, 2H), 5.11 (s, 2H), 5.28 (s, 2H), 6.48 (t, 1H), 6.83 (m, 2H), 6.90 (m, 2H), 6.99 (m, 2H), 7.31 (m, 3H), 8.26 (d, 2H).
LCMS: m/z ES$^+$ 467 [M+Na]$^+$

EXAMPLE 13

2-{4-[5-Methyl-4-(3-methyl-benzyl)-4H-[1,2,4]triazol-3-yl]-piperidin-1-yl}-pyrimidine LCMS: m/z ES$^+$ 349 [M+H]$^+$
HPLC Phenomenex C$_8$ 5 µm 10×150 mm, 50:50 (H$_2$O+ 0.1% diethylamine/acetonitrile), 8 ml/min. 214 nM 4.41 min.

EXAMPLE 14

(S)-2-{4-[5-Methyl-4-(1-phenyl-ethyl)-4H-[1,2,4]triazol-3-ylmethyl]-piperidin-1-yl}-pyrimidine $^1$H NMR (400 MHz, CDCl$_3$): δ 1.19 (m, 2H), 1.80 (m, 1H), 1.88 (m, 4H), 2.10 (m, 1H), 2.26 (s, 3H), 2.50 (m, 1H), 2.63 (m, 1H), 2.82 (m, 2H), 4.70 (m, 2H), 5.47 (m, 1H), 6.42 (t, 1H), 7.09 (m, 2H), 7.35 (m, 3H), 8.26 (d, 2H).
LCMS: m/z ES$^-$ 385 [M–H]$^-$

EXAMPLE 15

2-{4-[4-(3-Fluoro-benzyl)-5-methyl-4H-[1,2,4]triazol-3-yl)-piperidin-1-yl]-pyrimidine HPLC Phenomenex C$_{8-5}$ µm 10×150 mm, 50:50 (H$_2$O+ 0.1% diethylamine/acetonitrile), 8 ml/min. 214 nM, 1.24 min.
LRMS: m/z APCI 353[M+H]$^+$

EXAMPLE 16

4-(4-Benzyl-5-morpholin-4-ylmethyl-4H-[1,2,4]triazol-3-yl)-3,4,5,6-tetrahydro-2H-[1,2']bipyridinyl $^1$H NMR (400 MHz, CD$_3$OD): δ 1.74 (m, 2H), 1.88 (m, 2H), 2.21 (m, 4H), 2.82 (m, 2H), 2.99 (m, 1H), 3.53 (m, 4H), 3.62 (s, 2H), 4.29 (m, 2H), 6.63 (m, 1H), 6.80 (d, 1H), 7.13 (d, 2H), 7.38 (m, 3H), 7.54 (m, 1H), 8.06 (d, 1H).
LRMS: m/z APCI 419[M+H]$^+$
Found; C, 68.53; H, 7.25; N, 19.79; C$_{24}$H$_{30}$N$_6$O requires C, 68.87; H, 7.22; N, 20.08%.

EXAMPLE 17

4-(4-Benzyl-5-benzyloxymethyl-4H-[1,2,4]triazol-3-yl)-3,4,5,6-tetrahydro-2H-[1,2']bipyridinyl $^1$H NMR (400 MHz, CD$_3$OD): δ 1.68 (m, 2H), 1.84 (m, 2H), 2.81 (m, 2H), 2.98 (m, 1H), 4.26 (m, 2H), 4.53 (s, 2H), 4.67 (s, 2H), 5.35 (s, 2H), 6.64 (m, 1H), 6.81 (d, 1H), 7.13 (m, 2H), 7.31 (m, 8H), 7.54 (m, 1H), 8.03 (d, 1H).
LRMS: m/z APCI 440[M+H]$^+$
Found; C, 72.67; H, 6.67; N, 15.87; C$_{27}$H$_{29}$N$_5$O0.3H$_2$O requires; C, 72.88; H, 6.71; N, 15.74%.

EXAMPLE 18

4-(4-Benzyl-5-methyl-4H-[1,2,4]triazol-3-yl)-3,4,5,6-tetrahydro-2H-[1,2']bipyridinyl

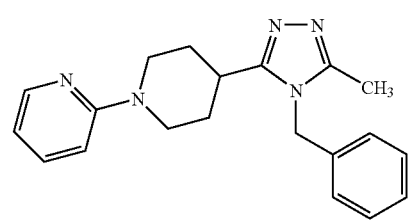

The piperidine from preparation 32 (200 mg, 0.6 mmol) was mixed with 2-chloropyridine (60 µl, 0.6 mmol) and diisopropyl ethylamine (310 µl, 1.8 mmol) in N-methylpyrrolidinone (5 ml) and the mixture was heated to 140° C. for 18 hours. The reaction mixture was cooled to room temperature, added to water (150 ml) and acidified with 2N hydrochloric acid. The aqueous solution was washed with ethyl acetate (3×100 ml), basified with solid sodium carbonate, filtered through Hyflo Super Cel® and extracted with ethyl acetate (3×20 ml). The combined organic layers were dried over sodium sulphate and evaporated under reduced pressure. The residual orange oil was purified by chromatography on silica gel using methanol in dichloromethane as eluant (6:94) to give the title compound as an orange oil (10 mg).

$^1$H NMR (400 MHz, CD$_3$OD): δ 1.83 (m, 4H), 2.38 (s, 3H), 2.89 (m, 2H), 3.02 (m, 1H), 4.30 (d, 2H), 5.35 (s, 2H), 6.64 (m, 1H), 7.08 (d, 2H), 7.20 (m, 3H), 7.34 (m, 1H), 7.60 (m, 1H), 8.06 (d, 1H).

LCMS: m/z ES+ 356 [M+Na]$^+$

EXAMPLE 19

(R)-2-[3-Methyl-5-(1-pyrimidin-2-yl-piperidin-4-yl)-[1,2,4]triazol-4-yl]-2-phenyl-ethanol

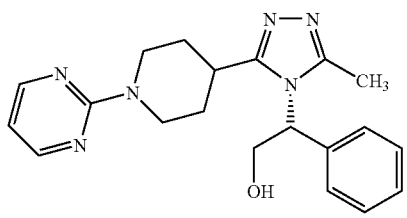

4-(5-Methyl-[1,3,4]oxadiazol-2-yl)-piperidine-1-carboxylic acid tert-butyl ester (1 g, 3.7 mmol)(see reference WO 0039125), (R)-(–)-2-amino-2-phenylethanol (617 mg, 4.4 mmol) and 4-methylphenylsulphonic acid (20 mg) in Xylene (10 ml) were heated under reflux for 48 hours. The solvent was evaporated under reduced pressure and the residue was partitioned between dichloromethane and sodium hydrogen carbonate solution. The aqueous layer was extracted with dichloromethane and the combined organic layers were washed with brine, dried over magnesium sulphate and evaporated under reduced pressure. The residue was purified by chromatography on silica gel using methanol and ammonium hydroxide in dichloromethane as eluant (10:1:90). The material obtained was dissolved in 4M hydrogen chloride solution in 1,4-dioxane and the mixture was stirred at 15° C. for 2 hours. The solvent was evaporated under reduced pressure and the residue was triturated with diethyl ether.

The material obtained was mixed with 2-bromopyrimidine (170 mg, 1.1 mmol) and potassium carbonate (308 mg, 2.2 mmol) in N,N-dimethylformamide (1 ml) and was heated at 50° C. for 4 hours. The reaction mixture was cooled to room temperature and was partitioned between water and dichloromethane. The aqueous phase was extracted with dichloromethane and the combined organic phases were washed with brine, dried over magnesium sulphate and evaporated under reduced pressure. The residue was pre-adsorbed onto a small quantity of silica gel and then was purified by chromatography on silica gel using methanol and ammonium hydroxide in ethyl acetate as eluant (9:0.1:91) to give the title compound as a white solid (46 mg).

$^1$H NMR (400 MHz, CDCl$_3$): δ 1.75 (m, 1H), 1.83 (m, 3H), 2.15 (s, 3H), 2.70 (t, 1H), 2.84 (m, 1H), 4.01 (t, 1H), 4.40 (m, 1H), 4.70 (m, 2H), 5.12 (s, 1H), 5.42 (m, 1H), 6.38 (d, 1H), 7.06 (d, 2H), 7.29 (m, 3H), 8.20 (d, 2H).

LCMS: m/z ES+ 365 [M+Na]$^+$

EXAMPLE 20

2-[4-(4-Benzyl-5-methyl-4H-[1,2,4]triazol-3-yl)-piperidin-1-yl]-4-methylpyrimidine

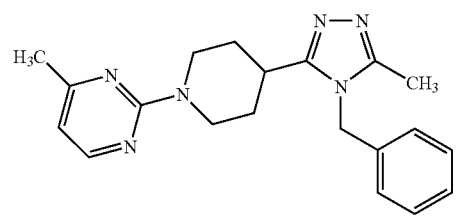

The piperidine of Preparation 32 (100 mg, 0.39 mmol) was mixed with 2-bromo-4-methylpyrimidine (88 mg, 0.51 mmol) and potassium carbonate (80 mg, 0.6 mmol) in N,N-dimethylformamide (0.5 ml) and was heated at 50° C. for 4 hours. The reaction mixture was cooled to room temperature and was partitioned between water and dichloromethane. The aqueous phase was extracted with dichloromethane and the combined organic phases were washed with brine, dried over magnesium sulphate and evaporated under reduced pressure. The residue was triturated with diethyl ether and the material obtained was purified by chromatography on silica gel using methanol in dichloromethane as eluant (10:90). The isolated solid was triturated with diethyl ether to give the title compound as a white solid (30 mg).

$^1$H NMR (400 MHz, CDCl$_3$): δ 1.76 (m, 2H), 1.92 (m, 2H), 2.06 (s, 3H), 2.10 (s, 3H), 2.77 (m, 1H), 4.76 (m, 2H), 5.05 (s, 2H), 6.30 (d, 1H), 6.95 (d, 2H), 7.30 (m, 3H), 8.10 (d, 1H). Found; C, 68.76; H, 7.04; N, 24.03; $C_{20}H_{24}N_6$ requires; C, 68.94; H, 6.94; N, 24.12%.

EXAMPLE 21

2-[4-(4-Benzyl-5-methyl-4H-[1,2,4]triazol-3-yl)-piperidin-1-yl]-pyrimidine

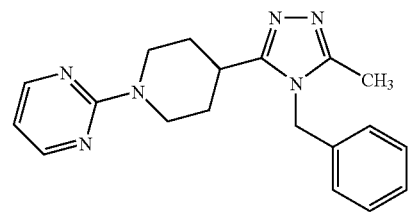

The title compound was obtained from the piperidine of Preparation 32 (100 mg, 0.39 mmol) and 2-bromopyrimidine in 39% yield following the procedure described in Example 20.

$^1$H NMR (400 MHz, CDCl$_3$): δ 1.78 (d, 2H), 1.98 (q, 2H), 2.32 (s, 3H), 2.78 (m, 1H), 2.92 (m, 2H), 4.75 (d, 2H), 5.05 (s, 2H), 6.42 (t, 1H), 6.93 (d, 2H), 7.32 (m, 3H), 8.24 (d, 2H).

LCMS: m/z ES+ 357 [M+Na]$^+$

EXAMPLE 22

4-(4-Benzyl-5-methyl-4H-[1,2,4]triazol-3-yl)-1-phenyl-piperidine

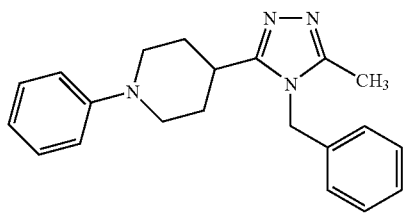

3-BromObenzene (80 μl, 0.75 mmol) was added to a mixture of the piperidine from Preparation 32 (250 mg, 0.75 mmol), sodium tert-butoxide (250 mg, 2.6 mmol) (+/−) 2,2'-bis(diphenylphosphino)-1,1'-binaphthyl, (19 mg, 0.03 mmol) and tris(dibenzylideneacetone)dipalladium (14 mg, 0.15 mmol) in toluene (20 ml) and the mixture was stirred at 70° C. for 4 hours. Diisopropylamine (260 μl, 2.6 mmol) and further quantities of 2,2'-bis(diphenylphosphino)-1,1'-binaphthyl (19 mg, 0.03 mmol) and tris(dibenzylideneacetone)dipalladium (14 mg, 0.15 mmol) were added and the reaction mixture was stirred at 70° C. for a further 4 hours. The reaction mixture was cooled to room temperature and evaporated under reduced pressure. The residue was partitioned between sodium carbonate solution (20 ml) and ethyl acetate (20 ml). The aqueous solution was extracted with ethyl acetate (2×20 ml) and the combined organic solutions were washed with brine, dried over sodium sulphate and evaporated under reduced pressure. The residual orange oil was purified by chromatography on silica gel using methanol in dichloromethane as eluant (gradient from 0:100 to 4:96) to give the title compound (16 mg).

$^1$H NMR (400 MHz, CDCl$_3$): δ 1.88 (d, 2H), 2.16 (m, 2H), 2.34 (s, 3H), 3.76 (d, 2H), 5.09 (s, 2H), 6.84 (m, 1H), 6.93 (d, 2H), 6.98 (d, 2H), 7.24 (m, 2H), 7.38 (m, 3H).

LCMS: m/z ES$^+$ 333 [M+H]$^+$

EXAMPLE 23

2-[4-(4-Benzyl-5-methyl-4H-[1,2,4]triazol-3-yl)-piperidin-1-yl]-pyrazine

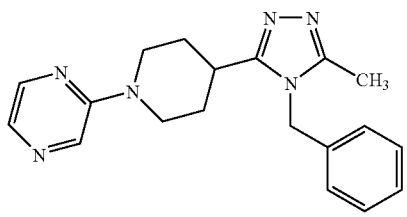

The piperidine of Preparation 32 (164 mg, 0.5 mmol) was mixed with 2-chloropyrazine (143 mg, 1.25 mmol) and diisopropylethylamine (129 μl, 1 mmol) in 1,4-dioxane (10 ml) and was heated under reflux for 3 hours. N,N-dimethylformamide (4 ml) was added and the mixture was heated at 100° C. for 48 hours. The solvent was evaporated under reduced pressure and the residue was dissolved in ethyl acetate (20 ml). The organic solution was washed with water (20 ml) and brine (20 ml), dried over magnesium sulphate and evaporated under reduced pressure. The residue was purified by chromatography on silica gel using methanol in dichloromethane as eluant (0.7:99.3) to give the title compound as an off white solid (45 mg).

M.p. 191.1° C.

$^1$H NMR (400 MHz, CDCl$_3$): δ 1.83 (m, 2H), 2.01 (m, 2H), 2.83 (s, 3H), 2.90 (m, 1H), 2.96 (m, 2H), 4.82 (m, 2H), 5.07 (s, 2H), 6.94 (m, 2H), 7.84 (m, 3H), 7.80 (d, 1H), 8.01 (m, 1H), 8.11 (d, 1H).

LCMS: ES$^+$m/z 357 [M+Na]$^+$

EXAMPLE 24

4-(4-Benzyl-5-piperidin-1-ylmethyl-4H-[1,2,4]triazol-3-yl)-3,4,5,6-tetrahydro-2H-[1,2']bipyridinyl

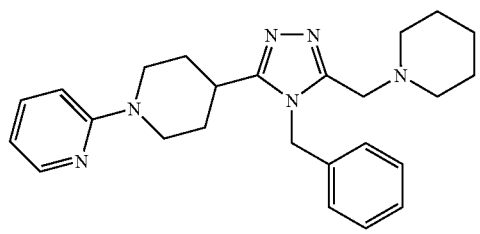

The oxadiazole of Preparation 40 (100 mg, 0.31 mmol), anhydrous magnesium chloride (10 mg, 0.11 mmol) and benzylamine (120 μl, 1.24 mmol) were heated at 150° C. for 18 hours. The reaction mixture was cooled to room temperature and partitioned between dichloromethane and 2 N hydrochloric acid. The acidic solution was washed with dichloromethane (×2) and was basified by addition of solid sodium carbonate. The solid formed was isolated by filtration, washed with water and dried under vacuum to give the title compound as a white solid (100 mg).

$^1$H NMR (400 MHz, CD$_3$OD): δ 1.48 (m, 6H), 1.73 (m, 2H), 1.87 (m, 2H), 2.39 (s, 4H), 2.82 (t, 2H), 2.99 (m, 1H), 3.58 (s, 2H), 4.29 (d, 2H), 5.48 (s, 2H), 6.62 (m, 1H), 6.81 (d, 1H), 7.16 (d, 2H), 7.38 (m, 3H), 7.53 (m, 1H), 8.03 (d, 1H)

LRMS: m/z APCI 377[M+H]$^+$

EXAMPLE 25

(S)-4-[4-(1-Phenyl-ethyl)-5-piperidin-1-ylmethyl-4H-[1,2,4]triazol-3-yl]-3,4,5,6-tetrahydro-2H-[1,2']bipyridinyl

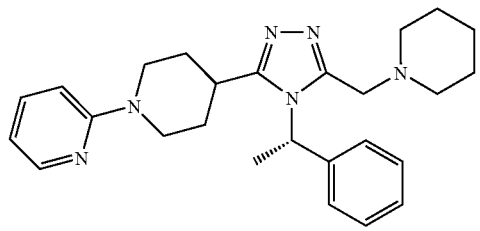

The title compound was obtained from the oxadiazole of Preparation 40 (115 mg, 0.35 mmol) and S-(−)-1-phenyl-ethylamine in 33% yield following the procedure described in Example 24.

$^1$H NMR (400 MHz, CD$_3$OD): (rotamers) δ 1.54 (m, 7H), 1.92 (m, 2H), 1.99 (d, 3H), 2.41 (m, 4H), 2.79 (m, 2H), 3.64 (dd, 2H), 4.05 (d, 2H), 4.33 (d, 2H), 6.08 (q, 1H), 6.62 (m, 1H), 6.79 (d, 1H), 7.40 (m, 5H), 7.51 (m, 1H), 8.01 (d, 1H)

LRMS: m/z APCI 377 [M+H]$^+$

EXAMPLE 26

4-[4-Benzyl-5-(4-methoxy-piperidin-1-ylmethyl)-4H-[1,2,4]triazol-3-yl]-3,4,5,6-tetrahydro-2H-[1,2']bipyridinyl

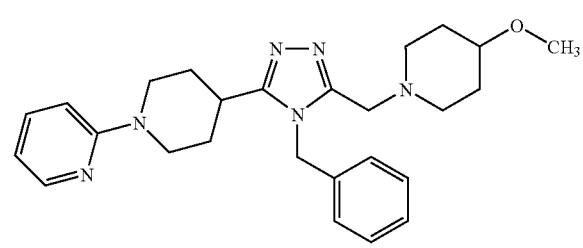

The title compound was obtained from the oxadiazole of Preparation 41 and benzylamine in 39% yield following the procedure described in Example 24.

$^1$H NMR (400 MHz, CD$_3$OD): δ 1.41 (m, 2H), 1.74 (m, 2H), 1.85 (m, 4H), 2.21 (m, 2H), 2.68 (m, 2H), 2.83 (m, 2H), 2.99 (m, 1H), 3.30 (m, 4H), 3.60 (s, 2H), 4.28 (m, 2H), 5.49 (s, 2H), 6.62 (m, 1H), 6.81 (d, 1H), 7.15 (d, 2H), 7.38 (m, 3H) m 7.53 (m, 1H), 8.04 (m, 1H)

LRMS: m/z APCI 447 [M+H]$^+$

EXAMPLE 27

(S)-4-[5-(4-Methoxy-piperidin-1-ylmethyl)-4-(1-phenyl-ethyl)-4H-[1,2,4]triazol-3-yl]-3,4,5,6-tetrahydro-2H-[1,2']bipyridinyl

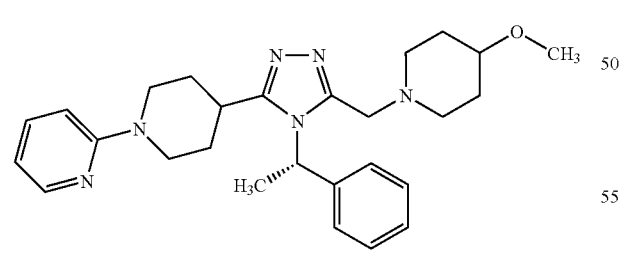

The title compound was obtained from the oxadiazole of Preparation 41 and S-(−)-1-phenylethylamine in 37% yield following the procedure described in Example 24.

$^1$H NMR (400 MHz, CD$_3$OD): δ 0.90 (m, 1H), 1.55 (m, 3H), 1.93 (m, 4H), 1.99 (d, 3H), 2.26 (m, 2H), 2.40 (m, 1H), 2.79 (m, 4H), 3.33 (m, 4H), 3.68 (m, 2H), 4.06 (m, 1H), 4.35 (m, 1H), 6.08 (m, 1H), 6.61 (m, 1H), 6.79 (m, 1H), 7.43 (m, 6H), 8.02 (m, 1H)

LRMS: m/z APCI 461 [M+H]$^+$

EXAMPLE 28

4-[4-Benzyl-5-(3,4,5,6-tetrahydro-2H-[1,2']bipyridinyl-4-yl)-4H-[1,2,4]triazol-3-ylmethyl]-piperazine-1-carboxylic acid benzyl ester

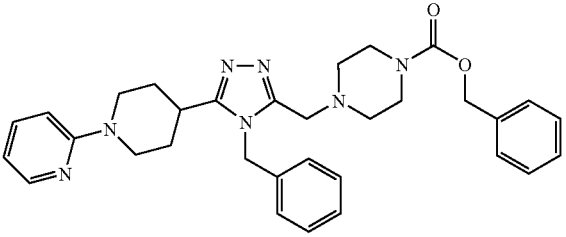

The oxadiazole of Preparation 42 (250 mg, 1.1 mmol), p-toluene sulphonic acid (20 mg) and benzylamine (176 μl, 3.3 mmol) were mixed in xylene (8 ml) and heated at 150° C. for 18 hours. The solvent was evaporated under reduced pressure and the residue was partitioned between ethyl acetate (100 ml) and water (50 ml). The layers were separated and the organic layer was dried over magnesium sulphate and evaporated under reduced pressure. The residue was triturated with diethyl ether to give the title compound as a white solid (155 mg).

$^1$H NMR (400 MHz, CD$_3$OD): δ 1.77 (m, 2H), 1.84 (m, 2H), 2.18 (s, 4H), 2.82 (m, 2H), 3.01 (m, 1H), 3.33 (m, 4H), 3.63 (s, 2H), 4.28 (m, 2H), 5.09 (s, 2H), 5.74 (s, 2H), 6.62 (m, 1H), 6.81 (d, 1H), 7.11 (m, 2H), 7.30 (m, 8H), 7.52 (m, 1H), 8.02 (m, 1H)

LRMS: m/z APCI 461 [M+H]$^+$

EXAMPLE 29

4-[4-Benzyl-5-(2-morpholin-4-yl-ethoxymethyl)-4H-[1,2,4]triazol-3-yl]-3,4,5,6-tetrahydro-2H-[1,2']bipyridinyl

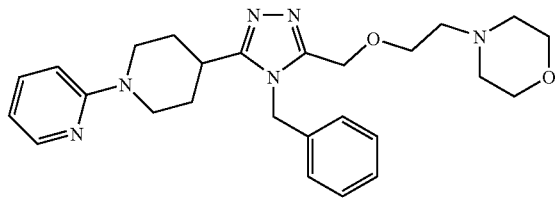

The title compound was obtained from the oxadiazole of Preparation 43 and benzylamine in 37% yield following the procedure described in Example 28.

$^1$H NMR (400 MHz, CD$_3$OD): δ 1.70 (m, 2H), 1.83 (m, 2H), 2.41 (s, 4H), 2.47 (m, 2H), 2.81 (m, 2H), 2.97 (m, 1H), 3.59 (m, 4H), 3.62 (m, 2H), 4.27 (m, 2H), 4.65 (s, 2H), 5.43 (s, 2H), 6.62 (m, 1H), 6.81 (m, d, 1H), 7.16 (m, 2H), 7.38 (m, 3H), 7.53 (m, 1H), 8.04 (d, 1H)

LRMS: m/z APCI 463 [M+H]$^+$

EXAMPLE 30

4-[4-Benzyl-5-{(3R)-3-methoxy-pyrrolidin-1-ylmethyl)-4H-[1,2,4]triazol-3-yl]-3,4,5,6-tetrahydro-2H-[1,2']bipyridinyl

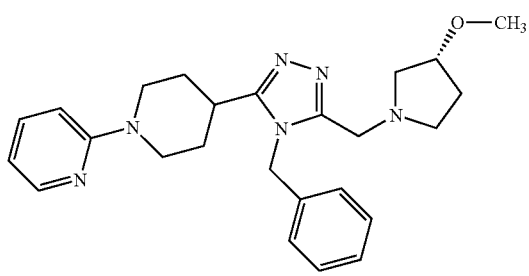

A mixture of the oxadiazole from preparation 55 (250 mg, 0.73 mmol), benzylamine (0.24 ml, 2.19 mmol), and para-toluene sulphonic acid (20 mg) in xylene (2 ml) was heated at 150° C. for 24 hours. The cooled mixture was partitioned between ethyl acetate and saturated sodium bicarbonate solution and the layers separated. The organic phase was dried (MgSO$_4$) and evaporated under reduced pressure. The product was purified by column chromatography on silica gel using an Isolute® cartridge and an elution gradient of ethyl acetate:methanol (100:0 to 98:2) to give the title compound as a white solid, 75 mg.

$^1$H NMR (CD$_3$OD, 400 MHz) δ: 1.68–1.93 (m, 6H), 1.99–2.09 (m, 1H), 2.45 (q, 1H), 2.58-2.74 (m, 3H), 2.78–2.89 (m, 2H), 3.00 (m, 1H), 3.25 (s, 3H), 3.73 (m, 2H), 3.91 (m, 1H), 4.28 (m, 2H), 5.45 (s, 2H), 6.62 (dd, 1H), 6.80 (d, 1H), 7.15 (d, 2H), 7.36 (m, 3H), 7.52 (m, 1H), 8.04 (d, 1H). LRMS: m/z (APCl$^+$) 433 [MH$^+$]

EXAMPLES: 31–39

The following examples of general structure:

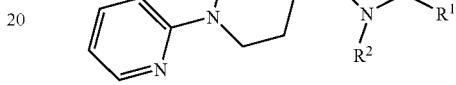

were prepared from the corresponding oxadiazoles and benzylic amine, following a similar procedure to that described in example 30.

TABLE 8

| Ex No | R$^1$ | R$^2$ | Data |
|---|---|---|---|
| 31$^a$ | (3R)-3-methoxy-pyrrolidin-1-yl (CH$_3$O-pyrrolidinyl) | benzyl | $^1$H NMR (CD$_3$OD, 400 MHz) δ: 1.68–1.93 (m, 6H), 2.04 (m, 1H), 2.46 (q, 1H), 2.58–2.73 (m, 3H), 2.83 (m, 2H), 3.01 (m, 1H), 3.25 (s, 3H), 3.73 (m, 2H), 3.91 (m, 1H), 4.28 (m, 2H), 5.46 (s, 2H), 6.63 (dd, 1H), 6.81 (d, 1H), 7.16 (d, 1H), 7.30–7.42 (m, 3H), 7.52 (m, 1H), 8.04 (d, 1H). LRMS: m/z (APCl$^+$) 433 [MH$^+$] |
| 32$^b$ | 3-hydroxy-pyrrolidin-1-yl | benzyl | $^1$H NMR (CD$_3$OD, 400 MHz) δ: 1.64–1.93 (m, 5H), 2.05–2.14 (m, 1H), 2.42–2.53 (m, 2H), 2.69–2.89 (m, 4H), 2.96–3.05 (m, 1H), 3.30 (s, 2H), 3.73 (m, 2H), 4.28 (m, 3H), 6.63 (dd, 1H), 6.81 (d, 1H), 7.14 (d, 1H), 7.30–7.41 (m, 3H), 7.52 (m, 1H), 8.04 (d, 1H). LRMS: m/z (APCl$^+$) 419 [MH$^+$] |
| 33$^c$ | pyrrolidin-1-yl | benzyl | $^1$H NMR (CD$_3$OD, 400 MHz) δ: 1.70–1.92 (m, 9H), 2.49–2.55 (m, 4H), 2.83 (t, 2H), 2.99 (m, 2H), 3.74 (s, 2H), 4.27 (d, 2H), 4.53 (br s, 1H), 6.62 (dd, 1H), 6.81 (d, 1H), 7.14 (d, 2H), 7.30–7.41 (m, 3H), 7.49–7.54 (m, 1H), 8.04 (m, 1H). LRMS: m/z (APCl$^+$) 403 [MH$^+$] |
| 34$^d$ | 2-oxa-5-aza-bicyclic group | benzyl | $^1$H NMR (CD$_3$OD, 400 MHz) δ: 1.68–1.92 (m, 6H), 2.62 (m, 1H), 2.81 (m, 3H), 2.98 (m, 1H), 3.41 (s, 1H), 3.58 (m, 1H), 3.84 (q, 2H), 3.92 (m, 1H), 4.28 (m, 2H), 4.38 (s, 1H), 5.46 (s, 2H), 6.63 (m, 1H), 6.80 (d, 1H), 7.11 (m, 2H), 7.38 (m, 3H), 7.52 (m, 1H), 8.02 (m, 1H). LRMS: m/z (APCl$^+$) 431 [MH$^+$] |

TABLE 8-continued

| Ex No | R¹ | R² | Data |
|---|---|---|---|
| 35[e] | 4-methoxypiperidin-1-yl (N-piperidine with 4-OCH₃) | phenyl-CH₂- | ¹H NMR (CD₃OD, 400 MHz) δ: 1.61 (m, 2H), 1.77 (m, 2H), 1.82 (m, 4H), 2.20 (m, 2H), 2.65 (m, 2H), 2.82 (m, 2H), 2.99 (m, 1H), 3.50 (m, 4H), 3.60 (s, 2H), 4.30 (d, 2H), 5.49 (s, 2H), 6.63 (m, 1H), 6.81 (d, 1H), 7.18 (m, 2H), 7.38 (m, 3H), 7.56 (m, 1H), 8.02 (m, 1H). LRMS: m/z (APCl⁺) 447 [MH⁺] |
| 36[f] | CH₃ | 4-fluorobenzyl | ¹H NMR (CD₃OD, 400 MHz) δ: 1.77–1.92 (m, 4H), 2.35 (s, 3H), 2.88 (m, 2H), 3.01 (m, 1H), 4.29 (m, 2H), 5.29 (s, 2H), 6.63 (m, 1H), 6.82 (d, 1H), 7.12 (m, 4H), 7.52 (m, 1H), 8.04 (d, 1H). LRMS: m/z (APCl⁺) 352 [MH⁺] |
| 37[f] | CH₃ | 3-methoxybenzyl | ¹H NMR (CD₃OD, 400 MHz) δ: 1.78–1.91 (m, 4H), 2.35 (s, 3H), 2.87 (m, 2H), 3.01 (m, 1H), 3.77 (s, 3H), 4.28 (m, 2H), 5.27 (s, 2H), 6.56 (d, 1H), 6.62 (m, 2H), 6.82 (d, 1H), 6.90 (d, 1H), 7.29 (m, 1H), 7.52 (m, 1H), 8.04 (d, 1H). LRMS: m/z (APCl⁺) 364 [MH⁺] |
| 38[f] | CH₃ | 3-methylbenzyl | ¹H NMR (CD₃OD, 400 MHz) δ: 1.73–1.92 (m, 4H), 2.33 (s, 3H), 2.35 (s, 3H), 2.87 (t, 2H), 3.00 (m, 1H), 4.28 (m, 2H), 5.26 (s, 2H), 6.62 (dd, 1H), 6.81 (d, 2H), 6.90 (s, 1H), 7.15 (d, 1H), 7.26 (dd, 1H), 7.52 (dd, 1H), 8.04 (d, 1H). LRMS: m/z (APCl⁺) 348 [MH⁺] |
| 39[f] | CH₃ | 3-chlorobenzyl | ¹H NMR (CD₃OD, 400 MHz) δ: 1.76–1.94 (m, 4H), 2.37 (s, 3H), 2.85–3.07 (m, 3H), 4.31 (br d, 2H), 5.34 (s, 2H), 6.64 (dd, 1H), 6.83 (d, 1H), 6.94 (d, 1H), 7.14 (s, 1H), 7.34–7.41 (m, 2H), 7.53 (m, 1H), 8.04 (m, 1H). LRMS: m/z (APCl⁺) 368 [MH⁺] |

[a] oxadiazole of preparation 54 used as starting material
[b] oxadiazole of preparation 53 used as starting material. An elution gradient of dichloromethane:methanol (100:0 to 95:5) was used as the chromatography solvent.
[c] oxadiazole of preparation 52 used as starting material. The title compound was isolated by trituration from ethyl acetate and then 0.88 ammonia
[d] oxadiazole of preparation 57 used as starting material
[e] oxadiazole of preparation 41 used as starting material
[f] oxadiazole of preparation 27 used as starting material

EXAMPLE 40

N-Benzyl-2-[4-benzyl-5-(3,4,5,6-tetrahydro-2H-[1, 2']bipyridinyl-4-yl)-4H-[1,2,4]triazol-3-yl]-acetamide

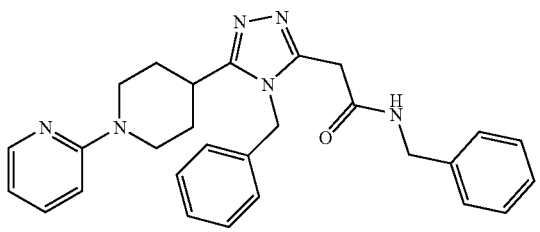

A mixture of the oxadiazole from preparation 45 (630 mg, 1.83 mmol), benzylamine (0.6 ml, 5.49 mmol) and para-toluene sulphonic acid (50 mg) in xylene (5 ml) was heated under reflux for 24 hours. The cooled mixture was evaporated under reduced pressure and the residue purified by column chromatography on silica gel using ethyl acetate: methanol:0.88 ammonia (90:10:1). The product was triturated with ether, and the resulting solid filtered off and dried to afford the title compound as a pink solid, 470 mg.

$^1$H NMR (CD$_3$OD, 400 MHz) δ: 1.75 (m, 2H), 1.84 (m, 2H), 2.81 (m, 2H), 2.97 (m, 1H), 3.77 (s, 2H), 4.36 (m, 2H), 4.30 (s, 2H), 5.41 (s, 2H), 6.61 (m, 1H), 6.80 (d, 1H), 7.17 (d, 2H), 7.30 (m, 8H), 7.50 (m, 1H), 8.02 (d, 1H).

LRMS: m/z (APCI$^+$) 467 [MH$^+$]

EXAMPLE 41

2-[4-Benzyl-5-(3,4,5,6-tetrahydro-2H-[1,2']bipyridinyl-4-yl)-4H-[1,2,4]triazol-3-ylmethoxy]-ethylamine

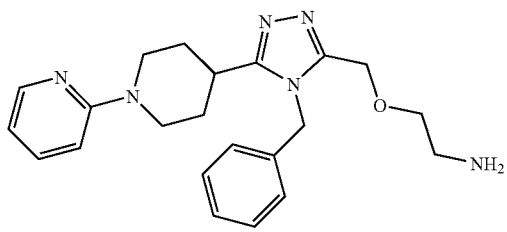

Trifluoroacetic acid (2 ml) was added to a solution of the protected amine from preparation 69 (100 mg, 0.02 mmol) in dichloromethane (2 ml), and the reaction stirred at room temperature for 2 hours. The reaction was concentrated under reduced pressure and the residue partitioned between ethyl acetate and aqueous sodium carbonate solution. The layers were separated, the organic phase dried (MgSO$_4$), evaporated under reduced pressure and the product triturated with ether to afford the title compound as a solid, 39 mg.

$^1$H NMR (CD$_3$OD, 400 MHz) δ: 1.72 (m, 2H), 1.87 (m, 2H), 2.82 (m, 4H), 3.00 (m, 1H), 3.52 (t, 2H), 4.27 (m, 2H), 4.65 (s, 2H), 5.41 (s, 2H), 6.63 (m, 1H), 6.81 (d, 1H), 7.17 (m, 2H), 7.37 (m, 3H), 7.51 (m, 1H), 8.03 (m, 1H).

LRMS: m/z (APCI$^+$) 393 [MH$^+$]

EXAMPLE 42

[4-Benzyl-5-(3,4,5,6-tetrahydro-2H-[1,2']bipyridinyl-4-yl)-4H-[1,2,4]triazol-3-ylmethyl]-ethyl-amine

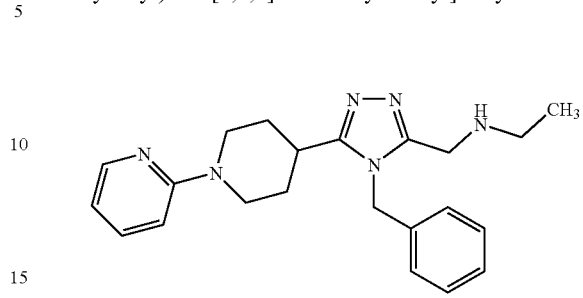

The title compound was obtained, after trituration from ethyl acetate, as a white solid, from the protected amine from preparation 66, according to the method described in example 41.

$^1$H NMR (CD$_3$OD, 400 MHz) δ: 1.08 (t, 3H), 1.71–1.89 (m, 4H), 2.64 (br s, 2H), 2.85 (q, 2H), 3.01 (m, 1H), 3.88 (m, 2H), 4.27 (m, 2H), 5.44 (d, 2H), 6.92 (m, 1H), 6.80 (m, 1H), 7.10 (m, 1H), 7.31–7.40 (m, 3H), 7.51 (m, 1H), 8.02 (m, 1H).

LRMS: m/z (APCI$^+$) 377 [MH$^+$]

EXAMPLE 43

[4-Benzyl-5-(3,4,5,6-tetrahydro-2H-[1,2']bipyridinyl-4-yl)-4H-[1,2,4]triazol-3-ylmethyl]-(2-methoxyethyl)-amine

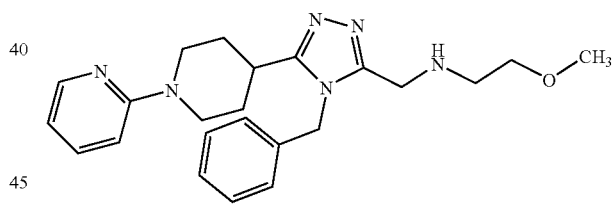

A solution of the protected amine from preparation 67 (170 mg, 0.34 mmol) in dichloromethane (2 ml) and trifluoroacetic acid (2 ml) was stirred at room temperature for 2 hours. The reaction was concentrated under reduced pressure and the residual oil was partitioned between dichloromethane and aqueous sodium carbonate solution. The layers were separated, and the organic phase dried (MgSO$_4$) and evaporated under reduced pressure. The product was purified by column chromatography on silica gel using dichloromethane:methanol:0.88 ammonia (95:5:0.5), and the product triturated from ether to afford the title compound as a white solid, 70 mg.

$^1$H NMR (CD$_3$OD, 400 MHz) δ: 1.73 (m, 2H), 1.85 (m, 2H), 2.72 (t, 2H), 2.83 (m, 2H), 3.00 (m, 1H), 3.30 (s, 3H), 3.41 (t, 2H), 3.87 (s, 2H), 4.27 (m, 2H), 5.45 (s, 2H), 6.61 (m, 1H), 6.80 (d, 1H), 7.13 (d, 2H), 7.36 (m, 3H), 7.53 (m, 1H), 8.03 (d, 1H).

LRMS: m/z (APCI$^+$) 407 [MH$^+$]

EXAMPLE 44

[4-Benzyl-5-(3,4,5,6-tetrahydro-2H-[1,2']bipyridinyl-4-yl)-4H-[1,2,4]triazol-3-ylmethyl]-(3-methoxypropyl)-amine

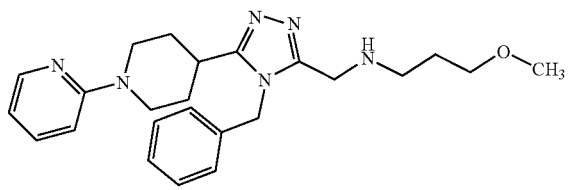

The title compound was obtained as a white solid from the protected amine from preparation 68, following a similar procedure to that described in example 43.

$^1$H NMR (CD$_3$OD, 400 MHz) δ: 1.65–1.76 (m, 4H), 1.81–1.92 (m, 2H), 2.64 (t, 2H), 2.84 (m, 2H), 3.00 (m, 1H), 3.27 (s, 3H), 3.40 (t, 2H), 3.86 (s, 2H), 4.27 (m, 2H), 5.45 (s, 2H), 6.62 (m, 1H), 6.81 (d, 1H), 7.32–7.41 (m, 3H), 7.52 (m, 1H), 8.04 (d, 1H).

LRMS: m/z (APCI$^+$) 421 [MH$^+$]

EXAMPLE 45

1-{4-[4-Benzyl-5-(3,4,5,6-tetrahydro-2H-[1,2']bipyridinyl-4-yl)-4H-[1,2,4]triazol-3-ylmethyl]-piperazin-1-yl}-ethanone

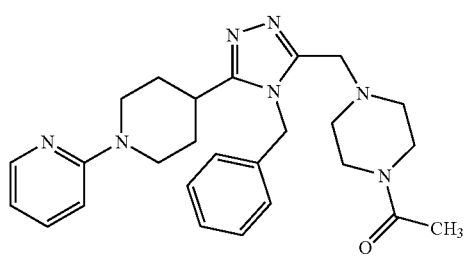

Acetyl chloride (12 μl, 1.58 mmol) was added to a solution of the piperazine from preparation 72 (55 mg, 1.32 mmol) and triethylamine (23 μl, 1.58 mmol) in dichloromethane (1 ml) and the reaction stirred at room temperature for 2.5 hours. The mixture was concentrated under reduced pressure and the residue partitioned between ethyl acetate and sodium bicarbonate solution. The layers were separated, the organic phase dried (MgSO$_4$) and evaporated under reduced pressure. The product was triturated with ether, and the resulting solid filtered and dried to afford the title compound as a white solid, 46 mg.

$^1$H NMR (CD$_3$OD, 400 MHz) δ: 1.75–1.95 (m, 4H), 2.06 (s, 3H), 2.39 (t, 2H), 2.44 (t, 2H), 2.85 (t, 2H), 3.00 (m, 1H), 3.36 (t, 2H), 3.41 (t, 2H), 3.67 (s, 2H), 4.29 (br d, 2H), 5.48 (s, 2H), 6.63 (dd, 1H), 6.81 (d, 1H), 7.13 (d, 2H), 7.53 (t, 1H), 8.04 (d, 1H).

LRMS: m/z (APCI$^+$) 460 [MH$^+$]

EXAMPLE 46

4-[4-Benzyl-5-(4-methanesulfonyl-piperazin-1-ylmethyl)-4H-[1,2,4]triazol-3-yl]-3,4,5,6-tetrahydro-2H-[1,2]bipyridinyl

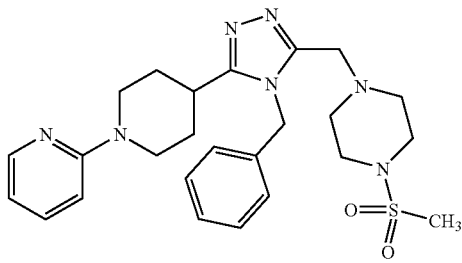

Methane sulphonyl chloride (13 μl, 0.17 mmol) was added to a solution of the piperazine from preparation 72 (59 mg, 0.14 mmol), and triethylamine (241, 0.17 mmol) in dichloromethane (0.5 ml) and the solution stirred at room temperature for 2.5 hours. The mixture was concentrated under reduced pressure and the residue partitioned between ethyl acetate and sodium bicarbonate solution. The layers were separated, and the organic phase evaporated under reduced pressure to afford the title compound as a white solid, 68 mg.

$^1$H NMR (CD$_3$OD, 400 MHz) δ: 1.78–1.97 (m, 4H), 2.51 (t, 4H), 2.75 (s, 3H), 2.85 (t, 2H), 2.99 (m, 5H), 3.69 (s, 2H), 4.30 (d, 2H), 5.46 (s, 2H), 6.63 (dd, 1H), 6.82 (d, 1H), 7.11 (d, 2H), 7.30–7.43 (m, 3H), 7.53 (m, 1H), 8.04 (d, 1H).

LRMS: m/z (APCI$^+$) 496 [MH$^+$]

EXAMPLE 47

N-[4-Benzyl-5-(3,4,5,6-tetrahydro-2H-[1,2']bipyridinyl-4-yl)-4H-[1,2,4]triazol-3-ylmethyl]-methanesulfonamide

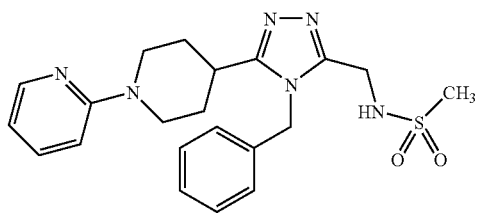

N,N-Diisopropylethylamine (61 μl, 0.35 mmol), followed by methane sulphonyl chloride (28 μl, 0.35 mmol) was added to a solution of the amine from preparation 71 (100 mg, 0.29 mmol) in dichloromethane (1.5 ml) and the reaction stirred at room temperature for 4 hours. The reaction mixture was filtered, and the collected solid washed with water and dichloromethane, and dried to afford the title compound as a white solid, 59 mg.

$^1$H NMR (DMSOd$_6$, 400 MHz) δ: 1.57–1.69 (m, 4H), 2.80 (m, 2H), 2.92 (s, 3H), 2.96 (m, 1H), 4.25 (m, 4H), 5.34 (s, 2H), 6.58 (m, 1H), 6.80 (d, 1H), 7.09 (d, 2H), 7.29–7.39 (m, 3H), 7.47 (m, 1H), 7.68 (dd, 1H), 8.06 (d, 1H).

LRMS: m/z (APCI$^+$) 427 [MH$^+$]

EXAMPLE 48

[4-Benzyl-5-(3,4,5,6-tetrahydro-2H-[1,2']bipyridinyl-4-yl)-4H-[1,2,4]triazol-3-ylmethyl]-(2-methoxyethyl)-methyl-amine

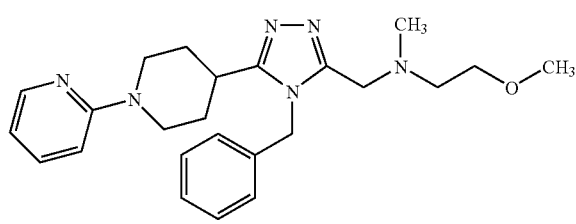

The amine from example 43 (50 mg, 0.12 mmol), formaldehyde (37% aq, 40 µl, 0.49 mmol) and sodium triacetoxyborohydride (51 mg, 0.24 mmol) in dichloromethane (1 ml) was stirred vigorously at room temperature for 21 hours. The reaction mixture was partitioned between dichloromethane and aqueous sodium carbonate solution, and the layers separated. The organic phase was dried (MgSO$_4$), evaporated under reduced pressure, and the product triturated from ether to afford the title compound as a white solid.

$^1$H NMR (CD$_3$OD, 400 MHz) δ: 1.76–1.90 (m, 2H), 2.23 (s, 3H), 2.61 (t, 2H), 2.81 (m, 2H), 2.98 (m, 1H), 3.19 (s, 3H), 3.43 (t, 2H), 3.69 (s, 2H), 4.26 (m, 2H), 5.53 (s, 2H), 6.63 (m, 1H), 6.80 (d, 1H), 7.13 (d, 2H), 7.31–7.41 (m, 3H), 7.52 (m, 1H), 8.04 (d, 1H).

LRMS: m/z (APCI$^+$) 421 [MH$^+$]

EXAMPLE 49

[4-Benzyl-5-(3,4,5,6-tetrahydro-2H-[1,2']bipyridinyl-4-yl)-4H-[1,2,4]triazol-3-ylmethyl]-(3-methoxypropyl)-methyl-amine

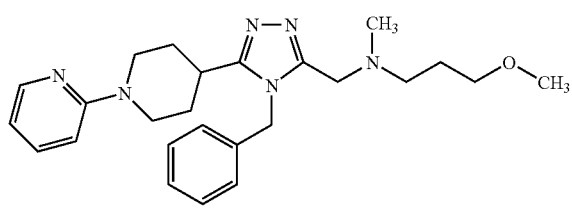

The title compound was obtained as a white solid in 60%, from the amine from example 44 and formaldehyde, following the procedure described in example 48.

$^1$H NMR (CD$_3$OD, 400 MHz) δ: 1.68 (m, 2H), 1.83 (m, 2H), 2.17 (s, 3H), 2.47 (t, 2H), 2.80 (m, 2H), 2.96 (m, 1H), 3.15 (s, 3H), 3.35 (t, 2H), 3.60 (s, 2H), 4.26 (m, 2H), 5.28 (s, 2H), 6.61 (m, 1H), 6.81 (d, 1H), 7.12 (d, 2H), 7.36 (m, 3H), 7.54 (m, 1H), 8.03 (d, 1H).

LRMS: m/z (APCI$^+$) 435 [MH$^+$]

EXAMPLE 50

4-(4-Benzyl-5-morpholin-4-ylmethyl-4H-[1,2,4]triazol-3-yl)-3'-methyl-3,4,5,6-tetrahydro-2H-[1,2']bipyridinyl

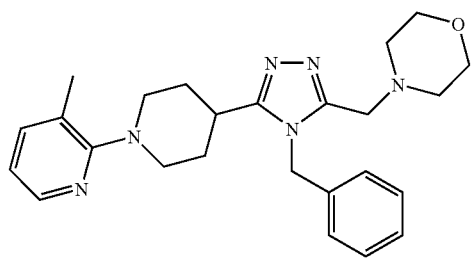

2-Bromo-3-methylpyridine (66 µl, 0.6 mmol) was added to a mixture of the piperidine from Preparation 77 (200 mg, 0.6 mmol), sodium tert-butoxide (70 mg, 0.72 mmol) (+/−) 2,2'-bis(diphenylphosphino)-1,1'-binaphthyl, (15 mg, 0.024 mmol) and tris(dibenzylideneacetone)dipalladium (11 mg, 0.012 mmol) in toluene (8 ml) and the mixture was stirred at 100° C. for 18 hours. The reaction mixture was cooled to room temperature and evaporated under reduced pressure. The residue was partitioned between sodium carbonate solution (20 ml) and dichloromethane (20 ml). The aqueous solution was extracted with dichloromethane (2×20 ml) and the combined organic solutions were washed with brine, dried over magnesium sulphate and evaporated under reduced pressure. The residue was purified by chromatography on silica gel using methanol:dichloromethane:0.88 ammonia as eluant (5:95:0.5) to give the title compound (80 mg).

$^1$H NMR (400 MHz, CD$_3$OD): δ 1.78 (d, 2H), 2.05 (q, 2H), 2.25 (s, 3H), 2.42 (m, 4H), 2.75 (t, 2H), 2.95 (m, 1H), 3.35 (s, 2H), 3.40–3.60 (m, 4H), 3.65 (s, 2H), 5.45 (s, 2H), 6.95 (m, 1H), 7.15 (d, 2H), 7.35–7.60 (m, 4H), 8.05 (m, 1H).

LCMS: m/z APCI$^+$ 433 [MH]$^+$, 455 [MNa]$^+$

EXAMPLE 51

4-(4-Benzyl-5-morpholin-4-ylmethyl-4H-[1,2,4]triazol-3-yl)-3'-trifluoromethyl-3,4,5,6-tetrahydro-2H-[1,2']bipyridinyl

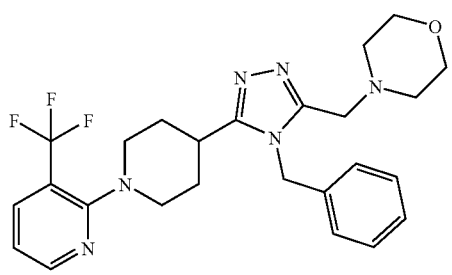

The title compound was prepared from the piperidine of preparation 77 and 2-chloro-3-trifluoromethylpyridine in a 21% yield, as a white foam, using a method similar to that described in preparation 50.

¹H NMR (400 MHz, CD₃OD): δ 1.75 (d, 2H), 2.05 (q, 2H), 2.42 (m, 4H), 2.95 (m, 3H), 3.15–3.60 (m, 6H), 3.64 (s, 2H), 5.42 (s, 2H), 7.05 (m, 3H), 7.15–7.25 (m, 3H), 8.05 (m, 1H), 8.42 (s, 1H)
LCMS: m/z APCI⁺ 487 [MH]⁺

EXAMPLE 52

4-(4-Benzyl-5-morpholin-4-ylmethyl-4H-[1,2,4]triazol-3-yl)-3,4,5,6-tetrahydro-2H-[1,2']bipyridinyl-3'-carbonitrile

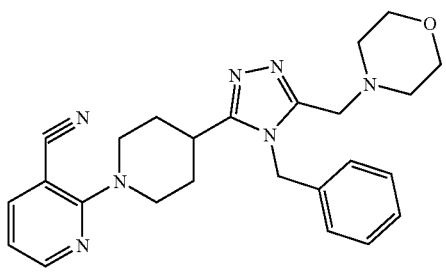

The piperidine of Preparation 77 (400 mg, 1.17 mmol) was mixed with 2-chloro-3-cyanopyrimidine (325 mg, 2.43 mmol) and potassium carbonate (323 mg, 2.43 mmol) in 1-methy-2-lpyrrolidinone (3 ml) and was heated at 100° C. for 18 hours. The reaction mixture was cooled to room temperature and was partitioned between water and dichloromethane. The aqueous phase was extracted with dichloromethane and the combined organic phases were washed with brine, dried over magnesium sulphate and evaporated under reduced pressure. The residue was purified by chromatography on silica gel using methanol and ammonium hydroxide in dichloromethane as eluant (5:0.5:95) to give the title compound as a pale yellow foam (395 mg).
¹H NMR (400 MHz, CD₃OD): δ 1.78 (d, 2H), 1.95 (q, 2H), 2.40 (m, 4H), 2.95 (m, 3H), 3.50 (s, 4H), 3.60 (s, 2H), 4.35 (d, 2H), 5.50 (s, 2H), 6.90 (m, 1H), 7.10 (d, 2H), 7.20–7.40 (m, 3H), 7.90 (d, 1H), 8.30 (d, 1H)
LCMS: m/z APCI⁺ 444 [MH]⁺

EXAMPLE 53

4-(4-Benzyl-5-morpholin-4-ylmethyl-4H-[1,2,4]triazol-3-yl)-3,4,5,6-tetrahydro-2H-[1,2']bipyridinyl-3'-carboxylic acid amide

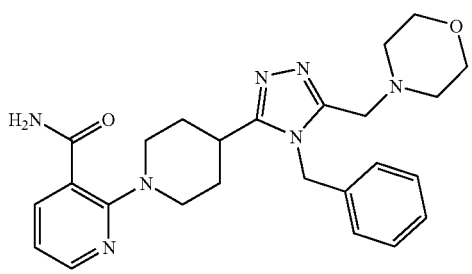

Powdered potassium hydroxide (95 mg, 1.68 mmol) was added to a solution of the carbonitrile of example 52 (250 mg, 0.56 mmol) in 2-Methyl-propan-2-ol (10 ml). The mixture was heated at 100° C. for 18 hr before evaporating under reduced pressure. The residue was purified by chromatography on silica gel using methanol and ammonium hydroxide in dichloromethane (5:0.5:95) as eluant to give the title compound (220 mg), as a white solid
¹H NMR (400 MHz, CD₃OD): δ 1.75 (d, 2H), 2.05 (q, 2H), 2.40 (m, 4H), 2.92 (m, 3H), 3.50 (s, 4H), 3.65 (s, 2H), 3.70 (d, 2H), 5.45 (s, 2H), 6.95 (m, 1H), 7.10 (d, 2H), 7.20–7.40 (m, 3H), 7.95 (d, 1H), 8.25 (d, 1H)
LCMS: m/z APCI⁺, 462 [MH]⁺

EXAMPLE 54

(S)-4-[4-(1-Phenyl-ethyl)-5-(4-pyridin-2-yl-piperazin-1-ylmethyl)-4H-[1,2,4]triazol-3-ylmethyl]-morpholine trihydrochloride

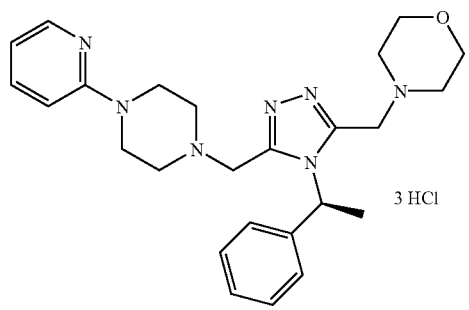

The title compound was prepared from the oxadiazole of preparation 80 by a method similar to that described for example 28 except the compound was purified by chromatography on silica gel using methanol in dichloromethane (5:95) as eluant. The residue was dissolved in dichloromethane (2 ml) and hydrochloric acid (1M in diethyl ether, 2 ml) added and solvents evaporated under reduced pressure to give the title compound as a brown foam (67%).
¹H NMR (400 MHz, CDCl₃): δ 2.00 (m, 5H), 2.40 (m, 2H), 2.45 (m, 4H), 2.55 (m, 2H), 3.25 (m, 2H), 3.45 (m, 5H), 3.50 (m, 2H), 3.65 (m, 4H), 6.10 (q, 1H), 6.60 (m, 2H), 7.25 (m, 2H), 7.35 (m, 2H), 7.45 (m, 1H), 8.20 (m, 1H).
LCMS: m/z ES⁺ 470 [M+Na]⁺

EXAMPLE 55

(S)-4-[4-(1-Phenyl-ethyl)-5-(4-pyrimidin-2-yl-piperazin-1-ylmethyl)-4H-[1,2,4]triazol-3-ylmethyl]-morpholine trihydrochloride

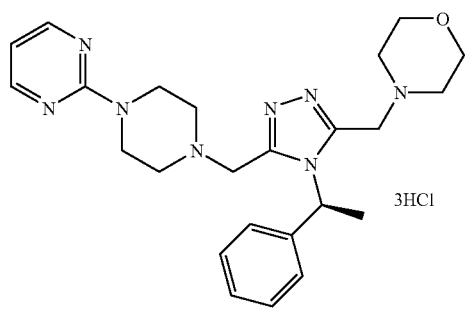

The title compound was prepared from the oxadiazole of preparation 81 by a method similar to that described for example 28 except the compound was purified by chromatography on silica gel using methanol in dichloromethane (5:95) as eluant. The residue was dissolved in dichloromethane (2 ml) and hydrochloric acid (1M in diethyl ether, 2 ml) added and solvents evaporated under reduced pressure to give the title compound as a brown foam (77%).

$^1$H NMR (400 MHz, CD$_3$OD): δ 2.00 (d, 3H), 3.40 (m, 6H), 3.95 (m, 4H), 4.10 (m, 3H), 4.25 (m, 2H), 4.60 (m, 2H), 4.80 (s, 4H), 6.00 (q, 1H), 6.85 (t, 1H), 7.35 (m, 1H), 7.45 (m, 3H), 8.50 (d, 2H)

LCMS: m/z ES$^+$ 449 [M+H]$^+$

EXAMPLE 56

1-[4-Benzyl-5-(1-pyrimidin-2-yl-piperidin-4-yl)-4H-[1,2,4]triazol-3-ylmethyl]-piperidin-3-ol

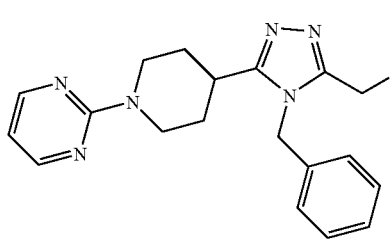

The title compound was prepared from the oxadiazole of preparation 82 by a method similar to that described for example 28 except the compound was purified by chromatography on silica gel using methanol in dichloromethane (5:95) as eluant.

$^1$H NMR (400 MHz, d$_6$-DMSO): δ 1.00 (1H, m), 1.97 (1H, m), 1.24–1.78 (7H, m), 1.83 (1H, br t), 2.51 (1H, br d), 2.70 (1H, br d), 2.81–3.02 (3H, m), 3.22 (1H, m), 3.43 (2H, ABq), 4.51 (1H, d), 4.60 (2H, br d), 5.31 (2H, s), 6.60 (1H, s), 7.11 (2H, d), 7.29 (1H, m), 7.36 (2H, m), 8.36 (2H, d).

LCMS: m/z ES$^+$ 434 [M+H]$^+$

Found; C, 65.32; H, 7.36; N, 22.06%; C$_{22}$H$_{27}$N$_5$O. ½ H$_2$O requires; C, 65.14; H, 7.29; N, 22.15%.

EXAMPLE 57

(R)-2-[4-Benzyl-5-(3,4,5,6-tetrahydro-2H-[1,2']bipyridinyl-4-yl)-4H-[1,2,4]triazol-3-yl]-pyrrolidine-1-carboxylic acid tert-butyl ester

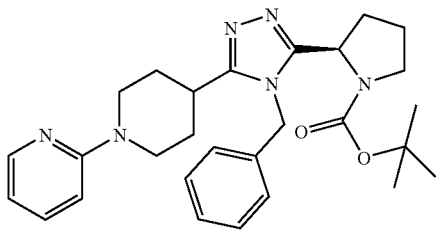

The title compound was prepared from the oxadiazole of preparation 84 by a method similar to that described for example 28 except the compound was purified by chromatography on silica gel using methanol and ammonium hydroxide in dichloromethane (5:0.5:95) as eluant. The material obtained was triturated with ether to give the title compound as an off white solid (60%).

$^1$H NMR (400 MHz, CDCl$_3$): δ 1.12–1.46 (m, 9H), 1.72–2.20 (m, 7H), 2.55 (m, 1H), 2.80 (m, 1H), 3.00 (m, 2H), 3.42 (m, 1H), 3.56 (m, 1H), 4.34 (m, 2H), 4.79 (s, 1H), 5.18–5.32 (m, 1H), 5.67 (d, 1H), 6.60 (t, 1H), 6.68 (d, 1H), 6.97 (d, 2H), 7.33 (m, 3H), 7.48 (bt, 1H), 8.16 (d, 1H)

LCMS: m/z ES$^+$ 489 [M+H]$^+$, 512 [M+Na]$^+$

EXAMPLE 58

(R)-4-[4-Benzyl-5-(tetrahydro-furan-3-yloxymethyl)-4H-[1,2,4]triazol-3-yl]3,4,5,6-tetrahydro-2H-[1,2']bipyridinyl

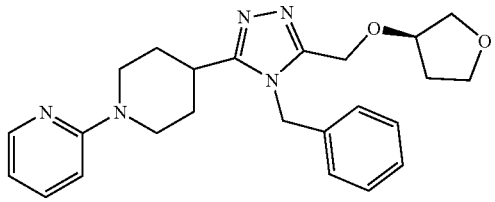

The title compound was prepared from the oxadiazole of preparation 85 by a method similar to that described for example 28 except the compound was purified by chromatography on silica gel using methanol and ammonium hydroxide in dichloromethane (5:0.5:95) as eluant.

$^1$H NMR (400 MHz, CDCl$_3$): δ 1.80 (m, 2H), 1.92 (m, 2H), 2.05 (m, 2H), 2.80 (m, 1H), 2.85 (m, 2H), 3.64 (m, 2H), 3.79 (m, 2H), 4.20 (m, 1H), 4.35 (d, 2H), 4.60 (q, 2H), 5.25 (s, 2H), 6.60 (m, 1H), 6.65 (d, 1H), 7.01 (d, 2H), 7.40 (m, 3H), 7.45 (t, 1H), 8.13 (m, 1H).

LCMS: m/z ES$^+$ 420 [M+H]$^+$

EXAMPLE 59

(S)-4-[4-Benzyl-5-(tetrahydro-furan-3-yloxymethyl)-4H-[1,2,4]triazol-3-yl]3,4,5,6-tetrahydro-2H-[1,2']bipyridinyl

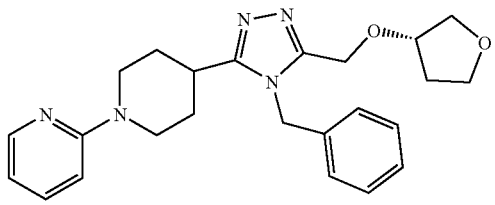

The title compound was prepared from the oxadiazole of preparation 86 by a method similar to that described for example 28 except the compound was purified by trituration with diethyl ether in ethyl acetate (1:1) to give the title compounds as a buff solid (56%).

$^1$H NMR (400 MHz, CDCl$_3$): δ 1.80 (m, 2H), 1.90 (m, 2H), 2.05 (m, 2H), 2.80 (m, 1H), 2.85 m, 2H), 3.65 (m, 2H), 3.80 (m, 2H), 4.20 (m, 1H), 4.35 (d, 2H), 4.60 (q, 2H), 5.25

(s, 2H), 6.60 (m, 1H), 6.65 (d, 1H), 7.00 (d, 2H), 7.40 (m, 3H), 7.45 (t, 1H), 8.15 (m, 1H).

LCMS: m/z ES⁺ 420 [M+H]⁺

EXAMPLE 60

{[4-Benzyl-5-(3,4,5,6-tetrahydro-2H-[1,2']bipyridinyl-4-yl)-4H-[1,2,4]triazol-3-ylmethyl]-methylamino}-acetic acid tert-butyl ester

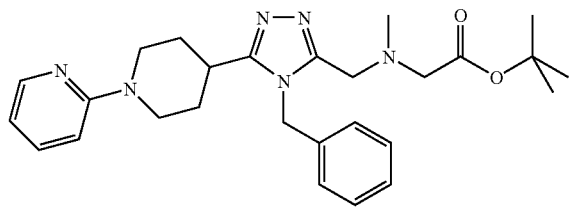

The title compound was prepared from the oxadiazole of preparation 87 by a method similar to that described for example 28 except the compound was purified by chromatography on silica gel using methanol and ammonium hydroxide in dichloromethane (5:0.5:95) as eluant. Material obtained was triturated with diethyl ether in ethyl acetate (1:1) to give the title compound as a white solid (35%).

¹H NMR (400 MHz, CDCl₃): δ 1.42 (s, 9H), 1.82 (bd, 2H), 2.05 (m, 2H), 2.31 (s, 3H), 3.76-3.94 (m, 3H), 3.16 (s, 2H), 3.72 (s, 2H), 4.37 (d, 2H), 5.47 (s, 2H), 6.60 (m, 1H), 6.68 (d, 1H), 7.01 (d, 2H), 7.35 (m, 3H), 7.50 (bt, 1H), 8.18 (d, 1H)

LCMS: m/z ES⁺ 478 [M+H]⁺

EXAMPLE 61

4-[4-Benzyl-5-(tetrahydro-pyran-4-ylmethyl)-4H-[1,2,4]triazol-3-yl]-3,4,5,6-tetrahydro-2H-[1,2']bipyridinyl

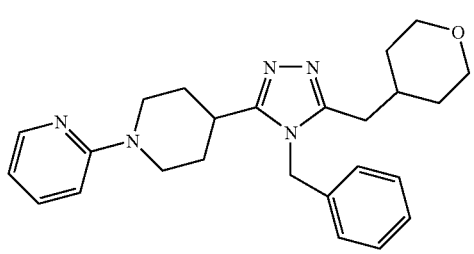

The title compound was prepared from the oxadiazole of preparation 91 by a method similar to that described for example 28 except the compound was purified by chromatography on silica gel using methanol and ammonium hydroxide in dichloromethane (5:0.5:95) as eluant. Material obtained was triturated with diethyl ether to give the title compound as a buff solid (27%).

¹H NMR (400 MHz, CDCl₃): 1.29 (d, 2H), 1.64 (d, 2H), 1.82 (s, 2H) 2.02 (m, 3H), 2.52 (d, 2H), 2.77 (s, 1H), 2.87 (t, 1H), 3.29 (t, 2H), 3.88 (d, 2H), 4.24 (d, 2H), 5.09 (s, 2H), 6.60 (s, 1H), 6.65 (d, 1H), 6.83 (s, 2H), 7.12–7.58 (m, 4H), 8.16 (s, 1H).

All peaks broadened.

MS: m/z ES⁺ 418 [M+H]⁺

EXAMPLE 62

4-[4-Benzyl-5-(tetrahydro-furan-2-yl)-4H-[1,2,4]triazol-3-yl]-3,4,5,6-tetrahydro-2H-[1,2']bipyridinyl

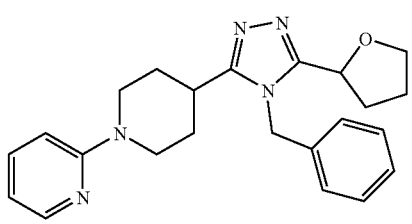

The title compound was prepared from the oxadiazole of preparation 89 by a method similar to that described for example 28 except the compound was purified by trituration with diethyl ether in pentane (1:1) to give the title compound as a buff solid (73%).

¹H NMR (400 MHz, d₄-MeOH): δ 1.68 (2H, dd), 1.84 (2H, m), 2.06 (2H, m), 2.23 (1H, q), 2.57 (1H, m), 2.81 (2H, q), 2.96 (1H, m), 3.87 (2H, m), 4.26 (2H, m), 5.00 (1H, t), 5.46 (2H, d), 6.62 (1H, dd), 6.80 (1H, d), 7.18 (2H, d), 7.37 (3H, m), 7.52 (1H, t), 8.03 (1H, d). LCMS: m/z ES⁺ 390 [M+H]⁺

EXAMPLE 63

4-(4-Benzyl-5-ethoxymethyl-4H-[1,2,4]triazol-3-yl)-3,4,5,6-tetrahydro-2H-[1,2']bipyridinyl

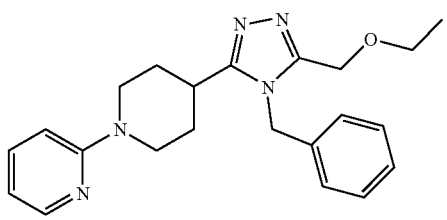

The title compound was prepared from the oxadiazole of preparation 92 by a method similar to that described for example 28 except the compound was purified by chromatography on silica gel eluting with ethyl acetate followed by a gradient of methanol in dichloromethane (2 to 5% methanol) to give the title compound as a buff solid (36%). 25 ¹H NMR (400 MHz, CDCl₃): δ 1.13 (3H, t), 1.84 (2H, br d), 2.05 (2H, dq), 2.82 (1H, t), 1.97 (2H, bt), 3.51 (2H, q), 4.34 (2H, d), 4.58 (2H, s), 5.27 (2H, s), 6.63 (1H, t), 6.71 (1H, d), 7.02 (2H, d), 7.25 (3H, m), 7.52 (1H, t), 8.16 (2H, d).

LCMS: m/z ES⁺ 378 [M+H]⁺

EXAMPLE 64

4-[4-Benzyl-5-(2-methoxy-ethoxymethyl)-4H-[1,2,4]triazol-3-yl]-3,4,5,6-tetrahydro-2H-[1,2']bipyridinyl

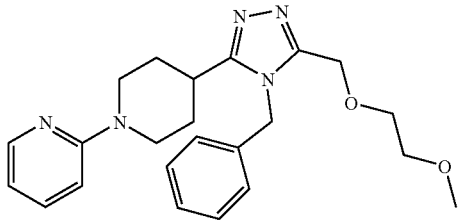

The title compound was prepared from the oxadiazole of preparation 93 by a method similar to that described for example 28 except the compound was purified by chromatography on silica gel eluting with ethyl acetate followed by methanol in dichloromethane (5:95). The material obtained was then triturated with diethyl ether to give the title compound as a white solid (60%).

$^1$H NMR (400 MHz, CDCl$_3$): 1.80 (bd, 2H), 2.06 (dq, 2H), 2.78 (m, 1H), 2.87 (dt, 2H), 3.33 (s, 3H), 3.46 (t, 2H), 4.34 (t, 2H), 4.62 (s, 2H), 5.29 (s, 2H), 6.59 (dd, 1H), 6.65 (d, 1H), 7.03 (d, 2H), 7.36 (m, 3H), 7.45 (t, 1H), 8.15 (d, 1H).

MS: m/z ES$^+$ 408 [M+H]$^+$

EXAMPLE 65

[4-Benzyl-5-(3,4,5,6-tetrahydro-2H-[1,2']bipyridinyl-4-yl)-4H-[1,2,4]triazol-3-ylmethoxy)-acetic acid tert-butyl ester

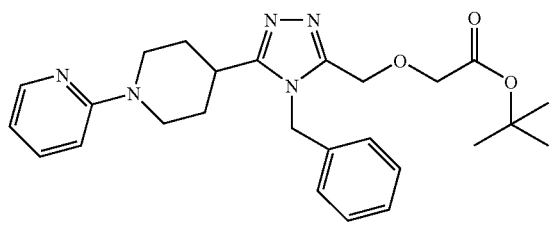

The title compound was prepared from the oxadiazole of preparation 94 by a method similar to that described for example 28 except the compound was purified by chromatography on silica gel eluting with ethyl acetate followed by methanol in dichloromethane (5:95). The material obtained was then triturated with diethyl ether to give the title compound as a buff solid (25%).

$^1$H NMR (400 MHz, CDCl$_3$): 1.43 (s, 9H), 1.82 (bd, 2H), 2.04 (dq, 2H), 2.80 (m, 1H), 2.96 (bt, 2H), 3.98 (s, 2H), 4.34 (bd, 2H), 4.67 (s, 2H), 5.39 (s, 2H), 6.61 (t, 1H), 6.70 (d, 1H), 7.05 (d, 2H), 7.27–7.40 (m, 3H), 7.53 (t, 1H), 8.17 (d, 1H).

MS: m/z ES$^+$ 464 [M+H]$^+$

EXAMPLE 66

N-Benzyl-2-[4-benzyl-5-(3,4,5,6-tetrahydro-2H-[1,2']bipyridinyl-4-yl)-4H-[1,2,4]triazol-3-ylmethoxy]-acetamide

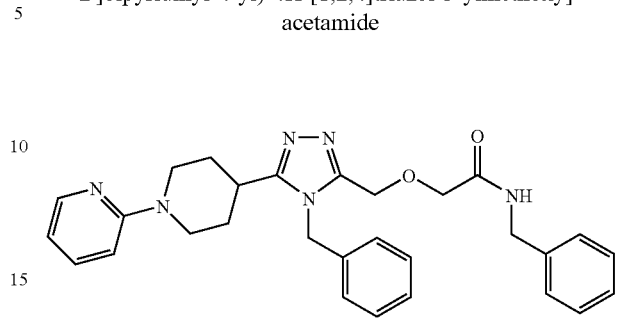

The title compound was prepared from the oxadiazole of preparation 94 by a method similar to that described for example 28 except the compound was purified by chromatography on silica gel eluting with ethyl acetate followed by methanol in dichloromethane (5:95). The material obtained was then triturated with diethyl ether to give the title compound as a white solid (27%).

$^1$H NMR (400 MHz, CDCl$_3$): 1.81 (bd, 2H), 2.04 (dq, 2H), 2.75 (m, 1H), 2.86 (dt, 2H), 3.87 (s, 2H), 4.00 (s, 2H), 4.35 (bd, 2H), 4.64 (s, 2H), 5.20 (s, 2H), 6.48 (bt, 1H), 6.59 (dd, 1H), 6.64 (d, 1H), 6.93 (d, 2H), 7.19–7.38 (m, 8H), 7.45 (t, 1H), 8.16 (d, 1H).

MS: m/z ES$^+$ 497 [M+H]$^+$

EXAMPLE 67

4-(4-Benzyl-5-methylsulfanylmethyl-4H-[1,2,4]triazol-3-yl)-3,4,5,6-tetrahydro-2H-[1,2']bipyridinyl

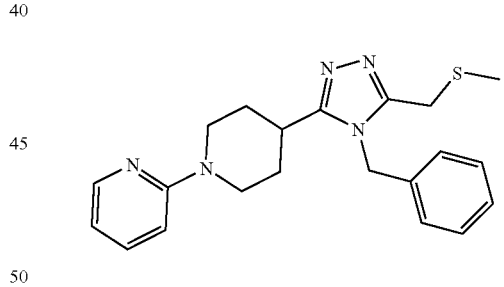

The title compound was prepared from the oxadiazole of preparation 95 by a method similar to that described for example 28 except the compound was purified by chromatography on silica gel eluting with ethyl acetate followed by methanol in dichloromethane (5:95). The material obtained was then triturated with diethyl ether to give the title compound as a white solid (74%).

$^1$H NMR (400 MHz, CDCl$_3$): δ1.88 (bd, 2H), 2.00–2.14 (m, 5H), 2.82 (m, 1H), 2.97 (bt, 2H), 3.67 (s, 2H), 4.25 (bd, 2H), 5.29 (s, 2H), 6.61 (dd, 1H), 6.68 (d, 1H), 7.01 (d, 2H), 7.35 (m, 3H), 7.50 (bt, 1H), 8.17 (d, 1H)

LCMS: m/z ES$^+$ 380 [M+H]$^+$

Found; C, 66.09; H, 6.59; N, 18.35; C$_{22}$H$_{25}$N$_5$S requires; C, 66.46; H, 6.64; N, 18.45%.

EXAMPLE 68

4-(4-Benzyl-5-pyrazol-1-ylmethyl-4H-[1,2,4]triazol-3-yl)-3,4,5,6-tetrahydro-2H-[1,2']bipyridinyl

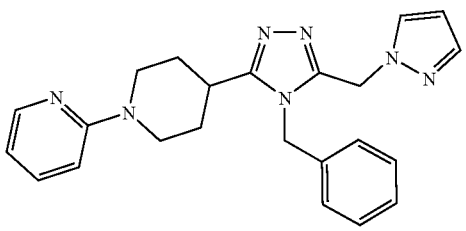

The title compound was prepared from the oxadiazole of preparation 96 by a method similar to that described for example 28 except the compound was purified by chromatography on silica gel eluting with ethyl acetate followed by methanol in dichloromethane (5:95). The material obtained was then triturated with diethyl ether to give the title compound as a buff solid (4%).

$^1$H NMR (400 MHz, CDCl$_3$): δ 1.80 (m, 2H), 2.00 (m, 2H), 1.75 (m, 1H), 2.85 (m, 2H), 4.30 (m, 2H), 5.35 (s, 2H), 5.40 (s, 2H), 6.25 (d, 1H), 6.60 (m, 1H), 6.65 (d, 1H), 6.85 (m, 2H), 7.35 (m, 3H), 7.45 (m, 2H), 7.50 (d, 1H), 8.15 (m, 1H).

LCMS: m/z ES$^+$ 400 [M+H]$^+$, 423 [M+Na]$^+$

Found; C, 68.66; H, 6.34; N, 23.53; C$_{19}$H$_{22}$N$_6$0.15EtOAc requires; C, 68.68; H, 6.40; N, 23.76%.

EXAMPLE 69

4-(4-Benzyl-5-[1,2,3]triazol-2-ylmethyl-4H-[1,2,4]triazol-3-yl)-3,4,5,6-tetrahydro-2H-[1,2']bipyridinyl

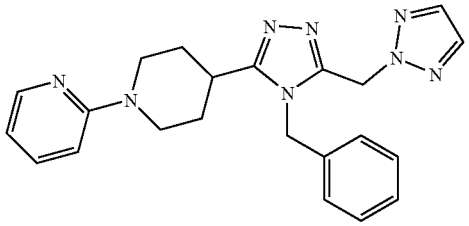

The title compound was prepared from the oxadiazole of preparation 97 by a method similar to that described for example 28 except the compound was purified by chromatography on silica gel eluting with ethyl acetate followed by methanol in dichloromethane (5:95), as a buff solid in 39% yield.

$^1$H NMR (400 MHz, CDCl$_3$): δ 1.80 (m, 2H), 2.05 (m, 2H), 2.80 (m, 1H), 2.85 (m, 2H), 4.30 (d, 2H), 5.30 (s, 2H), 5.70 (s, 2H), 6.60 (m, 1H), 6.65 (d, 1H), 6.85 (m, 2H), 7.35 (m, 3H), 7.45 (t, 1H), 7.55 (m, 2H), 8.15 (m, 1H).

LCMS: m/z ES$^+$ 401 [M+H]$^+$, 423 [M+Na]$^+$

EXAMPLE 70

4-(4-Benzyl-5-[1,2,3]triazol-1-ylmethyl-4H-[1,2,4]triazol-3-yl)-3,4,5,6-tetrahydro-2H-[1,2']bipyridinyl

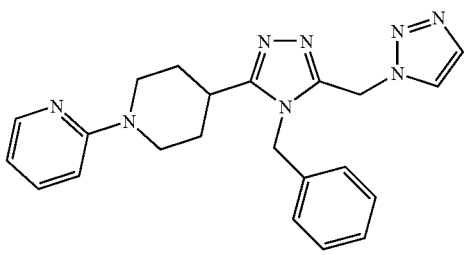

The title compound was prepared from the oxadiazole of preparation 98 by a method similar to that described for example 28 except the compound was purified by chromatography on silica gel eluting with ethyl acetate followed by methanol in dichloromethane (5:95), as a buff solid in a yield of 34%.

$^1$H NMR (400 MHz, CDCl$_3$): δ 1.80 (m, 2H), 2.05 (m, 2H), 2.80 (m, 1H), 2.90 (m, 2H), 4.35 (d, 2H), 5.30 (s, 2H), 5.60 (s, 2H), 6.60 (q, 1H), 6.65 (d, 1H), 6.90 (m, 2H), 7.35 (m, 3H), 7.45 (t, 1H), 7.65 (s, 1H), 7.70 (s, 1H), 8.15 (d, 1H).

LCMS: m/z ES$^+$ 401 [M+H]$^+$

Found; C, 64.17; H, 5.90; N, 26.63; C$_{11}$H$_{22}$N$_6$0.18CH$_2$Cl$_2$ requires; C, 64.07; H, 5.91; N, 26.95%.

EXAMPLE 71

4-[4-Benzyl-5-(pyridin-4-yloxymethyl)-4H-[1,2,4]triazol-3-yl]-3,4,5,6-tetrahydro-2H-[1,2']bipyridinyl

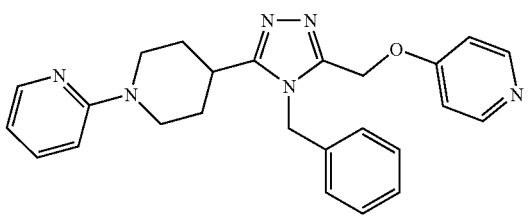

The title compound was prepared from the oxadiazole of preparation 99 by a method similar to that described for example 28 except the compound was purified by chromatography on silica gel eluting with ethyl acetate followed by methanol in dichloromethane (5:95), as a buff solid in a yield of 5%.

$^1$H NMR (400 MHz, CDCl$_3$): δ 1.80 (m, 2H), 2.05 (m, 2H), 2.80 (m, 1H), 2.90 (m, 2H), 4.35 (d, 2H), 5.15 (s, 2H), 5.30 (s, 2H), 6.60 (m, 1H), 6.65 (m, 1H), 7.10 (m, 2H), 7.20 (m, 2H), 7.40 (m, 3H), 7.45 (m, 2H), 8.10 (s, 1H), 8.20 (m, 1H).

LCMS: m/z ES$^+$ 320 [M-C$_5$H$_4$N]$^+$

All of the compounds exemplified above showed a Ki value of less than 500 nM when tested in screen 1.0 (V$_{1A}$ filter binding assay) as described above. Examples of specific compounds are illustrated in table 9. below

TABLE 9

| Example No. | Ki (nM) |
|---|---|
| 4 | 8.6 |
| 16 | 13.19 |
| 17 | 4.67 |
| 24 | 12.08 |
| 25 | 16.12 |
| 26 | 4.5 |

The invention claimed is:

1. A compound of formula (I),

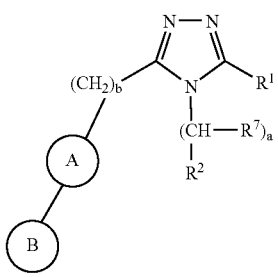

or a pharmaceutically acceptable salt or solvate thereof, wherein $R^1$ represents $C_1$–$C_6$ alkyl, —(CH$_2$)$_c$—[$C_3$–$C_8$ cycloalkyl]-, —(CH$_2$)$_c$—W or —(CH$_2$)$_c$—Z—(CH$_2$)$_d$—W;

W represents $C_1$–$C_6$ alkyl, $C_1$–$C_6$ alkyloxy, —CO$_2$[$C_1$–$C_6$ alkyl], —CONR$^4$R$^5$, a phenyl group, or NR$^4$R$^5$, the phenyl group being optionally substituted with one or more groups independently selected from halogen, CF$_3$, OCF$_3$, R$^3$, OR$^3$, CO$_2$R$^3$, CONR$^4$R$^5$, CN, SO$_2$NR$^4$R$^5$ and NR$^3$SO$_2$Me;

Z represents O or S(O)$_g$;

g represents 0, 1 or 2;

$R^2$ represents a phenyl group, optionally fused to a 5- or 6-membered aryl group the phenyl group and the optionally fused aryl group being optionally substituted with one or more groups independently selected from the list defined below;

Ring A represents piperidindiyl;

Ring B represents a phenyl group or het$^1$, each group being optionally substituted with one or more groups independently selected from the list defined below;

$R^7$ independently represents H, $C_1$–$C_6$ alkyl, OR$^3$, —(CH$^2$)$_e$—R$^3$ or —(CH$_2$)$_f$—O—(CH$_2$)$_e$—R$^3$;

at each occurrence $R^3$ independently represents H, $C_1$–$C_6$ alkyl optionally substituted by Y, —(CH$_2$)$_g$—[$C_3$–$C_8$ cycloalkyl], phenyl, or benzyl;

at each occurrence $R^4$ and $R^5$ independently represent H, $C_1$–$C_6$ alkyl (optionally substituted with $C_1$–$C_6$ alkyloxy), (CH$_2$)$_g$CO$_2$—[$C_1$–$C_6$ alkyl], —SO$_2$Me, —(CH$_2$)$_g$—C$_3$–$C_8$ cycloalkyl], SO$_2$Me, phenyl, benzyl, pyridyl or pyrimidyl;

Y independently represents a phenyl group or NR$^4$R$^5$ the phenyl group being optionally substituted with one or more groups independently selected from halogen, CF$_3$, OCF$_3$, R$^4$, OR$^4$, CO$_2$R$^4$, CONR$^4$R$^5$, CN, SO$_2$NR$^4$R$^5$, NR$^4$SO$_2$Me and —NR$^4$R$^5$;

het$^1$ represents pyridyl or pyrimidinyl substituents for $R^2$, Ring B, and het$^1$ are independently selected from the following list: halogen, CF$_3$, OCF$_3$, R$^3$, —(CH$_2$)$_e$—SO$_2$Me, —(CH$_2$)$_e$—OR$^3$, —(CH$_2$)$_e$CO$_2$R$^3$, —(CH$_2$)$_e$—CONR$^4$R$^5$, —(CH$_2$)$_e$—CN, —(CH$_2$)$_e$—SO$_2$NR$^4$R$^5$, —(CH$_2$)$_e$—NR$^3$SO$_2$Me, —(CH$_2$)$_e$—COR$^3$, —(CH$_2$)$_e$—OCOR$^3$, —(CH$_2$)$_e$—NHCOR$^3$, —(CH$_2$)$_e$—NR$^3$COR$^6$ and —(CH$_2$)$_e$NR$^4$R$^5$;

at each occurrence $R^6$ independently represents H, $C_1$–$C_6$ alkyl optionally substituted by Y, —(CH$_2$)$_g$—[$C_3$–$C_8$ cycloalkyl], phenyl, benzyl, pyridyl or pyrimidyl;

a and b independently represent 0 or 1;

c, d, e and g independently represent 0, 1, 2, 3 or 4;

f independently represents 1, 2, 3 or 4; provided that:

(i) a+b cannot equal 0; and (ii) provided that when $R^1$ represents —(CH$_2$)$_c$—Z—(CH$_2$)$_d$—W and W represents NR$^4$R$^5$ or any N linked heterocyclic group then d must not be 0 or 1; and (iii) provided that when $R^2$ represents a phenyl group substituted by a group of formula —(CH$_2$)$_e$OR$^3$, —(CH$^2$)$_e$—CO$_2$R$^3$ or —CH$_2$)$_e$OCOR$^3$; or het$^1$ is substituted by a group of formula —(CH$_2$)$_e$OR$^3$, —(CH$_2$)$_e$—CO$_2$R$^3$ or —(CH$_2$)$_e$OCOR$^3$; or when $R^7$ represents —OR$^3$ or —(CH$_2$)$_f$—O—(CH$_2$)$_e$—R$^3$ and e is 0; or when W represents a phenyl group substituted with —OR$^3$ or —CO$_2$R$^3$; and $R^3$ represents an alkyl group substituted with Y, and Y represents NR$^4$R$^5$;

then $R^3$ must represent $C_2$–$C_6$ alkyl substituted with Y.

2. A compound according to claim 1, wherein $R^2$ is a phenyl group optionally substituted with one or more groups selected from halogen or —(CH$_2$)$_e$—OR$^3$.

3. A compound according to claim 1 wherein Z is 0.

4. A compound according to claim 1 wherein a is 1 and b is 0.

5. A compound selected from the group consisting of:

(S)-4-[5-Butyl-4-(1-phenyl-ethyl)-4H-[1,2,4]triazol-3-yl]-3,4,5,6-tetrahydro-2H-[1,2']bipyridinyl;

2-[4-(4-Benzyl-5-isobutyl-4H-[1,2,4]triazol-3-yl)-piperidin-1-yl]-pyrimidine;

(S)-4-[5-Methyl-4-(1-phenyl-ethyl)-4H-[1,2,4]triazol-3-yl]-3,4,5,6-tetrahydro-2H-[1,2']bipyridinyl;

4-[4-Benzyl-5-butyl-4H[1,2,4]triazol-3-yl]-3,4,5,6-tetrahydro-2H-[1,2']bipyridinyl;

2-[4-(4-Benzyl-5-isopropyl-4H-[1,2,4]triazol-3-yl)-piperidin-1-yl]-pyrimidine;

2-[4-(4-Benzyl-5-cyclopropyl-4H-[1,2,4]triazol-3-yl)-piperidin-1-yl]-pyrimidine;

(S)-2-{4-[5-Methyl-4-(1-phenyl-propyl)-4H-1,2,4]triazol-3-yl)-piperidin-1-yl]-pyrimidine;

2-[4-(4-Benzyl-5-propyl-4H-[1,2,4]triazol-3-yl) piperidin-1-yl]-pyrimidine;

2-{4-[4-Benzyl-5-(2-chloro-phenoxymethyl)-4H-1,2,4]triazol-3-yl]-piperidin-1-yl}-pyrimidine;

2-[4-(4-Benzyl-5-butyl-4H[1,2,4]triazol-3-yl) piperidin-1-yl]-pyrimidine;

(S)-2-{4-[5Methyl-4(1-phenyl-ethyl)-4H-1,2,4triazol-3-yl)-piperidin-1-yl]-pyrimidine;

2-{4-[4-Benzyl-5-(4-fluoro-phenoxymethyl)-4H-[1,2,4]triazol-3-yl]-piperidin-1-yl}pyrimidine;

2-{4-[5-Methyl-4-(3-methyl-benzyl)-4H-[1,2,4]triazol-3-yl)-piperidin-1-yl]pyrimidine;

(S)-2-{4-[5-Methyl-4(1-phenyl-ethyl)-4H-[1,2,4]triazol-3ylmethyl]-piperidin-1-yl}-pyrimidine;

2-{4-[4-(3Fluoro-benzyl)-5-methyl-4H-[1,2,4]triazol-3yl)-piperidin-1-yl]pyrimidine;

4-(4-Benzyl-5-benzyloxymethyl-4H-[1,2,4]triazol-3-yl)-3,4,5,6-tetrahydro-2H-[1,2']bipyridinyl;

4-(4-Benzyl-5-methyl-4H-[1,2,4]triazol-3-yl)-3,4,5,6-tetrahydro-2H-[1,2']bipyridinyl;

(R)-2-{3-Methyl-5-(1-pyrimidin-2-yl-piperidin-4-yl)-[1,2,4]triazol-4-yl]-2-phenyl-ethanol;

2-[4-(4Benzyl-5-methyl-4H-[1,2,4]triazol-3-yl)-piperidin-1-yl]-4-methyl-pyrimidine;

2-[4-(4-Benzyl-5-methyl-4H-[1,2,4]triazol-3-yl) piperidin-1-yl]-pyrimidine;

4-(4-Benzyl-5-methyl-4H-[1,2,4]triazol-3-yl)-1-phenyl-piperidine;

4-[4-(4-Fluoro-benzyl)-5-methyl-4H-[1,2,4]triazol-3-yl]-3,4,5,6-tetrahydro-2H-[1,2']bipyridinyl;

4-[4-(3-Methoxy-benzyl)-5-methyl-4H-[1,2,4]triazol-3-yl]-3,4,5,6-tetrahydro-2H-[1,2']bipyridinyl;

4-[5-Methyl-4-(3-methyl-benzyl)-4H-[1,2,4]triazol-3-yl]-3,4,5,6-tetrahydro-2H-[-1,2']bipyridinyl;

4-[4-(3-Chloro-benzyl)-5-methyl-4H-[1,2,4]triazol-3-yl]-3,4,5,6-tetrahydro-2H-[1,2']bipyridinyl;

N-Benzyl-2-[4-benzyl-5-(3,4,5,6-tetrahydro-2H-[1,2']bipyridinyl-4-yl)-4H-[1,2,4]triazol-3-yl]-acetamide;

2-[4Benzyl-5-(3,4,5,6-tetrahydro-2H-[1,2']bipyridinyl-4-yl)-4H-[1,2,4]triazol-3-ylmethoxy]-ethylamine;

[4-Benzyl-5-(3,4,5,6-tetrahydro-2H-[1,2']bipyridinyl-4-yl)-4H-[1,2,4]triazol-3-ylmethyl]-ethyl-amine;

[4-Benzyl-5-(3,4,5,6-tetrahydro-2H-[1,2']bipyridinyl-4-yl)-4H-[1,2,4]triazol-3-ylmethyl]-(2-methoxy-ethyl)-amine;

[4-Benzyl-5-(3,4,5,6-tetrahydro-2H-[1,2']bipyridinyl-4-yl)-4H-[1,2,4]triazol-3-ylmethyl]-(3-methoxy-propyl)-amine;

{[4-Benzyl-5-(3,4,5,6-tetrahydro-2H-[1,2']bipyridinyl-4-yl)-4H-[1,2,4]triazol-3-ylmethyl]-methyl-amino}-acetic acid tert-butyl ester;

4-(4-Benzyl-5-ethoxymethyl-4H-[1,2,4]triazol-3-yl)-3,4,5,6-tetrahydro-2H-[1,2']bipyridinyl;

4-[4-Benzyl-5-(2-methoxy-ethoxymethyl)-4H-[1,2,4]triazol-3-yl]-3,4,5,6-tetrahydro-2H-[1,2']bipyridinyl;

[4-Benzyl-5-(3,4,5,6-tetrahydro-2H-[1,2']bipyridinyl-4-yl)-4H-[1,2,4]triazol-3-ylmethoxyl-acetic acid tert-butyl ester;

N-Benzyl-2-[4-benzyl-5-(3,4,5,6-tetrahydro-2H-[1,2']bipyridinyl-4-yl)-4H-[1,2,4]triazol-3-ylmethoxy]-acetamide; and 4-(4-Benzyl-5-methylsulfanylmethyl-4H-[1,2,4]triazol-3-yl)-3,4,5,6-tetrahydro-2H-[1,2']bipyridinyl.

6. A compound selected from the group consisting of:

4-[4-Benzyl-5-butyl-4H-[1,2,4]triazol-3-yl]-3,4,5,6-tetrahydro-2H-[1,2']bipyridinyl; and 4-(4-Benzyl-5-benzyloxymethyl-4H-[1,2,4]triazol-3-yl)-3,4,5,6-tetrahydro-2H-[1,2']bipyridinyl.

7. A method of treatment of aggression, anorexia nervosa; anxiety depression, or comprising dysmenorrhoea, administering a therapeutically effective amount of a compound of formula (I), claim 1, to a patient suffering from such a disorder.

8. A method according to claim 7 wherein the disorder is dysmenorrhoea or anxiety.

9. A pharmaceutical formulation including a compound of formula (I), claim 1, or a pharmaceutically acceptable salt or solvate thereof, together with a pharmaceutically acceptable excipients, diluent or carrier.

* * * * *